(12) United States Patent
Bhowmik et al.

(10) Patent No.: US 10,316,050 B2
(45) Date of Patent: Jun. 11, 2019

(54) PT (IV) COMPLEXES CONTAINING 4,4'-DISUBSTITUTED-2,2'-BIPYRIDYL AND THEIR USE IN CANCER THERAPY

(71) Applicant: THE BOARD OF REGENTS OF THE NEVADA SYSTEM OF HIGHER EDUCATION ON BEHALF OF THE UNIVERSITY OF NEVADA, LAS VEGAS, Las Vegas, NV (US)

(72) Inventors: Pradip K. Bhowmik, Henderson, NV (US); Bryan L. Spangelo, Henderson, NV (US); Van Vo, Las Vegas, NV (US); Haesook Han, Henderson, NV (US); Ontida Tanthmanatham, Las Vegas, NV (US)

(73) Assignee: The Board of Regents of the Nevada System of Higher Education on behalf of the University of Nevada, Las Vegas, Las Vegas, NV (US)

( * ) Notice: Subject to any disclaimer, the term of this patent is extended or adjusted under 35 U.S.C. 154(b) by 127 days.

(21) Appl. No.: 15/503,334

(22) PCT Filed: Aug. 13, 2015

(86) PCT No.: PCT/US2015/045105
§ 371 (c)(1),
(2) Date: Feb. 10, 2017

(87) PCT Pub. No.: WO2016/025742
PCT Pub. Date: Feb. 18, 2016

(65) Prior Publication Data
US 2017/0233423 A1 Aug. 17, 2017

Related U.S. Application Data

(60) Provisional application No. 62/036,694, filed on Aug. 13, 2014.

(51) Int. Cl.
*C07F 15/00* (2006.01)
*A61K 31/555* (2006.01)

(52) U.S. Cl.
CPC ........ *C07F 15/0093* (2013.01); *A61K 31/555* (2013.01)

(58) Field of Classification Search
None
See application file for complete search history.

(56) References Cited

U.S. PATENT DOCUMENTS

| | | |
|---|---|---|
| 4,177,263 A | 12/1979 | Rosenberg et al. |
| 4,394,319 A | 7/1983 | Hydes et al. |
| 4,845,124 A | 7/1989 | Kidani et al. |
| 5,072,011 A | 12/1991 | Abrams et al. |
| 5,244,919 A | 9/1993 | Abrams et al. |
| 8,703,756 B2 | 4/2014 | Spangelo et al. |
| 2012/0329767 A1 | 12/2012 | Pfeffer et al. |
| 2013/0022546 A1 | 1/2013 | Wall et al. |
| 2013/0324511 A1 | 12/2013 | Che et al. |

FOREIGN PATENT DOCUMENTS

WO WO-2016/025742 A1 2/2016

OTHER PUBLICATIONS

Al-Allaf, T.A.K. et al., Chemical Properties and Cytotoxic Activity of Complexes of Platunum(II) and Palladium(II) Containing dmso and Various Anions; Synthesis and Structural Characterization of [Pt(dmso)$_{2\{O2}$(CO)$_2$CCH$_2$CH$_2$CH$_2$}]. Transition Met Chem. 1998; 23(4):403-6.

Allenbaugh, R.J. et al., Dialkyl 2,2'-bipyridine-4,4'-dicarboxylate Complexes of Pt$^{II}$, Cd$^{II}$ and Re$^I$ : the Effects of Metal Centre Geometry and Ligand Substitution on Phase Behaviour. Liq Crys. 2013; 40:783-6.

Allenbaugh, R.J. et al., Effect of Axial Interactions on the Formation of Mesophases: Comparison of the Phase Behavior of Dialkyl 2,2'-bipyridyl-4,4'-dicarboxylate Compleses of Pt(II), Pt(IV), and Pt(II)/Pt(IV) Molecular Alloys. Chem Mater. 2012; 24(23):4517-30.

Baldrick, P., Pharmaceutical Excipient Development: The Need for Preclinical Guidance. Regul Toxicol Pharmacol. 2000; 32(2):210-8.

Bellusci, A. et al., Synthesis and Luminescent Properties of Novel Lanthanide(III) β-Diketine Complexes with Nitrogen p,p'-Disubstituted Aromatic Ligands. Inorg Chem. 2005; 44(6):1818-25.

Bos, K.D. et al., Improved Synthesis of 4,4'-Disubstituted-2,2'-Bipyridines. Synthetic Communications. 1979; 9(6):497-504.

Boulares, A.H. et al., Role of Poly(ADP-ribose) Polymerase (PARP) Cleavage in Apoptosis. J Biol Chem. 1999; 274(33):22932-40.

Bray, F. et al., Global Cancer Transitions According to the Human Development Index (2008-2030): a Population-Based Study. Lancet Oncol. 2012; 13(8):790-801.

Case, F.H., The Synthesis of Certain Substituted 2,2'-Bipyridyls[1.] J Am Chem Soc. 1946; 68(12):2574-7.

Casini, A. and J. Reedijk, Interactions of Anticancer Pt Compounds with Proteins: an Overlooked Topic in Medicinal Inorganic Chemistry? Chem Sci. 2012; 3:3135-44.

Charman, W.N., Lipids, Lipophilic Drugs, and Oral Drug Delivery—Some Emerging Concepts. J Pharm Sci. 2000; 89(8):967-78.

Cherkashina, N.V. et al., Unusual Sandwich Platinum(II) Complex: [Pt(phen)$_2$]$^{2+}$ Cation Betwen Two Pt(phen)(OOCMe)$_2$ Molecules. Russian J Inorg Chem. 2014; 59(5):446-54.

Ferlay, J. et al., Cancer Incidence and Mortality Worldwide: Sources, Methods and Major Patterns in GLOBOCAN 2012. Int J Cancer. 2013; 136:E359-86.

(Continued)

*Primary Examiner* — Jeffrey S Lundgren
*Assistant Examiner* — Tori Strong
(74) *Attorney, Agent, or Firm* — Ballard Spahr LLP

(57) ABSTRACT

Platinum-containing compounds for the treatment of disease, such as, for example, cancer, are provided herein. Specifically, platinum Pt(IV) complexes with a substituted 2,2'-bipyridine ring structure are provided, as are methods for using the complexes. This abstract is intended as a scanning tool for purposes of searching in the particular art and is not intended to be limiting of the present invention.

20 Claims, 27 Drawing Sheets

(56) References Cited

OTHER PUBLICATIONS

Florea, A.M. and D. Büsselberg, Cisplatin as an Anti-Tumor Drug: Cellular Mechanism of Activity, Drug Resistance and Induced Side Effects. Cancers. 2011; 3(1):1351-71.
Geary, E.A.M. et al., Synthesis, Structure, and Properties of [Pt(II)(diimine)dithiolate)] Dyes with 3,3'-,4,4'-, and 5,5'-Disubstituted Bipyridyl: Applications in Dye-Sensitized Solar Cells. Inorg Chem. 2005; 44: 242-50.
Geary, E.A.M. et al., Spectroscopic, Electrochemical and Computational Study of Pt-diimine-dithiolene Complexes: Rationalising the Properties of Solar Cell Dyes. Dalton Trans. 2008; 28: 3701-8.
Göeransson, E. et al., Photoinduced Electron Transfer in Zn(II)porphyrin-Bridge-Pt(II)acetylide Complexes: Variation in Rate with Anchoring Group and Position of the Bridge. Inorg Chem. 2010; 49: 9823-32.
Graf, N. and S.J. Lippard, Redox Actication of Metal-Based Prodrugs as a Strategy for Drug Delivery. Adv Drug Deliv Rev. 2012; 64(11):993-1004.
Harper, B.W. et al., Advances in Platinum Chemotherapeutics. Chem Eur J. 2010; 16(24):7064-77.
Lee, Y.A. et al., Oxidation of Pt(II) to Pt(IV) Complex with Hydrogen Peroxide in Glycols. Inorg Chem Commun. 2003; 6(3):249-51.
Liu, K.Y. et al., Synthesis and Characterization of Cross-Linkable Ruthenium Dye with Ion Coordinating Property for Dye-Sensitized Solar Cells. Polymer. 2011; 52(15):3318-24.
Mackay, F.S. et al., A Potent Cytotoxic Photoactivated Platinum Complex. Proc Natl Acad Sci U.S.A. 2007; 104(52):20743-8.
McGarrah, J.E. and R. Eisenberg, Dyads for Photoinduced Charge Separation Based on Platinum Diimine Bis(acetylide) Chromophores: Synthesis, Luminescence and Transient Absorption Studies. Inorg Chem. 2003; 42(14):4355-65.
McInnes, E.J.L. et al., On the electronic structure of $[Pt(4,4'-X_2-bipy)Cl_2]^{0/-/2-}$ : an electrochemical and spectroscopic (UV/Vis, EPR, ENDOR) study. J Chem Soc, Dalton Trans: Inorg Chem. 1999; 23:4203-8.
Powell, M.F. et al., Compendium of Excipients for Parenteral Formulations. PDA J Pharm Sci Technol. 1998; 52(5):238-311.
Price, J.H. et al., Palladium(II) and Platinum(II) Alkyl Sulfoxide Complexes. Examples of Sulfur-Bonded, Mixed Sulfur- and Oxygen-Bonded, and Totally Oxygen-Bonded Complexes. Inorg Chem. 1972; 11(6):1280-4.
Pucci, D. et al., Induction of Mesomorphiam Through Supramolecular Association in Coordination Pd (II) Compounds of Dialkyl 2,2'-Bipyridine-4,4'-Dicarboxylates. Mol Cryst Liq Cryst. 2003; 395(1):325-335.
Pucci et al., Self-organization of dipolar 4,4'-disubstituted 2,2'-bipyridine metal complexes into luminescent lamellar liquid crystals. Eur J Inorg Chem. 2003; 19: 3649-61.
Remington's Pharmaceutical Sciences. 18th ed., Mack Publishing Co., Easton, PA (1990).
Rose, N.R. et al., Inhibitor Scaffolds for 2-Oxoglutrate-Dependent Histone Lysine Demethylases. J Med Chem. 2008; 51(22):7053-6.
Safa, M. and R.J. Puddephatt, Organoplatinum Complexes with an Ester Substituted Bipyridine Ligand: Oxidative Addition and Supramolecular Chemistry. J Organomet Chem. 2013; 724: 7-16.
Tzeng et al., Palladium(II) and Platinum(I) analogues of luminescent diimine triangulo complexes supported by triply bridging sulfide ligands: structural and spectroscopic comparisons. Inorg Chem. 2001; 40(26): 6699-704.
Vo, V. et al., Synthesis of $[PtCl_2(4,4'-dialkoxy-2,2'-bipyridine)]$ complexes and Their in Vitro Anticancer Properties. Metallomics. 2013; 5(8):973-87.
Wang, W. et al., Extraction of Metal Ions with Non-Fluorous Bipyridine Derivaties as Chelating Ligands in Supercritical Carbon Dioxide. J Supercritical Fluids. 2009; 51(2):181-7.
Wang, W., Lyophilizaion and Development of Solid Protein Pharmaceuticals. Int J Pharm. 2000; 203(1-2):1-60.
Wang, X. and Z. Guo, Targeting and Delivery of Platinum-Based Anticancer drugs. Chem Soc Rev. 2013; 42(1):202-24.
Weinstein et al., Picosecond time-resolved infrared spectroscopic investigation of excited state dynamics in a $Pt^{II}$ diimine chromophore. Chemical Communications (Cambridge, United Kingdom). 2002; 4: 382-3.
Wexselblatt, E. and D. Gibson, What Do We Know About the Reduction of Pt(IV) Pro-Drugs? J Inorg Biochem. 2012; 117:220-9.
Zhang, J. et al., Photogeneration of hydrogen from water using an integrated system based on TiO2 and platinum(II) diimine dithiolate sensitizers. J Amer Chem Soc. 2007; 129: 7726-7.
International Search Report and Written Opinion dated Nov. 23, 2015 by the International Searching Authority for International Patent Application No. PCT/US2015/045105, which was filed on Aug. 13, 2015 and published as WO 2016/025742 dated Feb. 18, 2016 (Inventor—Bhowmik et al.; Applicant—Univ. of Nevada, Las Vegas; (9 pages).
International Preliminary Report on Patentability dated Feb. 14, 2017 by the International Searching Authority for International Patent Application No. PCT/US2015/045105, which was filed on Aug. 13, 2015 and published as WO 2016/025742 dated Feb. 18, 2016 (Inventor—Bhowmik et al.; Applicant—Univ. of Nevada, Las Vegas; (8 pages).

PT (IV) COMPLEXES CONTAINING 4,4'-DISUBSTITUTED-2,2'-BIPYRIDYL AND THEIR USE IN CANCER THERAPY

CROSS-REFERENCE TO RELATED APPLICATIONS

This application claims the benefit of and priority under 35 U.S.C. § 371 to PCT/US2015/045105, filed Aug. 13, 2015, which claims the benefit under 35 U.S.C. § 119(e) to U.S. Provisional Application No. 62/036,694, filed Aug. 13, 2014, which applications are incorporated herein by reference in their entireties.

BACKGROUND

In 2012, there were 8.2 million cancer deaths and 14.1 million new cases of cancer worldwide (Ferlay et al., GLOBOCAN 2012 v1.0, Cancer Incidence and Mortality Worldwide: IARC CancerBase No. 11 [Internet]. Lyon, France: International Agency for Research on Cancer; 2013; available at globocan.iarc.fr). These values are projected to increase to an estimated 22.2 million new cases and 13.2 million deaths by 2030 (Ferlay et al., *Lancet Oncol* 13:790-801, 2012). While new treatment techniques are being explored, the use of chemotherapeutic drugs, including platinum- (Pt-) based drugs has remained mainstream (see, e.g., Harper et al., *Chem Eur J* 16:7064-7077, 2010; Casini and Reedijk, *Chem Sci* 3:3135-3144, 2012; Wexselblatt and Gibson, *J Inorg Biochem* 117:220-229, 2012; and Florea and Büsselberg, *Cancers* 3:1351-1371, 2011). Only a few platinum drugs have been approved for clinical use, however. These include cisplatin, carboplatin, and oxaliplatin, which are Pt(II) complexes approved for use worldwide, as well as lobaplatin, nedaplatin, and heptaplatin, which are approved for use in China, Japan, and Korea, respectively (Harper et al., supra; Casini and Reedijk, supra; Wexselblatt and Gibson, supra; Florea and Büsselberg, supra; and Wang and Guo, *Chem Soc Rev* 42:202-224, 2013).

Despite being commonly prescribed, the clinical application of platinum drugs continues to be limited by a narrow spectrum of activity, resistance, and toxic side effects. Accordingly, there remains a need for platinum-based drugs having improved efficacy and reduced toxicity.

SUMMARY

In accordance with the purpose(s) of the invention, as embodied and broadly described herein, the invention, in one aspect, relates to platinum (IV) complexes and methods of using these complexes for the treatment of a disease such as, for example, cancer.

Disclosed are methods for treating a subject having cancer, the method comprising administering to the subject an effective amount of a composition comprising a complex having a structure represented by a formula:

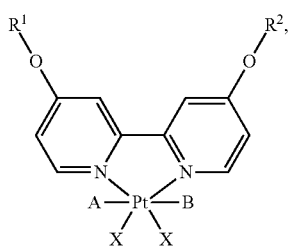

wherein each X is independently —Br, —Cl, or —I; and wherein each of A and B is independently selected from —Br, —Cl, —I, —OH, and —OC(O)R$^3$; wherein R$^3$ is —(CH$_2$)$_p$CH$_3$; and wherein p is selected from 0, 1, 2, 3, 4, 5, 6, 7, 8, 9, and 10; wherein each of R$^1$ and R$^2$ is independently selected from —(CH$_2$)$_n$CH$_3$, —(CH$_2$)$_n$OCH$_3$, and —(CH$_2$)$_n$[O(CH$_2$)$_m$]$_y$O(CH$_2$)$_z$CH$_3$; wherein n is selected from 1, 2, 3, 4, 5, 6, 7, 8, 9, and 10; wherein each of m, y, and z is independently selected from 0, 1, 2, 3, 4, 5, 6, 7, 8, 9, and 10, or a pharmaceutically acceptable derivative thereof.

Also disclosed are complexes having a structure represented by a formula:

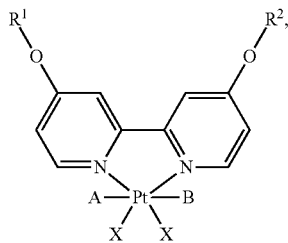

wherein each of R$^1$ and R$^2$ is independently selected from —(CH$_2$)$_n$CH$_3$, —(CH$_2$)$_n$OCH$_3$, and —(CH$_2$)$_n$[O(CH$_2$)$_m$]$_y$O(CH$_2$)$_z$CH$_3$; wherein n is selected from 1, 2, 3, 4, 5, 6, 7, 8, 9, and 10; wherein each of m, y, and z is independently selected from 0, 1, 2, 3, 4, 5, 6, 7, 8, 9, and 10; wherein each X is independently —Br, —Cl, or —I; and wherein each of A and B is independently selected from —Br, —Cl, —I, —OH, and —OC(O)R$^3$; wherein R$^3$ is —(CH$_2$)$_p$CH$_3$; and wherein p is selected from 0, 1, 2, 3, 4, 5, 6, 7, 8, 9, and 10, or a pharmaceutically acceptable derivative thereof.

Also disclosed are methods for treating a subject having cancer comprising administering to the subject an effective amount of a composition comprising a [Pt(IV)X$_2$AB(4,4'-bis[C(O)OR]-2,2'-bipyridine)] complex have a structure represented by a formula:

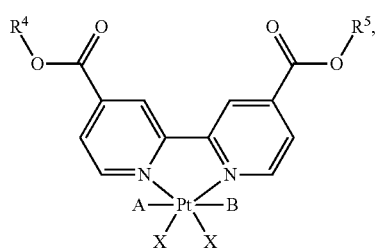

wherein R$^4$ and R$^5$ are independently selected from the group consisting of —(CH$_2$)$_t$CH$_3$, —C(CH$_3$)$_3$, —CH$_2$CH (CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$, with t being an integer from 0 to 7; each X is independently Br, Cl, or I; and A and B are independently selected from the group consisting of X, —OH, and —OC(O)R$^3$, where R$^3$ is —(CH$_2$)$_p$CH$_3$, and p is an integer from 0 to 10.

Also disclosed are [Pt(IV)X$_2$AB(4,4'-bis[C(O)OR]-2,2'-bipyridine)] complexes have a structure represented by a formula:

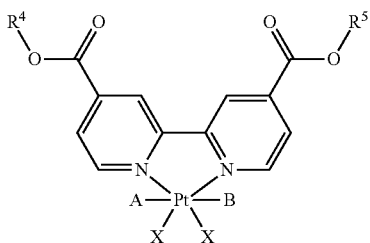

wherein R⁴ and R⁵ are independently selected from the group consisting of —(CH₂)ₜCH₃, —C(CH₃)₃, —CH₂CH(CH₂CH₃)CH₂CH₂CH₂CH₃, —(CH₂CH₂O)₂CH₂CH₃, —CH₂CH₂O)₃CH₂CH₃, —(CH₂CH₂O)₃(CH₂)₃CH₃, and —(CH₂CH₂O)₄CH₃, with t being an integer from 0 to 7; each X is independently Br, Cl, or I; and A and B are independently selected from the group consisting of X, —OH, and —OC(O)R³, where R³ is —(CH₂)ₚCH₃, and p is an integer from 0 to 10.

Also disclosed are methods for treating a subject having cancer, the method comprising administering to the subject an effective amount of a composition comprising a complex have a structure represented by a formula selected from:

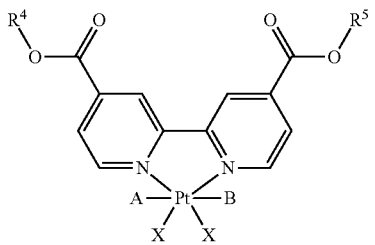

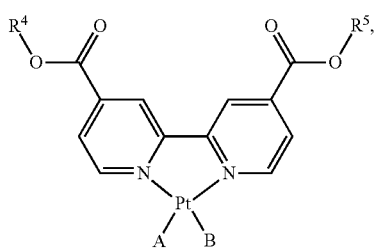

wherein each of R⁴ and R⁵ is independently selected from —(CH₂)ₜCH₃, —C(CH₃)₃, —CH₂CH(CH₂CH₃)CH₂CH₂CH₂CH₃, —(CH₂CH₂O)₂CH₂CH₃, —(CH₂CH₂O)₃ CH₂CH₃, —(CH₂CH₂O)₃(CH₂)₃CH₃, and —(CH₂CH₂O)₄ CH₃; wherein t is selected from 0, 1, 2, 3, 4, 5, 6, and 7; wherein each X is independently —Br, —Cl, or —I; and wherein each of A and B is independently selected from —Br, —Cl, —I, —OH, and —OC(O)R³; wherein R³ is —(CH₂)ₚCH₃; and wherein p is selected from 0, 1, 2, 3, 4, 5, 6, 7, 8, 9, and 10, or a pharmaceutically acceptable derivative thereof.

Also disclosed are complexes having a structure represented by a formula selected from:

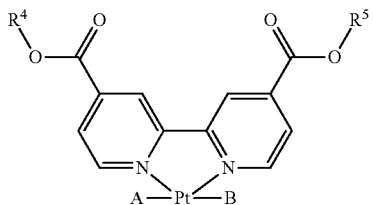

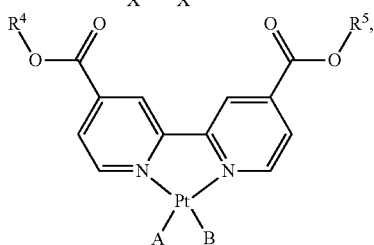

wherein each of R⁴ and R⁵ is independently selected from —(CH₂)ₜCH₃, —C(CH₃)₃, —CH₂CH(CH₂CH₃)CH₂CH₂CH₂CH₃, —(CH₂CH₂O)₂CH₂CH₃, —(CH₂CH₂O)₃ CH₂CH₃, —(CH₂CH₂O)₃(CH₂)₃CH₃, and —(CH₂CH₂O)₄ CH₃; wherein t is selected from 0, 1, 2, 3, 4, 5, 6, and 7; wherein each X is independently —Br, —Cl, or —I; and wherein each of A and B is independently selected from —Br, —Cl, —I, —OH, and —OC(O)R³, provided that A, B, and each X are not simultaneously —Br, simultaneously —Cl, or simultaneously —I; wherein R³ is —(CH₂)ₚCH₃; and wherein p is selected from 0, 1, 2, 3, 4, 5, 6, 7, 8, 9, and 10, or a pharmaceutically acceptable derivative thereof.

Also disclosed are complexes having a structure represented by a formula selected from:

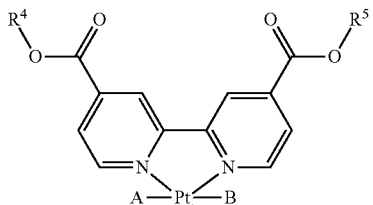

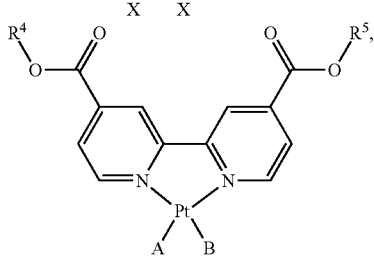

wherein each of R⁴ and R⁵ is independently selected from —(CH₂CH₂O)₂CH₂CH₃, —(CH₂CH₂O)₃CH₂CH₃, —(CH₂CH₂O)₃(CH₂)₃CH₃, and —(CH₂CH₂O)₄CH₃; wherein t is selected from 0, 1, 2, 3, 4, 5, 6, and 7; wherein each X is independently —Br, —Cl, or —I; and wherein each of A and B is independently selected from —Br, —Cl, —I, —OH, and —OC(O)R³; wherein R³ is —(CH₂)ₚCH₃; and wherein p is selected from 0, 1, 2, 3, 4, 5, 6, 7, 8, 9, and 10, or a pharmaceutically acceptable derivative thereof.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 4A shows a reaction scheme for making Pt(II) complexes, while

Figure 1:
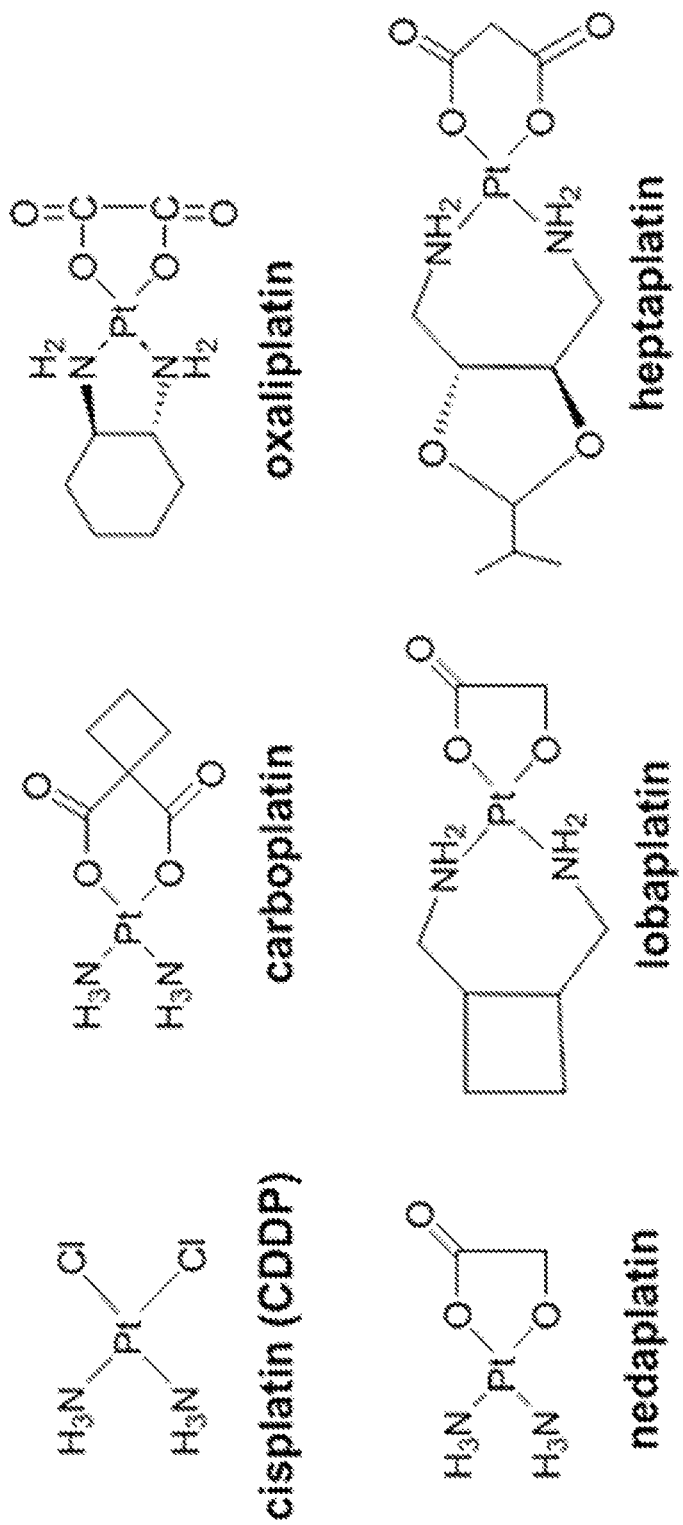
FIG. 1 shows the structures of cisplatin and other Pt(II) complexes in clinical use.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "catalytically effective" refers to the amount of a catalyst that is sufficient to facilitate a reaction (e.g., atom-transfer radical polymerization as disclosed herein).

B. PLATINUM COMPLEXES

Figure 2:
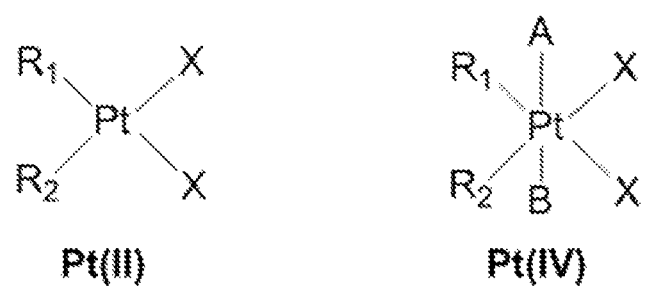
FIG. 2 shows the general structures of Pt(II) and Pt(IV) complexes.

Herein, platinum complexes, particularly Pt(IV) complexes, having a substituted 2,2'-bipyridine ring structure are described. Pt(II) complexes have four coordinating ligands attached to the Pt center, giving them a +2 oxidation state, while Pt(IV) complexes (e.g., those shown in FIG. 5) have six coordinating ligands, giving them a +4 oxidation state, as shown in FIG. 2.

Figure 3A:
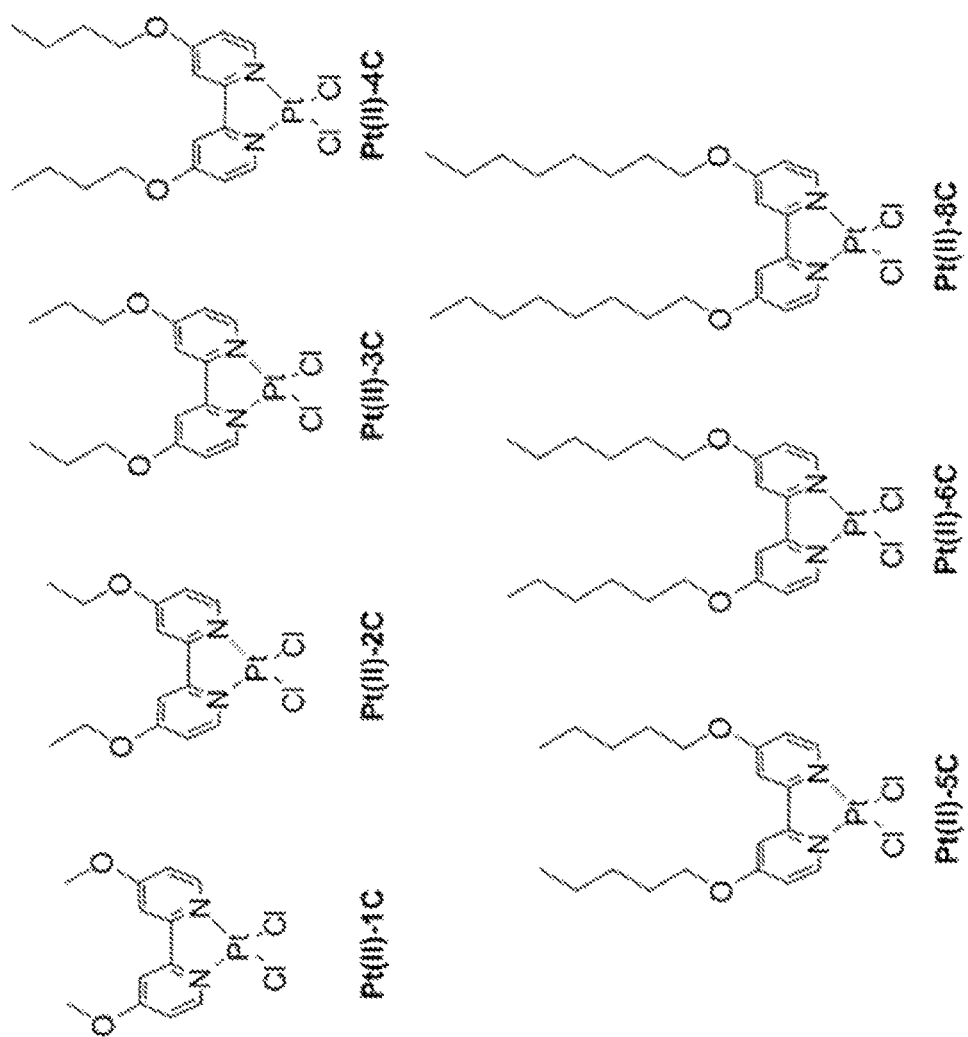
FIG. 3A shows the chemical structures of [Pt(II)Cl$_2$(4,4'-dialkoxy-2,2'-bipyridine)] complexes.
Figure 3B:
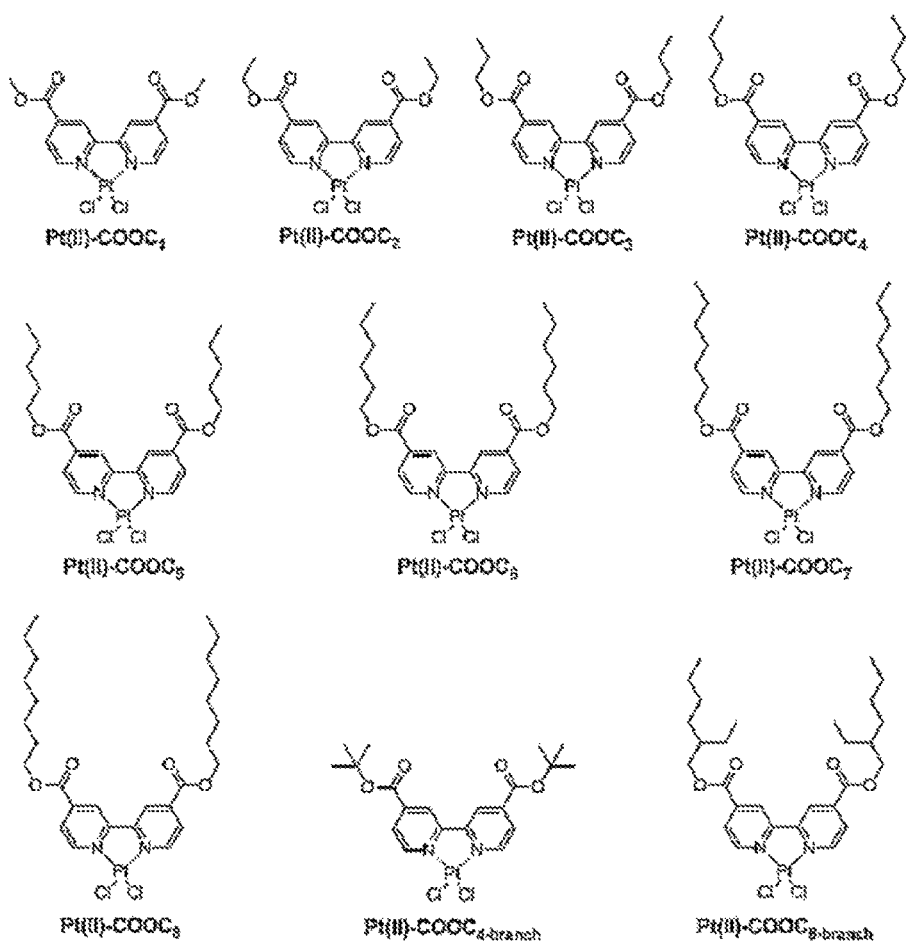
FIG. 3B and FIG. 3C show chemical structures of [Pt(II)Cl$_2$(di(alkyl)-2,2'-bipyridine-4,4'-dicarboxylate)] and [Pt(II)Cl$_2$(di(oligooxyethyleneoxyalkyl)-2,2'-bipyridine-4,4'-dicarboxylate)] complexes.
Figure 3C:
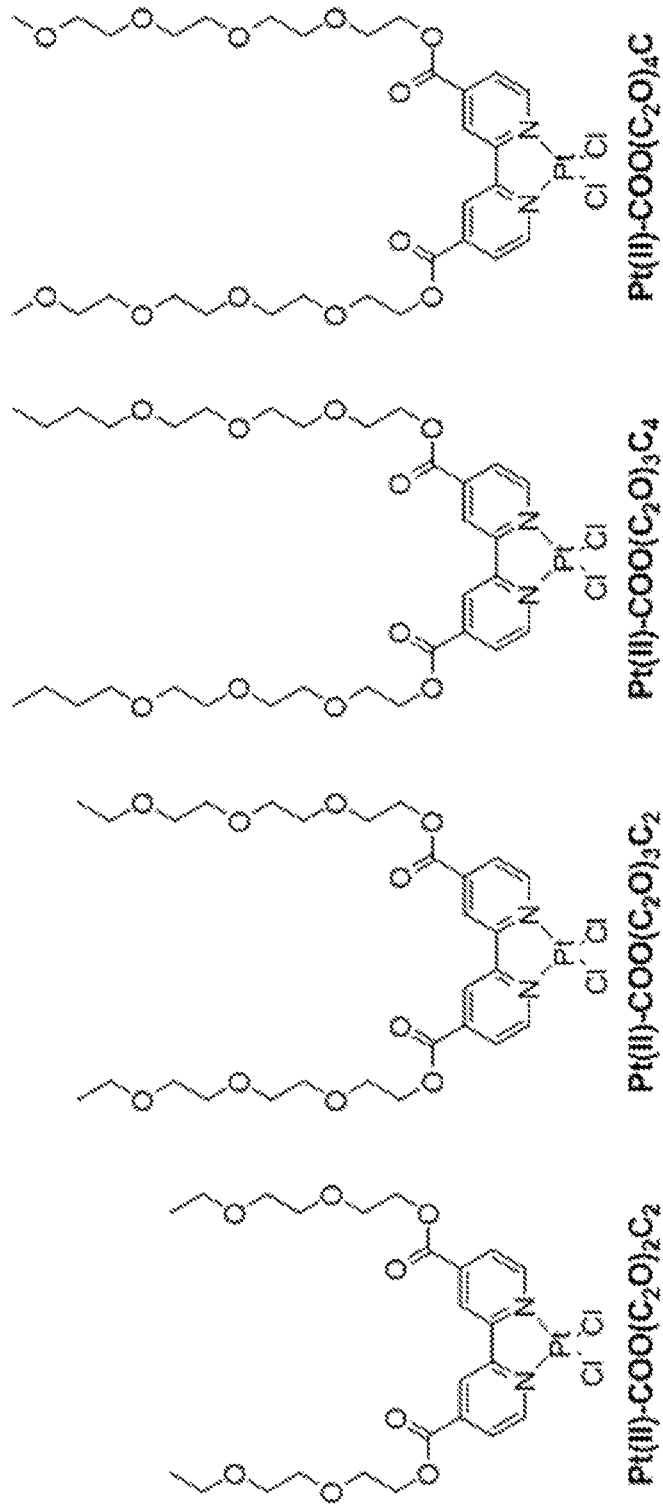
Figure 5A:
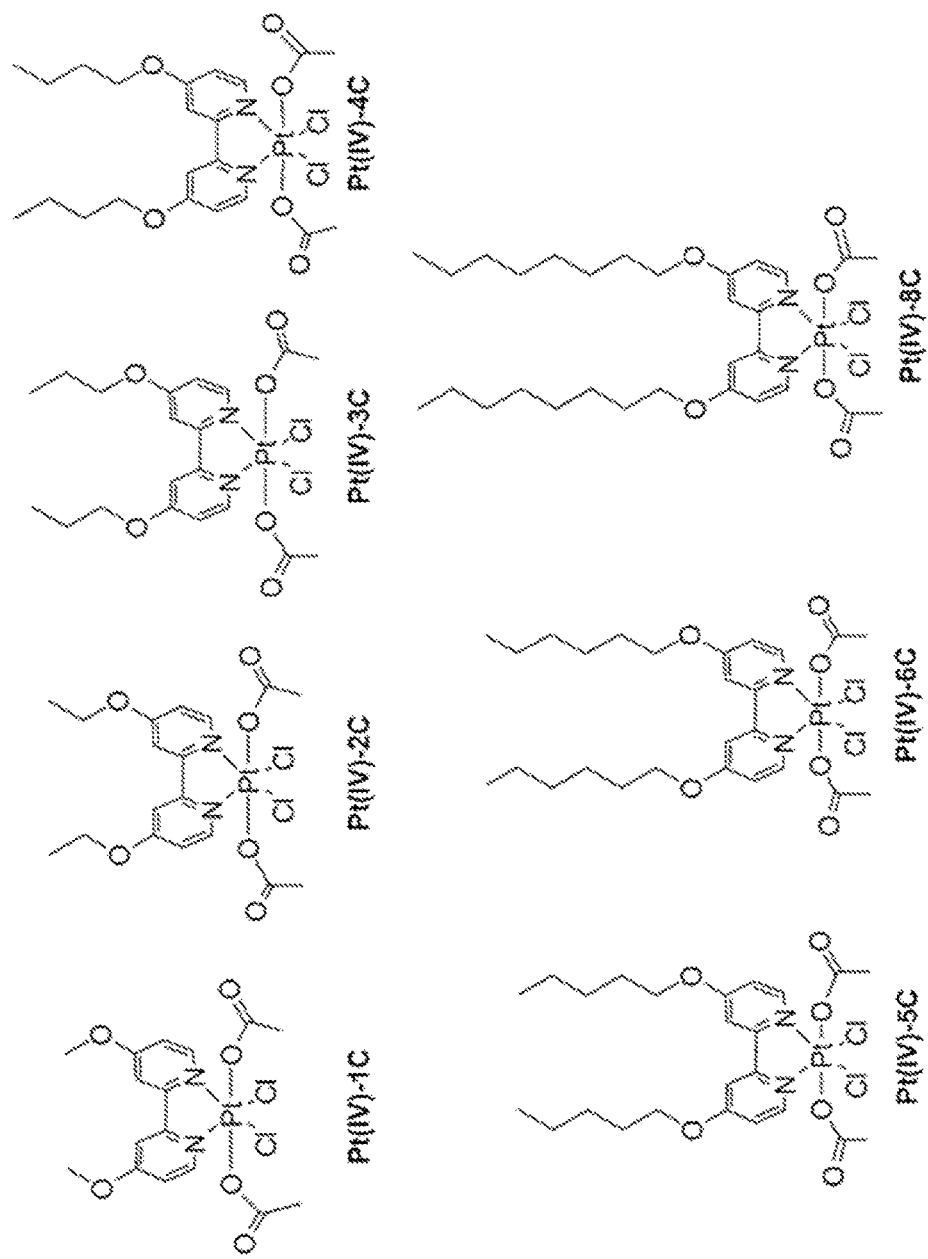
FIG. 5A shows the chemical structures of the synthesized [Pt(IV)Cl$_2$(OAc)$_2$(4,4'-dialkoxy-2,2'-bipyridine)] complexes.
Figure 5B:
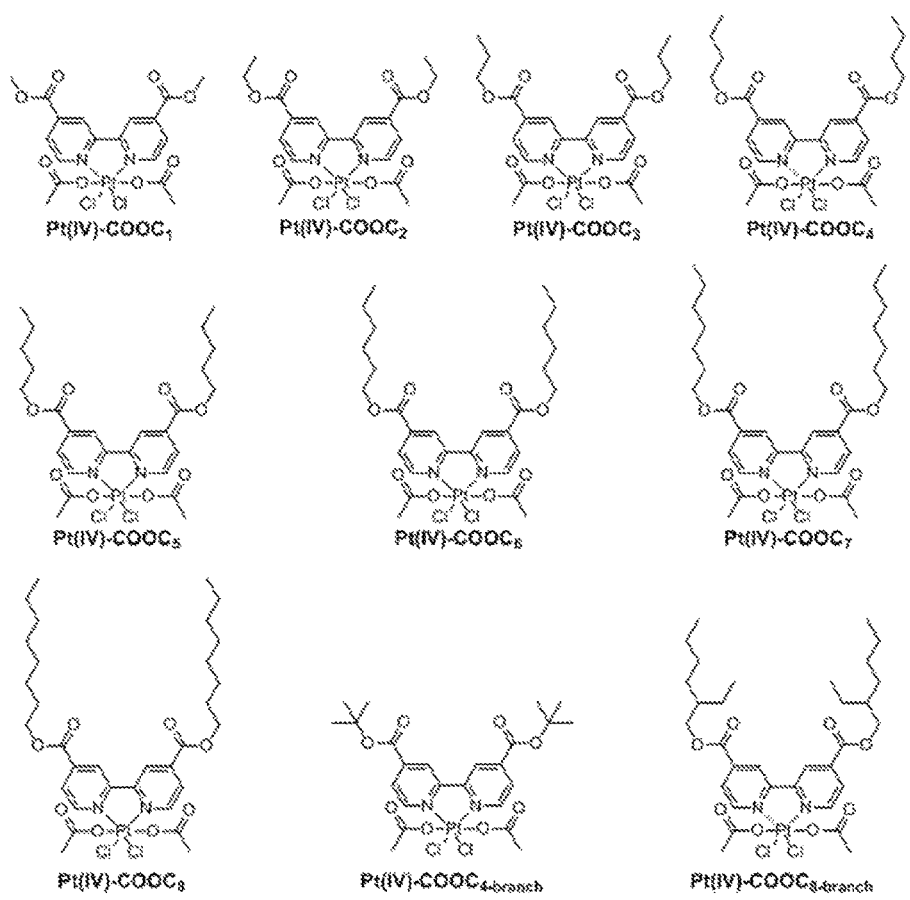
FIG. 5B and FIG. 5C show chemical structures of [Pt(IV)Cl$_2$(OAc)$_2$(di(alkyl)-2,2'-bipyridine-4,4'-dicarboxylate)] and [Pt(IV)Cl$_2$(OAc)$_2$(di(oligooxyethyleneoxyalkyl))-2,2'-bipyridine-4,4'-dicarboxylate)] complexes.
Figure 5C:
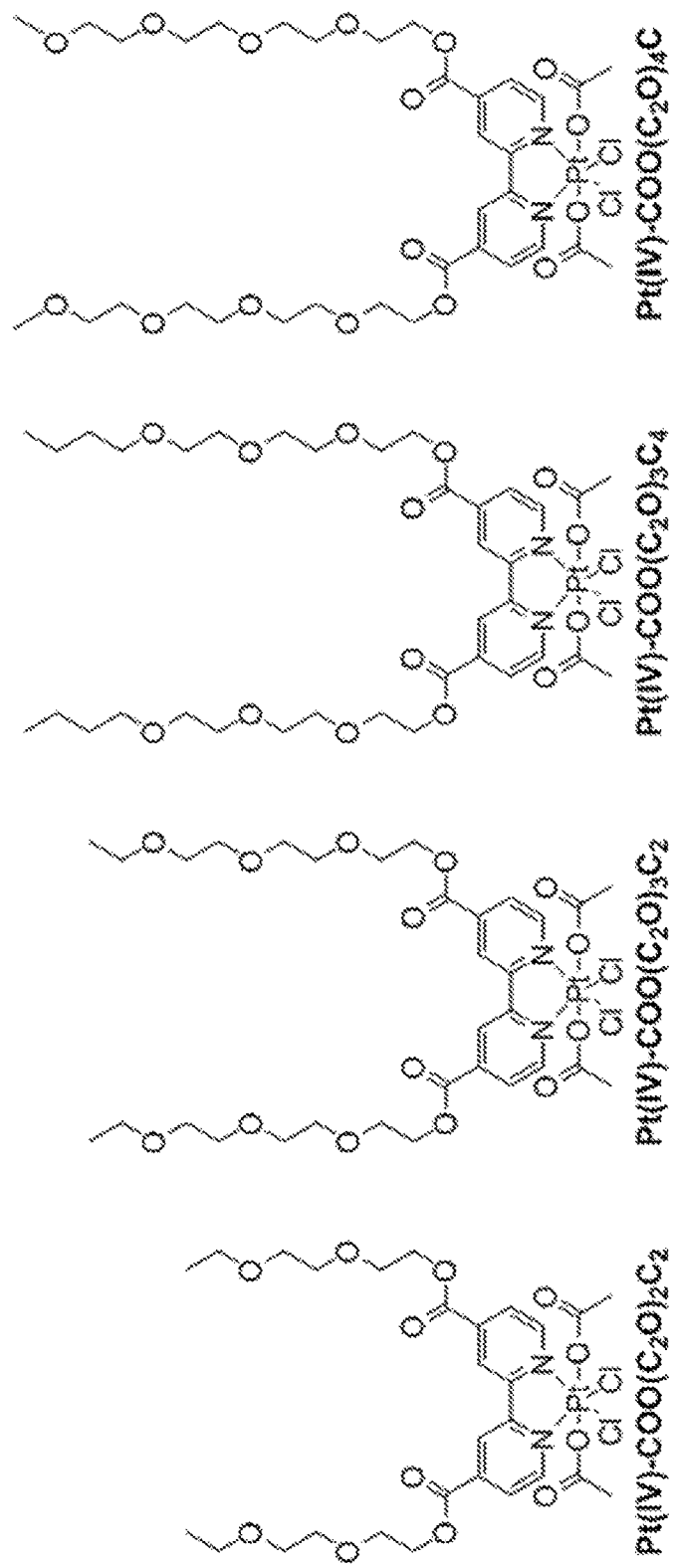

As described herein, the platinum complexes provided herein can be used to reduce the viability of cancer cells. FIG. 3 shows a series of Pt(II) complexes that were previously synthesized and tested for their potential use in cancer treatment, as described in U.S. Pat. No. 8,703,756. In vitro studies in various cancer cells indicated that these compounds are much more potent than cisplatin (Vo et al., *Metallomics* 5:973-987, 2013). One of these compounds, Pt(II)-4C, was tested in vivo in a mouse model to determine the maximum tolerated dose. Although the animals survived for seven days after intraperitoneal administration of the compound at a dose of 12.5 mg/kg/day for three days, the study was limited due to the compound's poor solubility in water and only moderate solubility in common organic solvents and solubilizing agents. Here, a series of Pt(IV) derivatives having improved solubility in DMSO and, in some instances, increased activity compared to their Pt(II) counterparts is described. Exemplary structures of these derivatives are shown in FIG. 5.

In some embodiments, the platinum complexes provided herein can have the general formula trans, cis-LPtCl$_2$(OAc)$_2$, where L is a 4,4'-disubstituted-2,2'-bipyridine compound with alkoxy or ester groups appended at the 4 and 4' positions of the bipyridine. This class of cisplatin analogs can maintain the original active sites of cisplatin (two Pt—Cl bonds in cis), and the appended alkyl chains can assist in binding to the major and minor DNA grooves (e.g., via secondary intermolecular interactions such as hydrogen bonding or electrostatic effects). Thus, replacement of the cisplatin amine ligands (NH$_3$) with functionalized imine ligands (2,2'-bipyridine) can afford the opportunity to retain the platinum binding site (for guanine and adenine) while incorporating new group extensions for interaction with the double helix walls in the major and minor grooves.

In some embodiments, a complex as provided herein can be of the general formula [Pt(IV)X$_2$AB(4,4'-bis[RO]-2,2'-bipyridine)], with a structure as shown in Formula (I):

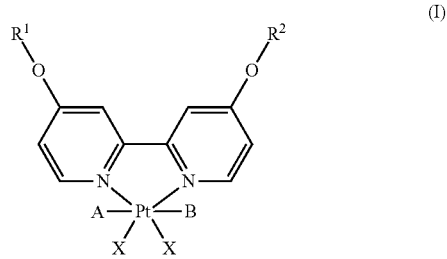

where $R^1$ and $R^2$ are independently selected from the group consisting of —$(CH_2)_nCH_3$, —$(CH_2)_nOCH_3$, and —$(CH_2)_n[O(CH_2)_m]_yO(CH_2)_zCH_3$, with n being an integer from 1 to 10, and each of m, y, and z independently being an integer from 0 to 10; where each X is independently Br, Cl, or I; and where A and B are independently selected from the group consisting of X, —OH, and —OC(O)$R^3$, where $R^3$ is —$(CH_2)_pCH_3$, and p is an integer from 0 to 10.

In some embodiments, a complex as provided herein can be of the general formula [Pt(IV)X$_2$AB(4,4'-bis[C(O)OR]-2,2'-bipyridine)], with a structure as shown in Formula (II):

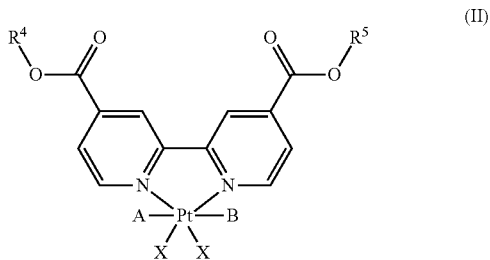

(II)

where $R^4$ and $R^5$ are independently selected from the group consisting of —$(CH_2)_tCH_3$, —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$, with t being an integer from 0 to 7; where each X is independently Br, Cl, or I; and where A and B are independently selected from the group consisting of X, —OH, and —OC(O)$R^3$, where $R^3$ is —$(CH_2)_pCH_3$, and p is an integer from 0 to 10.

Pt(IV) compounds are prodrugs, because they require activation through intracellular enzymatic reduction to Pt(II). In some cases, the use of Pt(IV) complexes as prodrugs can provide advantages over Pt(II) complexes. For example, Pt(IV) complexes have a low-spin $d_6$ octahedral geometry, rendering them more inert to substitution reactions than their Pt(II) counterparts. The decreased reactivity can lead to a reduction in side effects, and can provide the potential for oral administration. In addition, the added coordination of the axial ligands in Pt(IV) complexes can allow for greater flexibility in strategies that improve solubility and target selectivity. These advantages are not a given, however. In fact, a number of Pt(IV) compounds (e.g., cis-[Pt(NH$_3$)$_2$Cl$_4$], trans-[Pt(NH$_3$)$_2$Cl$_4$], [Pt(en)Cl$_4$], iproplatin, tetraplatin, and satraplatin; see, U.S. Pat. Nos. 4,177,263; 4,394,319; 4,845,124; 5,072,011; and 5,244,919) have been synthesized and found to be less effective and/or more toxic than Pt(II) compounds such as cisplatin.

1. Structure

In one aspect, a complex as provided herein can be of the general formula [Pt(IV)X$_2$AB(4,4'-bis[RO]-2,2'-bipyridine)], with a structure as shown in Formula (I):

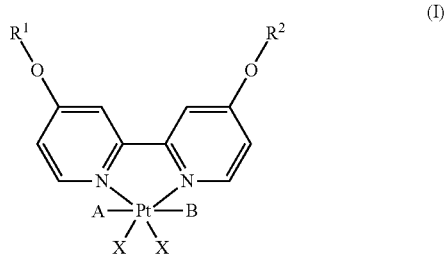

(I)

where $R^1$ and $R^2$ are independently selected from the group consisting of —$(CH_2)_nCH_3$, —$(CH_2)_nOCH_3$, and —$(CH_2)_n[O(CH_2)_m]_yO(CH_2)_zCH_3$, with n being an integer from 1 to 10, and each of m, y, and z independently being an integer from 0 to 10; where each X is independently Br, Cl, or I; and where A and B are independently selected from the group consisting of X, —OH, and —OC(O)$R^3$, where $R^3$ is —$(CH_2)_pCH_3$, and p is an integer from 0 to 10.

In one aspect, a complex as provided herein can be of the general formula [Pt(IV)X$_2$AB(4,4'-bis[C(O)OR]-2,2'-bipyridine)], with a structure as shown in Formula (II):

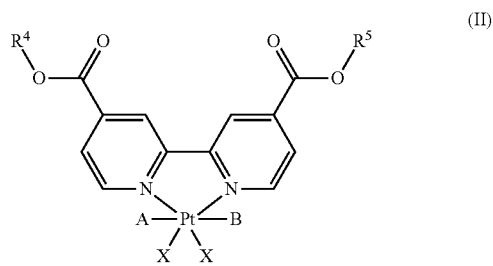

(II)

where $R^4$ and $R^5$ are independently selected from the group consisting of —$(CH_2)_tCH_3$, —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$, with t being an integer from 0 to 7; where each X is independently Br, Cl, or I; and where A and B are independently selected from the group consisting of X, —OH, and —OC(O)$R^3$, where $R^3$ is —$(CH_2)_pCH_3$, and p is an integer from 0 to 10.

In one aspect, complexes having a structure represented by a formula:

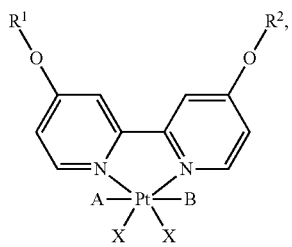

wherein each of $R^1$ and $R^2$ is independently selected from —$(CH_2)_nCH_3$, —$(CH_2)_nOCH_3$, and —$(CH_2)_n[O(CH_2)_m]_yO(CH_2)_zCH_3$; wherein n is selected from 1, 2, 3, 4, 5, 6, 7, 8, 9, and 10; wherein each of m, y, and z is independently selected from 0, 1, 2, 3, 4, 5, 6, 7, 8, 9, and 10; wherein each X is independently —Br, —Cl, or —I; and wherein each of A and B is independently selected from —Br, —Cl, —I, —OH, and —OC(O)$R^3$; wherein $R^3$ is —$(CH_2)_pCH_3$; and wherein p is selected from 0, 1, 2, 3, 4, 5, 6, 7, 8, 9, and 10, or a pharmaceutically acceptable derivative thereof are disclosed.

In one aspect, complexes having a structure represented by a formula selected from:

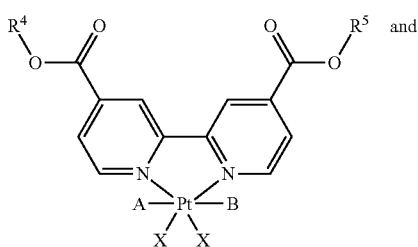

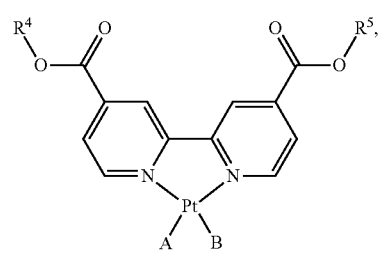

wherein each of $R^4$ and $R^5$ is independently selected from —$(CH_2)_tCH_3$, —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$; wherein t is selected from 0, 1, 2, 3, 4, 5, 6, and 7; wherein each X is independently —Br, —Cl, or —I; and wherein each of A and B is independently selected from —Br, —Cl, —I, —OH, and —OC(O)$R^3$, provided that A, B, and each X are not simultaneously —Br, simultaneously —Cl, or simultaneously —I; wherein $R^3$ is —$(CH_2)_pCH_3$; and wherein p is selected from 0, 1, 2, 3, 4, 5, 6, 7, 8, 9, and 10, or a pharmaceutically acceptable derivative thereof are disclosed.

In one aspect, complexes having a structure represented by a formula selected from:

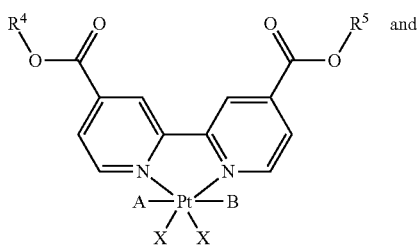

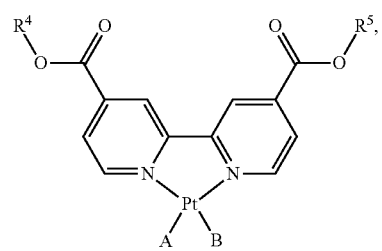

wherein each of $R^4$ and $R^5$ is independently selected from —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$; wherein t is selected from 0, 1, 2, 3, 4, 5, 6, and 7; wherein each X is independently —Br, —Cl, or —I; and wherein each of A and B is independently selected from —Br, —Cl, —I, —OH, and —OC(O)$R^3$; wherein $R^3$ is —$(CH_2)_pCH_3$; and wherein p is selected from 0, 1, 2, 3, 4, 5, 6, 7, 8, 9, and 10, or a pharmaceutically acceptable derivative thereof are disclosed.

In a further aspect, complex has a structure represented by a formula:

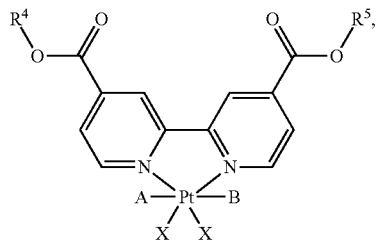

or a pharmaceutically acceptable derivative thereof.

In a further aspect, the complex has a structure represented by a formula:

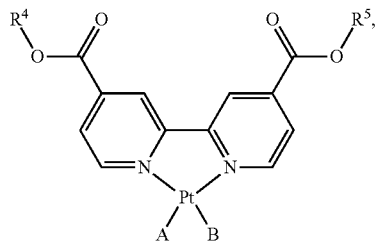

or a pharmaceutically acceptable derivative thereof.

In a further aspect, the complex has a structure represented by a formula selected from:

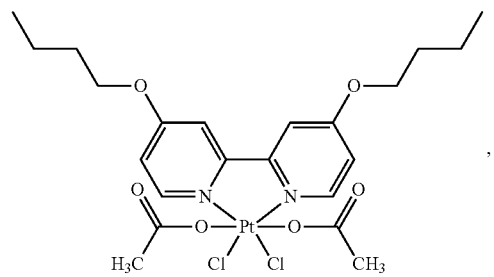

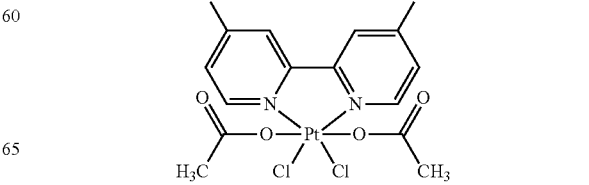

-continued

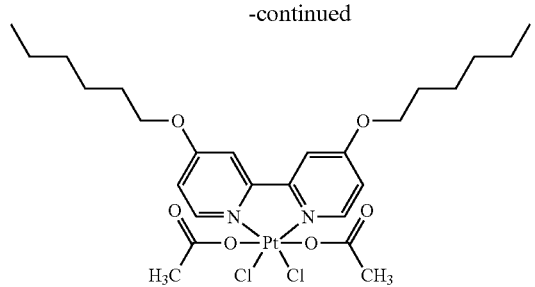

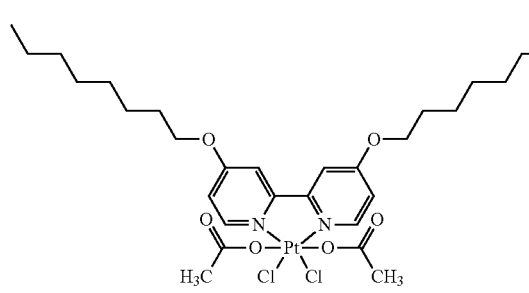

or a pharmaceutically acceptable derivative thereof.
In a further aspect, the complex is:

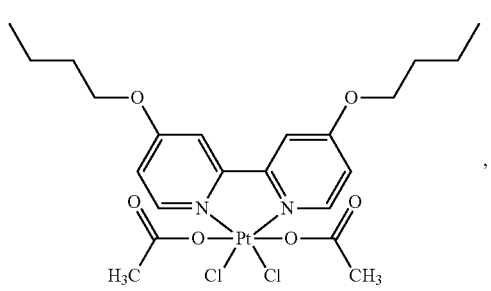

or a pharmaceutically acceptable derivative thereof.

In a further aspect, the complex is:

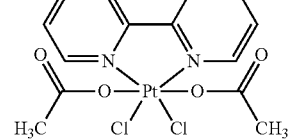, and

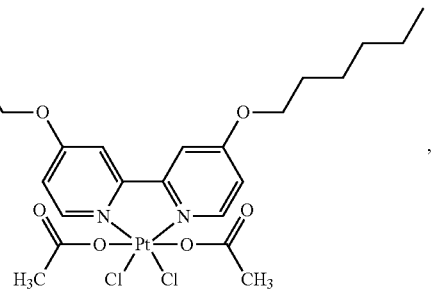

or a pharmaceutically acceptable derivative thereof.
In a further aspect, the complex is:

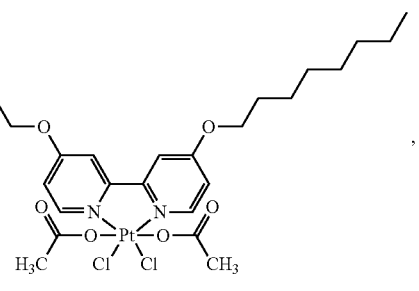

or a pharmaceutically acceptable derivative thereof.
In a further aspect, the complex has a structure represented by a formula selected from:

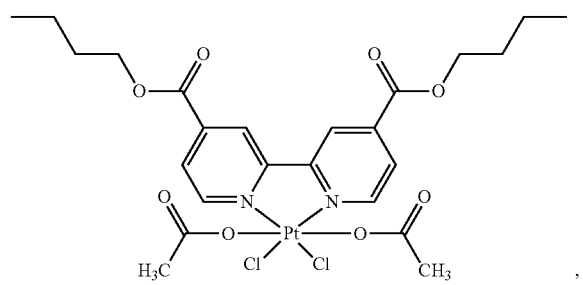

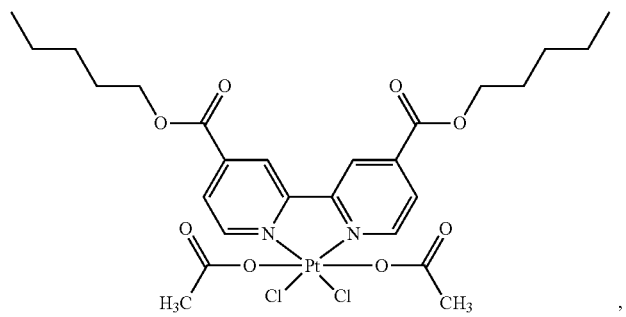
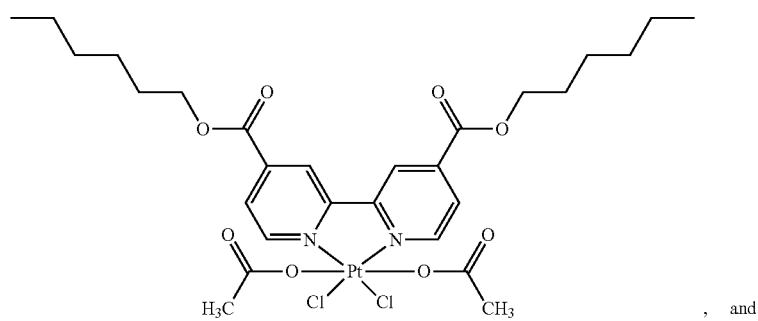
, and
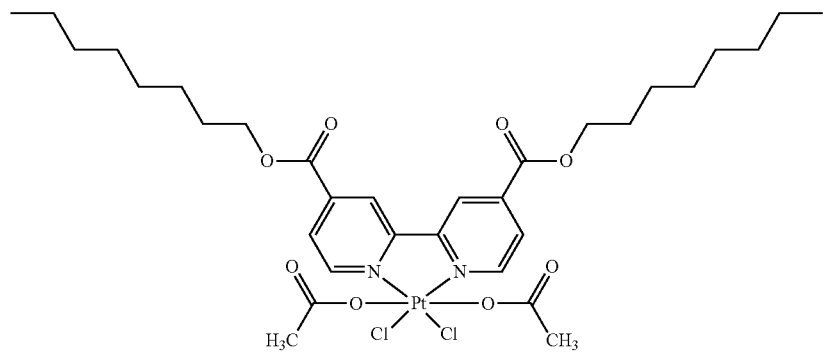
.
or a pharmaceutically acceptable derivative thereof.
In a further aspect, the complex is:
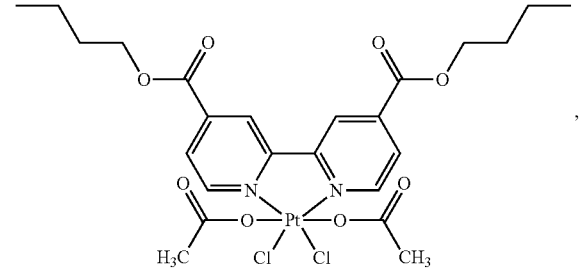
or a pharmaceutically acceptable derivative thereof.
In a further aspect, the complex is:
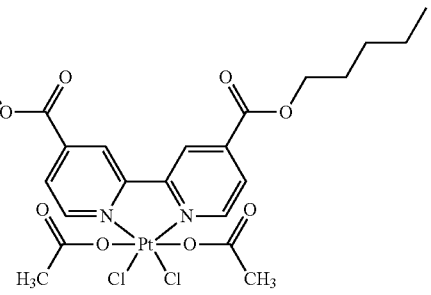
,
or a pharmaceutically acceptable derivative thereof.

In a further aspect, the complex is:

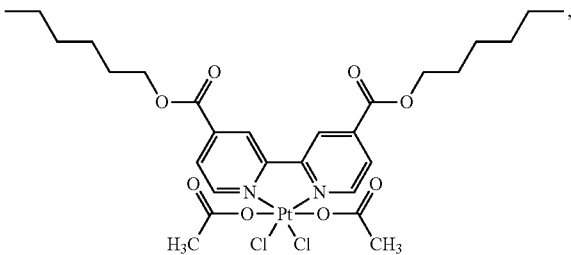

or a pharmaceutically acceptable derivative thereof.

In a further aspect, the complex is:

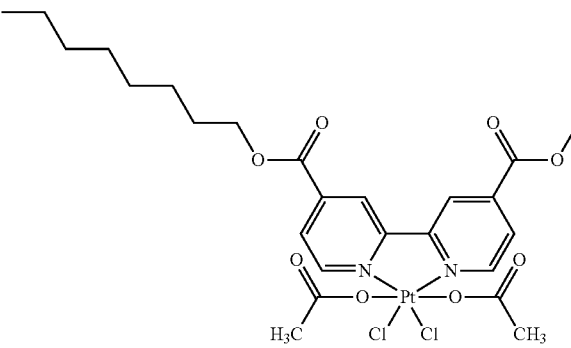

or a pharmaceutically acceptable derivative thereof.

In one aspect, n is an integer selected from 1, 2, 3, 4, 5, 6, 7, 8, 9, and 10. In a further aspect, n is an integer selected from 1, 2, 3, 4, 5, 6, 7, 8, and 9. In a still further aspect, n is an integer selected from 1, 2, 3, 4, 5, 6, 7, and 8. In yet a further aspect, n is an integer selected from 1, 2, 3, 4, 5, 6, and 7. In an even further aspect, n is an integer selected from 1, 2, 3, 4, 5, and 6. In a still further aspect, n is an integer selected from 1, 2, 3, 4, and 5. In yet a further aspect, n is an integer selected from 1, 2, 3, and 4. In an even further aspect, n is an integer selected from 1, 2, and 3. In a still further aspect, n is an integer selected from 1 and 2. In yet a further aspect, n is 10. In an even further aspect, n is 9. In a still further aspect, n is 8. In yet a further aspect, n is 7. In an even further aspect, n is 6. In a still further aspect, n is 5. In yet a further aspect, n is 4. In an even further aspect, n is 3. In a still further aspect, n is 2. In yet a further aspect, n is 1.

In one aspect, each of m, y, and z are an integer independently selected from 0, 1, 2, 3, 4, 5, 6, 7, 8, 9, and 10. In a further aspect, each of m, y, and z are an integer independently selected from 0, 1, 2, 3, 4, 5, 6, 7, 8, and 9. In a still further aspect, each of m, y, and z are an integer independently selected from 0, 1, 2, 3, 4, 5, 6, 7, and 8. In yet a further aspect, each of m, y, and z are an integer independently selected from 0, 1, 2, 3, 4, 5, 6, and 7. In an even further aspect, each of m, y, and z are an integer independently selected from 0, 1, 2, 3, 4, 5, and 6. In a still further aspect, each of m, y, and z are an integer independently selected from 0, 1, 2, 3, 4, and 5. In yet a further aspect, each of m, y, and z are an integer independently selected from 0, 1, 2, 3, and 4. In an even further aspect, each of m, y, and z are an integer independently selected from 0, 1, 2, and 3. In a still further aspect, each of m, y, and z are an integer independently selected from 0, 1, and 2. In yet a further aspect, each of m, y, and z are an integer independently selected from 0 and 1. In an even further aspect, each of m, y, and z are 10. In a still further aspect, each of m, y, and z are 9. In yet a further aspect, each of m, y, and z are 8. In a still further aspect, each of m, y, and z are 7. In yet a further aspect, each of m, y, and z are 6. In an even further aspect, each of m, y, and z are 5. In a still further aspect, each of m, y, and z are 4. In yet a further aspect, each of m, y, and z are 3. In an even further aspect, each of m, y, and z are 2. In a still further aspect, each of m, y, and z are 1. In yet a further aspect, each of m, y, and z are 0.

In one aspect, p is an integer selected from 0, 1, 2, 3, 4, 5, 6, 7, 8, 9, and 10. In a still further aspect, p is an integer selected from 0, 1, 2, 3, 4, 5, 6, 7, 8, and 9. In yet a further aspect, p is an integer selected from 0, 1, 2, 3, 4, 5, 6, 7, and 8. In an even further aspect, p is an integer selected from 0, 1, 2, 3, 4, 5, 6, and 7. In a still further aspect, p is an integer selected from 0, 1, 2, 3, 4, 5, and 6. In yet a further aspect, p is an integer selected from 0, 1, 2, 3, 4, and 5. In an even further aspect, p is an integer selected from 0, 1, 2, 3, and 4. In a still further aspect, p is an integer selected from 0, 1, 2, and 3. In yet a further aspect, p is an integer selected from 0, 1, and 2. In an even further aspect, p is an integer selected from 0 and 1. In a still further aspect, p is 10. In yet a further aspect, p is 9. In an even further aspect, p is 8. In a still further aspect, p is 7. In yet a further aspect, p is 6. In an even further aspect, p is 5. In a still further aspect, p is 4. In yet a further aspect, p is 3. In an even further aspect, p is 2. In a still further aspect, p is 1. In yet a further aspect, p is 0.

In one aspect, t is an integer selected from 0, 1, 2, 3, 4, 5, 6, and 7. In a further aspect, t is an integer selected from 0, 1, 2, 3, 4, 5, and 6. In a still further aspect, t is an integer selected from 0, 1, 2, 3, 4, and 5. In yet a further aspect, t is an integer selected from 0, 1, 2, 3, and 4. In an even further aspect, t is an integer selected from 0, 1, 2, and 3. In a still further aspect, t is an integer selected from 0, 1, and 2. In yet a further aspect, t is an integer selected from 0 and 1. In an even further aspect, t is 7. In a still further aspect, t is 6. In yet a further aspect, t is 5. In an even further aspect, t is 4. In a still further aspect, t is 3. In yet a further aspect, t is 2. In an even further aspect, t is 1. In a still further aspect, t is 0.

a. A and B Groups

In one aspect, each of A and B is independently selected from the group consisting of X, —OH, and —OC(O)$R^3$. In a further aspect, each of A and B is independently selected from the group consisting of —Br, —Cl, —I, —OH, and —OC(O)$R^3$.

In a further aspect, each of A and B is independently selected from the group consisting of —Br, —Cl, —I, and —OH. In a still further aspect, each of A and B is independently selected from the group consisting of —Br, —Cl, and —OH. In yet a further aspect, each of A and B is independently selected from the group consisting of —Cl and —OH.

In a further aspect, each of A and B is independently selected from the group consisting of —Br, —Cl, and —I. In a still further aspect, each of A and B is independently selected from the group consisting of —Br and —Cl. In yet a further aspect, each of A and B is independently selected from the group consisting of —Br and —I. In an even further aspect, each of A and B is independently selected from the group consisting of —I and —Cl. In a still further aspect, each of A and B is —I. In yet a further aspect, each of A and B is —Br. In an even further aspect, each of A and B is —Cl.

In a further aspect, each of A and B is independently selected from the group consisting of —OH and —OC(O)$R^3$. In a still further aspect, each of A and B is —OH. In yet a further aspect, each of A and B is —OC(O)$R^3$.

b. X Groups

In one aspect, each X is independently Br, Cl, or I. In a further aspect, each X is independently Br or Cl. In a still further aspect, each X is independently Br or I. In yet a further aspect, each X is independently Cl or I. In an even further aspect, each X is Br. In a still further aspect, each X is Cl. In yet a further aspect, each X is I.

c. $R^1$ and $R^2$ Groups

In one aspect, $R^1$ and $R^2$ is independently selected from the group consisting of —$(CH_2)_nCH_3$, —$(CH_2)_nOCH_3$, and —$(CH_2)_n[O(CH_2)_m]_yO(CH_2)_zCH_3$. In a further aspect, $R^1$ and $R^2$ are independently selected from the group consisting of —$(CH_2)_nCH_3$ and —$(CH_2)_nOCH_3$. In a still further aspect, $R^1$ and $R^2$ is independently selected from the group consisting of —$(CH_2)_nCH_3$ and —$(CH_2)_n[O(CH_2)_m]_yO(CH_2)_zCH_3$. In yet a further aspect, $R^1$ and $R^2$ is independently selected from the group consisting of —$(CH_2)_nOCH_3$, and —$(CH_2)_n[O(CH_2)_m]_yO(CH_2)_zCH_3$. In an even further aspect, each of $R^1$ and $R^2$ is —$(CH_2)_nOCH_3$. In a still further aspect, each of $R^1$ and $R^2$ is —$(CH_2)_nOCH_3$. In yet a further aspect, each of $R^1$ and $R^2$ is —$(CH_2)_n[O(CH_2)_m]_yO(CH_2)_zCH_3$. In an even further aspect, each of $R^1$ and $R^2$ is —$(CH_2)_nCH_3$.

In a further aspect, $R^1$ is —$(CH_2)_nCH_3$ and $R^2$ is selected from the group consisting of —$(CH_2)_nCH_3$, —$(CH_2)_n CH_3$, and —$(CH_2)_n[O(CH_2)_m]_yO(CH_2)_zCH_3$. In a still further aspect, $R^1$ is —$(CH_2)_nCH_3$ and $R^2$ is selected from the group consisting of —$(CH_2)_nOCH_3$ and —$(CH_2)_n[O(CH_2)_m]_yO(CH_2)_zCH_3$. In yet a further aspect, $R^1$ is —$(CH_2)_n CH_3$ and $R^2$ is —$(CH_2)_nOCH_3$. In an even further aspect, $R^1$ is —$(CH_2)_nCH_3$ and $R^2$ is —$(CH_2)_n[O(CH_2)_m]_yO(CH_2)_z CH_3$.

In a further aspect, $R^1$ is —$(CH_2)_nOCH_3$ and $R^2$ is selected from the group consisting of —$(CH_2)_nCH_3$, —$(CH_2)_nOCH_3$, and —$(CH_2)_n[O(CH_2)_m]_yO(CH_2)_zCH_3$. In a still further aspect, $R^1$ is —$(CH_2)_nOCH_3$ and $R^2$ is selected from the group consisting of —$(CH_2)_nCH_3$ and —$(CH_2)_n[O(CH_2)_m]_yO(CH_2)_zCH_3$. In yet a further aspect, $R^1$ is —$(CH_2)_nOCH_3$ and $R^2$ is —$(CH_2)_nCH_3$. In an even further aspect, $R^1$ is —$(CH_2)_nOCH_3$ and $R^2$ is —$(CH_2)_n[O(CH_2)_m]_yO(CH_2)_zCH_3$.

In a further aspect, $R^1$ is —$(CH_2)_n[O(CH_2)_m]_yO(CH_2)_zCH_3$ and $R^2$ is selected from the group consisting of —$(CH_2)_n CH_3$, —$(CH_2)_nOCH_3$, and —$(CH_2)_n[O(CH_2)_m]_yO(CH_2)_zCH_3$. In a still further aspect, $R^1$ is —$(CH_2)_n[O(CH_2)_m]_yO(CH_2)_zCH_3$ and $R^2$ is selected from the group consisting of —$(CH_2)_nCH_3$ and —$(CH_2)_nOCH_3$. In yet a further aspect, $R^1$ is —$(CH_2)_n[O(CH_2)_m]_yO(CH_2)_zCH_3$ and $R^2$ is —$(CH_2)_nCH_3$. In an even further aspect, $R^1$ is —$(CH_2)_n[O(CH_2)_m]_yO(CH_2)_zCH_3$ and $R^2$ is —$(CH_2)_nOCH_3$.

d. $R^3$ Groups

In one aspect, $R^3$ is —$(CH_2)_pCH_3$. In a further aspect, $R^3$ is —$(CH_2)_{0-10}CH_3$. In a still further aspect, $R^3$ is selected from methyl, ethyl, n-propyl, n-butyl, n-pentyl, n-hexyl, n-heptyl, and n-octyl. In yet a further aspect, $R^3$ is selected from methyl, ethyl, n-propyl, n-butyl, n-pentyl, n-hexyl, and n-heptyl. In an even further aspect, $R^3$ is selected from methyl, ethyl, n-propyl, n-butyl, n-pentyl, and n-hexyl. In a still further aspect, $R^3$ is selected from methyl, ethyl, n-propyl, n-butyl, and n-pentyl. In yet a further aspect, $R^3$ is selected from methyl, ethyl, n-propyl, and n-butyl. In an even further aspect, $R^3$ is selected from methyl, ethyl, and n-propyl.

e. $R^4$ and $R^5$ Groups

In one aspect, $R^4$ and $R^5$ are independently selected from the group consisting of —$(CH_2)_tCH_3$, —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In a further aspect, $R^4$ and $R^5$ are independently selected from the group consisting of —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In a still further aspect, $R^4$ and $R^5$ are independently selected from the group consisting of —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In yet a further aspect, $R^4$ and $R^5$ are independently selected from the group consisting of —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In an even further aspect, $R^4$ and $R^5$ are independently selected from the group consisting of —$(CH_2CH_2O)_3CH_2CH_3$, —$(CH_2CH_2O)_3(CH_2)_3CH_3$, and —$(CH_2CH_2O)_4CH_3$. In a still further aspect, $R^4$ and $R^5$ are independently selected from the group consisting of —$(CH_2CH_2O)_3(CH_2)_3CH_3$ and —$(CH_2CH_2O)_4CH_3$. In yet a further aspect, each of $R^4$ and $R^5$ are —$(CH_2)_tCH_3$. In an even further aspect, each of $R^4$ and $R^5$ are —$C(CH_3)_3$. In a still further aspect, each of $R^4$ and $R^5$ are —$CH_2CH(CH_2CH_3)CH_2CH_2CH_2CH_3$. In yet a further aspect, each of $R^4$ and $R^5$ are —$(CH_2CH_2O)_2CH_2CH_3$. In an even further aspect, each of $R^4$ and $R^5$ are —$(CH_2CH_2O)_3CH_2CH_3$. In a still further aspect, each of $R^4$ and $R^5$ are —$(CH_2CH_2O)_3(CH_2)_3CH_3$. In yet a further aspect, each of $R^4$ and $R^5$ are —$(CH_2CH_2O)_4CH_3$.

In a further aspect, $R^4$ is —$(CH_2)_tCH_3$ and $R^5$ is selected from the group consisting of —$(CH_2)_tCH_3$, —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In a still further aspect, $R^4$ is —$(CH_2)_tCH_3$ and $R^5$ is selected from the group consisting of —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In yet a further aspect, $R^4$ is —$(CH_2)_tCH_3$ and $R^5$ is selected from the group consisting of —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In an even further aspect, $R^4$ is —$(CH_2)_tCH_3$ and $R^5$ is selected from the group consisting of —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In a still further aspect, $R^4$ is —$(CH_2)_tCH_3$ and $R^5$ is selected from the group consisting of —$(CH_2CH_2O)_3CH_2CH_3$, —(CH$_2$CH$_2$O)$_3$(CH$_2$)$_3$CH$_3$, and —(CH$_2$CH$_2$O)$_4$CH$_3$. In yet a further aspect, R$^4$ is —(CH$_2$)$_t$CH$_3$ and R$^5$ is selected from the group consisting of —(CH$_2$CH$_2$O)$_3$(CH$_2$)$_3$CH$_3$ and —(CH$_2$CH$_2$O)$_4$CH$_3$. In an even further aspect, R$^4$ is —(CH$_2$)$_t$CH$_3$ and R$^5$ is —(CH$_2$CH$_2$O)$_2$CH$_2$CH$_3$. In a still further aspect, R$^4$ is —(CH$_2$)$_t$CH$_3$ and R$^5$ is —(CH$_2$CH$_2$O)$_3$CH$_2$CH$_3$. In yet a further aspect, R$^4$ is —(CH$_2$)$_t$CH$_3$ and R$^5$ is —(CH$_2$CH$_2$O)$_3$(CH$_2$)$_3$CH$_3$. In an even further aspect, R$^4$ is —(CH$_2$)$_t$CH$_3$ and R$^5$ is —(CH$_2$CH$_2$O)$_4$CH$_3$.

In a further aspect, R$^4$ is —C(CH$_3$)$_3$ and R$^5$ is selected from the group consisting of —(CH$_2$)$_t$CH$_3$, —C(CH$_3$)$_3$, —CH$_2$CH(CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In a still further aspect, R$^4$ is —C(CH$_3$)$_3$ and R$^5$ is selected from the group consisting of —C(CH$_3$)$_3$, —CH$_2$CH(CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In yet a further aspect, R$^4$ is —C(CH$_3$)$_3$ and R$^5$ is selected from the group consisting of —CH$_2$CH(CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In an even further aspect, R$^4$ is —C(CH$_3$)$_3$ and R$^5$ is selected from the group consisting of —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In a still further aspect, R$^4$ is —C(CH$_3$)$_3$ and R$^5$ is selected from the group consisting of —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In yet a further aspect, R$^4$ is —C(CH$_3$)$_3$ and R$^5$ is selected from the group consisting of —(CH$_2$CH$_2$O)$_3$(CH$_2$)$_3$CH$_3$ and —(CH$_2$CH$_2$O)$_4$CH$_3$. In an even further aspect, R$^4$ is —C(CH$_3$)$_3$ and R$^5$ is —(CH$_2$CH$_2$O)$_2$CH$_2$CH$_3$. In a still further aspect, R$^4$ is —C(CH$_3$)$_3$ and R$^5$ is —(CH$_2$CH$_2$O)$_3$CH$_2$CH$_3$. In yet a further aspect, R$^4$ is —C(CH$_3$)$_3$ and R$^5$ is —(CH$_2$CH$_2$O)$_3$(CH$_2$)$_3$CH$_3$. In an even further aspect, R$^4$ is —C(CH$_3$)$_3$ and R$^5$ is —(CH$_2$CH$_2$O)$_4$CH$_3$.

In a further aspect, R$^4$ is —CH$_2$CH(CH$_2$CH$_3$)CH$_2$CH$_2$CH$_2$CH$_3$ and R$^5$ is selected from the group consisting of —(CH$_2$)$_t$CH$_3$, —C(CH$_3$)$_3$, —CH$_2$CH(CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$ CH$_2$CH$_3$, —(CH$_2$CH$_2$O)$_3$(CH$_2$)$_3$CH$_3$, and —(CH$_2$CH$_2$O)$_4$ CH$_3$. In a still further aspect, R$^4$ is —CH$_2$CH(CH$_2$CH$_3$)CH$_2$CH$_2$CH$_2$CH$_3$ and R$^5$ is selected from the group consisting of —C(CH$_3$)$_3$, —CH$_2$CH (CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$ CH$_2$CH$_3$, —(CH$_2$CH$_2$O)$_3$(CH$_2$)$_3$CH$_3$, and —(CH$_2$CH$_2$O)$_4$ CH$_3$. In yet a further aspect, R$^4$ is —CH$_2$CH(CH$_2$CH$_3$)CH$_2$CH$_2$CH$_2$CH$_3$ and R$^5$ is selected from the group consisting of —CH$_2$CH(CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In an even further aspect, R$^4$ is —CH$_2$CH(CH$_2$CH$_3$)CH$_2$CH$_2$CH$_2$CH$_3$ and R$^5$ is selected from the group consisting of —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In a still further aspect, R$^4$ is —CH$_2$CH(CH$_2$CH$_3$)CH$_2$CH$_2$CH$_2$CH$_3$ and R$^5$ is selected from the group consisting of —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In yet a further aspect, R$^4$ is —CH$_2$CH(CH$_2$CH$_3$)CH$_2$CH$_2$CH$_2$CH$_3$ and R$^5$ is selected from the group consisting of —(CH$_2$CH$_2$O)$_3$(CH$_2$)$_3$CH$_3$ and —(CH$_2$CH$_2$O)$_4$CH$_3$. In an even further aspect, R$^4$ is —CH$_2$CH(CH$_2$CH$_3$)CH$_2$CH$_2$CH$_2$CH$_3$ and R$^5$ is —(CH$_2$CH$_2$O)$_3$(CH$_2$)$_3$CH$_3$. In an even further aspect, R$^4$ is —CH$_2$CH(CH$_2$CH$_3$)CH$_2$CH$_2$CH$_2$CH$_3$ and R$^5$ is —(CH$_2$CH$_2$O)$_4$CH$_3$.

In a further aspect, R$^4$ is —(CH$_2$CH$_2$O)$_2$CH$_2$CH$_3$ and R$^5$ is selected from the group consisting of —(CH$_2$)$_t$CH$_3$, —C(CH$_3$)$_3$, —CH$_2$CH(CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In a still further aspect, R$^4$ is —(CH$_2$CH$_2$O)$_2$CH$_2$CH$_3$ and R$^5$ is selected from the group consisting of —C(CH$_3$)$_3$, —CH$_2$CH (CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In yet a further aspect, R$^4$ is —(CH$_2$CH$_2$O)$_2$CH$_2$CH$_3$ and R$^5$ is selected from the group consisting of —CH$_2$CH(CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In an even further aspect, R$^4$ is —(CH$_2$CH$_2$O)$_2$CH$_2$CH$_3$ and R$^5$ is selected from the group consisting of —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In a still further aspect, R$^4$ is —(CH$_2$CH$_2$O)$_2$CH$_2$CH$_3$ and R$^5$ is selected from the group consisting of —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In yet a further aspect, R$^4$ is —(CH$_2$CH$_2$O)$_2$CH$_2$CH$_3$ and R$^5$ is selected from the group consisting of —(CH$_2$CH$_2$O)$_3$(CH$_2$)$_3$CH$_3$ and —(CH$_2$CH$_2$O)$_4$CH$_3$. In an even further aspect, R$^4$ is —(CH$_2$CH$_2$O)$_2$CH$_2$CH$_3$ and R$^5$ is —(CH$_2$CH$_2$O)$_2$CH$_2$CH$_3$. In a still further aspect, R$^4$ is —(CH$_2$CH$_2$O)$_2$CH$_2$CH$_3$ and R$^5$ is —(CH$_2$CH$_2$O)$_3$(CH$_2$)$_3$CH$_3$. In an even further aspect, R$^4$ is —(CH$_2$CH$_2$O)$_2$CH$_2$CH$_3$ and R$^5$ is —(CH$_2$CH$_2$O)$_4$CH$_3$.

In a further aspect, R$^4$ is —(CH$_2$CH$_2$O)$_3$CH$_2$CH$_3$ and R$^5$ is selected from the group consisting of —(CH$_2$)$_t$CH$_3$, —C(CH$_3$)$_3$, —CH$_2$CH(CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In a still further aspect, R$^4$ is —(CH$_2$CH$_2$O)$_3$CH$_2$CH$_3$ and R$^5$ is selected from the group consisting of —C(CH$_3$)$_3$, —CH$_2$CH (CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In yet a further aspect, R$^4$ is —(CH$_2$CH$_2$O)$_3$CH$_2$CH$_3$ and R$^5$ is selected from the group consisting of —CH$_2$CH(CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In an even further aspect, R$^4$ is —(CH$_2$CH$_2$O)$_3$CH$_2$CH$_3$ and R$^5$ is selected from the group consisting of —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In a still further aspect, R$^4$ is —(CH$_2$CH$_2$O)$_3$CH$_2$CH$_3$ and R$^5$ is selected from the group consisting of —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In yet a further aspect, R$^4$ is —(CH$_2$CH$_2$O)$_3$CH$_2$CH$_3$ and R$^5$ is selected from the group consisting of —(CH$_2$CH$_2$O)$_3$(CH$_2$)$_3$CH$_3$ and —(CH$_2$CH$_2$O)$_4$CH$_3$. In an even further aspect, R$^4$ is —(CH$_2$CH$_2$O)$_3$CH$_2$CH$_3$ and R$^5$ is —(CH$_2$CH$_2$O)$_2$CH$_2$CH$_3$. In a still further aspect, R$^4$ is —(CH$_2$CH$_2$O)$_3$CH$_2$CH$_3$ and R$^5$ is —(CH$_2$CH$_2$O)$_3$(CH$_2$)$_3$CH$_3$. In an even further aspect, R$^4$ is —(CH$_2$CH$_2$O)$_3$CH$_2$CH$_3$ and R$^5$ is —(CH$_2$CH$_2$O)$_4$CH$_3$.

In a further aspect, R$^4$ is —(CH$_2$CH$_2$O)$_3$(CH$_2$)$_3$CH$_3$ and R$^5$ is selected from the group consisting of —(CH$_2$)$_t$CH$_3$, —C(CH$_3$)$_3$, —CH$_2$CH(CH$_2$CH$_3$)CH$_2$CH$_2$CH$_2$CH$_3$, —(CH$_2$CH$_2$O)$_2$CH$_2$CH$_3$, —(CH$_2$CH$_2$O)$_3$CH$_2$CH$_3$, —(CH$_2$CH$_2$O)$_3$(CH$_2$)$_3$CH$_3$, and —(CH$_2$CH$_2$O)$_4$CH$_3$. In a still further aspect, $R^4$ is —$(CH_2CH_2O)_3(CH_2)_3CH_3$ and $R^5$ is selected from the group consisting of —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In yet a further aspect, $R^4$ is —$(CH_2CH_2O)_3(CH_2)_3CH_3$ and $R^5$ is selected from the group consisting of —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In an even further aspect, $R^4$ is —$(CH_2CH_2O)_3(CH_2)_3CH_3$ and $R^5$ is selected from the group consisting of —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In a still further aspect, $R^4$ is —$(CH_2CH_2O)_3(CH_2)_3CH_3$ and $R^5$ is selected from the group consisting of —$(CH_2CH_2O)_3CH_2CH_3$, —$(CH_2CH_2O)_3(CH_2)_3CH_3$, and —$(CH_2CH_2O)_4CH_3$. In yet a further aspect, $R^4$ is —$(CH_2CH_2O)_3(CH_2)_3CH_3$ and $R^5$ is selected from the group consisting of —$(CH_2CH_2O)_3(CH_2)_3CH_3$ and —$(CH_2CH_2O)_4CH_3$. In an even further aspect, $R^4$ is —$(CH_2CH_2O)_3(CH_2)_3CH_3$ and $R^5$ is —$(CH_2CH_2O)_2CH_2CH_3$. In a still further aspect, $R^4$ is —$(CH_2CH_2O)_3(CH_2)_3CH_3$ and $R^5$ is —$(CH_2CH_2O)_3CH_2CH_3$. In yet a further aspect, $R^4$ is —$(CH_2CH_2O)_3(CH_2)_3CH_3$ and $R^5$ is —$(CH_2CH_2O)_4CH_3$.

In a further aspect, $R^4$ is —$(CH_2CH_2O)_4CH_3$ and $R^5$ is selected from the group consisting of —$(CH_2)_tCH_3$, —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In a still further aspect, $R^4$ is —$(CH_2CH_2O)_4CH_3$ and $R^5$ is selected from the group consisting of —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In yet a further aspect, $R^4$ is —$(CH_2CH_2O)_4CH_3$ and $R^5$ is selected from the group consisting of —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In an even further aspect, $R^4$ is —$(CH_2CH_2O)_4CH_3$ and $R^5$ is selected from the group consisting of —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$. In a still further aspect, $R^4$ is —$(CH_2CH_2O)_4CH_3$ and $R^5$ is selected from the group consisting of —$(CH_2CH_2O)_3CH_2CH_3$, —$(CH_2CH_2O)_3(CH_2)_3CH_3$, and —$(CH_2CH_2O)_4CH_3$. In yet a further aspect, $R^4$ is —$(CH_2CH_2O)_4CH_3$ and $R^5$ is selected from the group consisting of —$(CH_2CH_2O)_3(CH_2)_3CH_3$ and —$(CH_2CH_2O)_4CH_3$. In an even further aspect, $R^4$ is —$(CH_2CH_2O)_4CH_3$ and $R^5$ is —$(CH_2CH_2O)_2CH_2CH_3$. In a still further aspect, $R^4$ is —$(CH_2CH_2O)_4CH_3$ and $R^5$ is —$(CH_2CH_2O)_3CH_2CH_3$. In yet a further aspect, $R^4$ is —$(CH_2CH_2O)_4CH_3$ and $R^5$ is —$(CH_2CH_2O)_3(CH_2)_3CH_3$.

2. Example Complexes

In one aspect, disclosed are platinum complexes having a structure selected from:

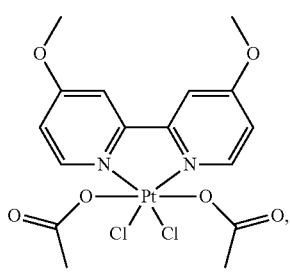

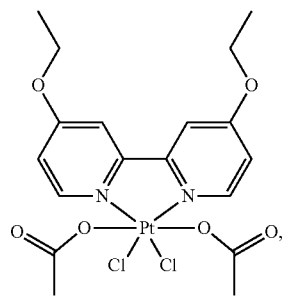

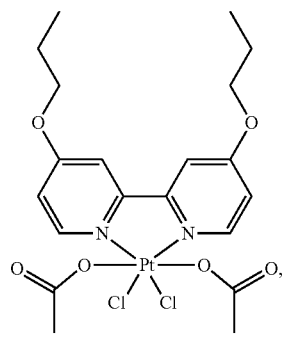

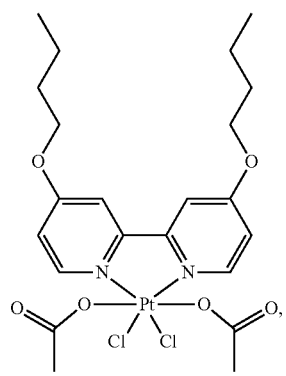

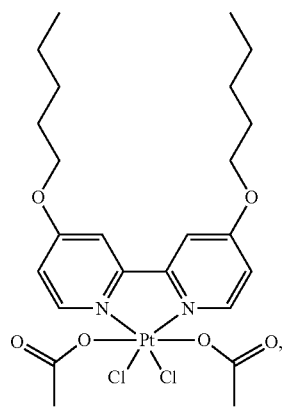

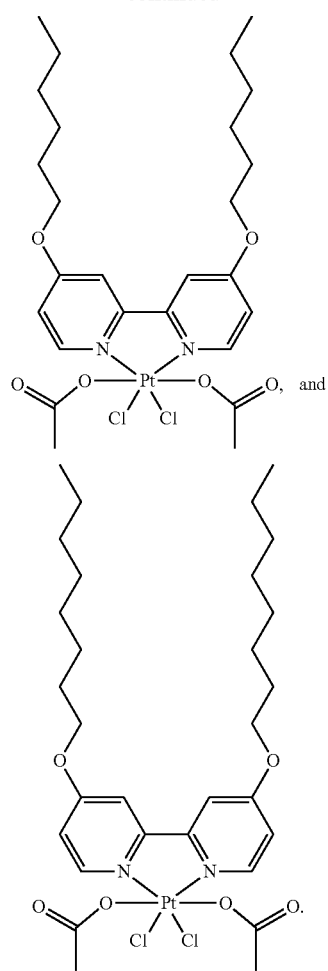
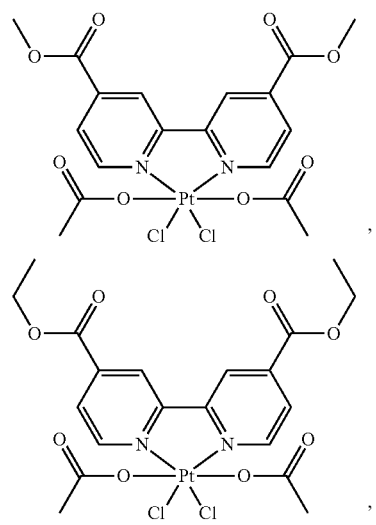
3. Prophetic Example Complexes
In one aspect, disclosed are platinum complexes having a structure selected from:
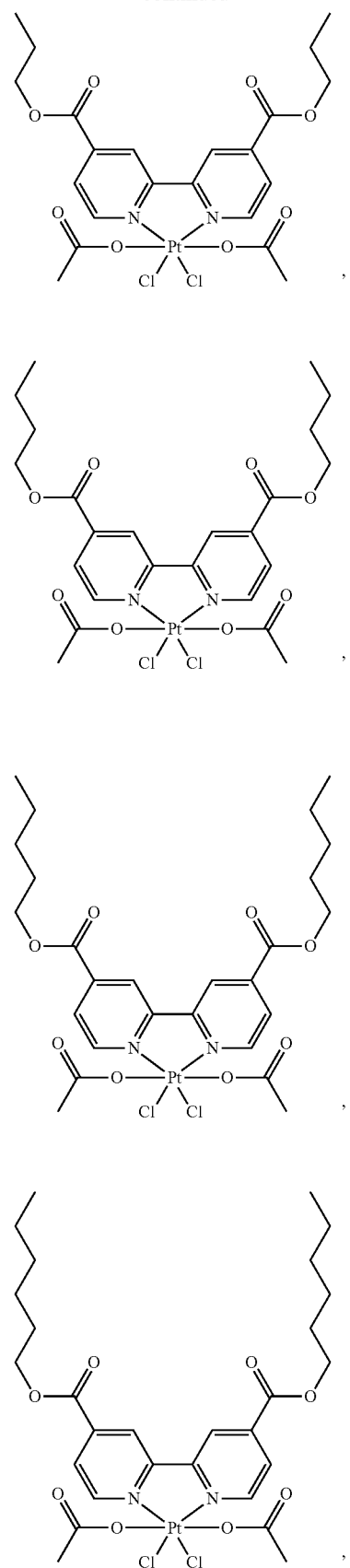

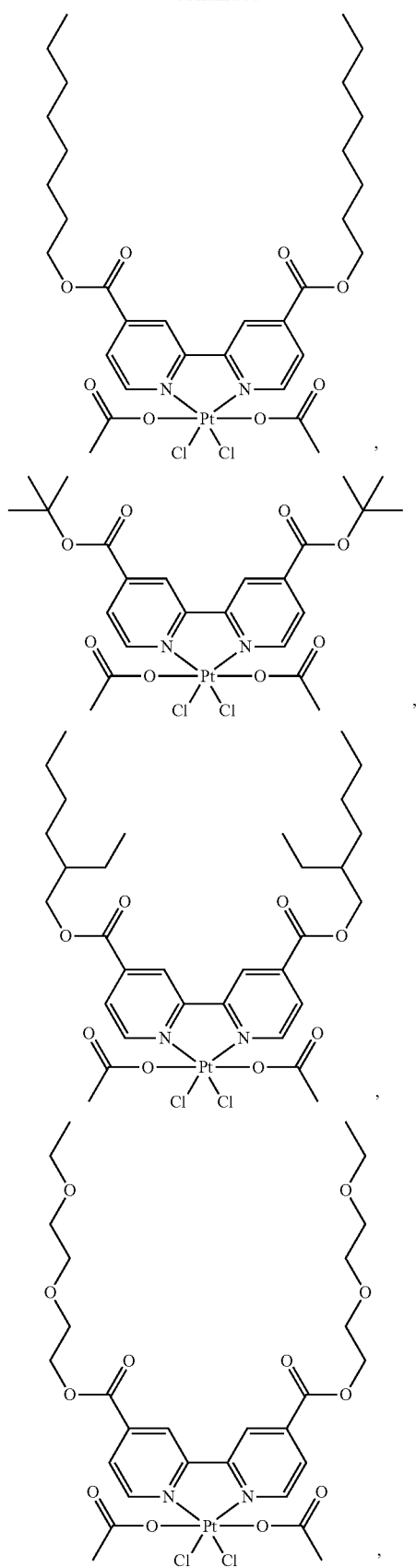
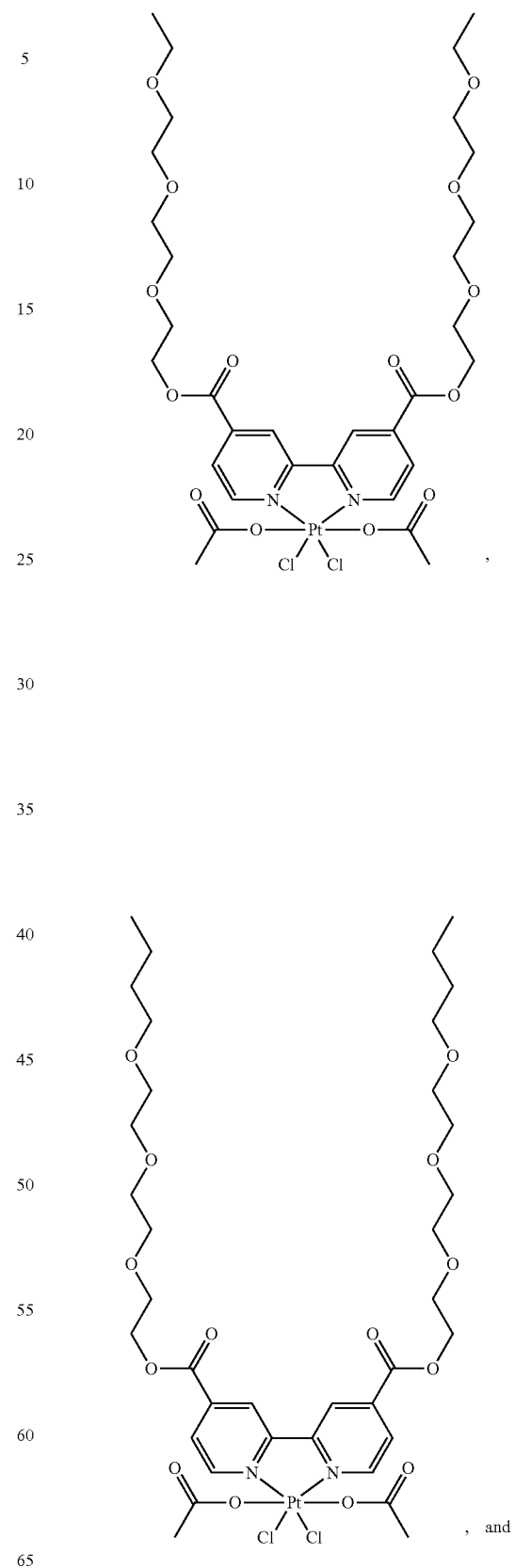

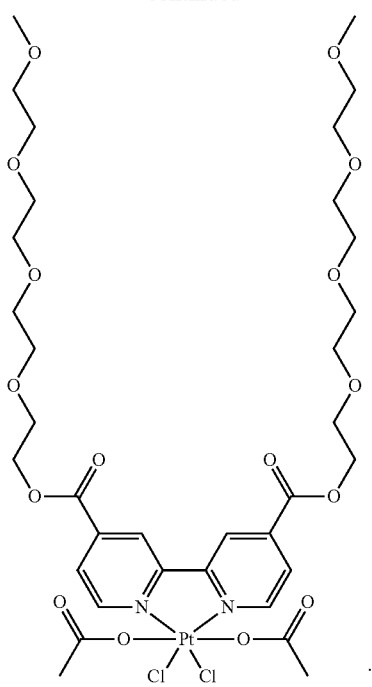
In a further aspect, disclosed are platinum complexes having a structure selected from:
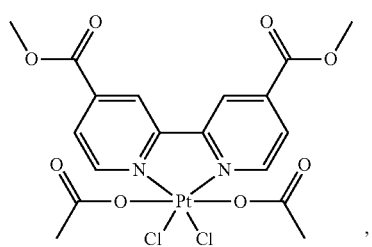
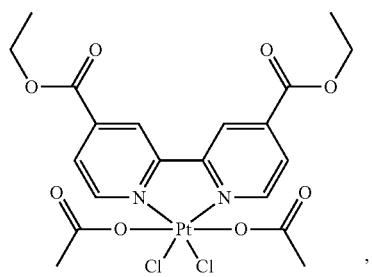
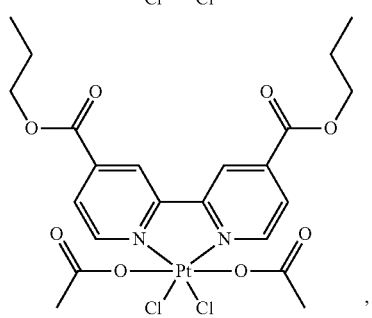
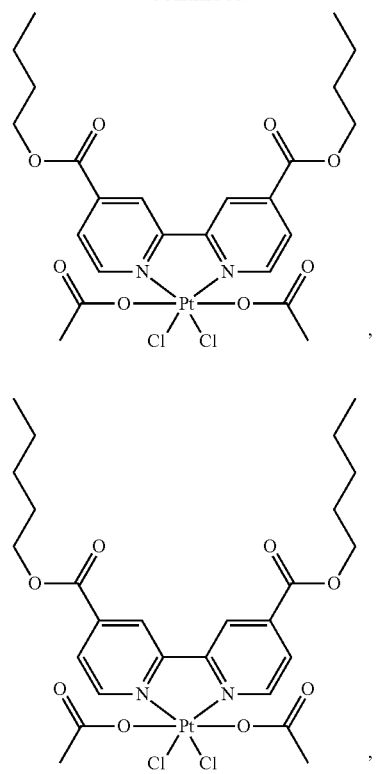
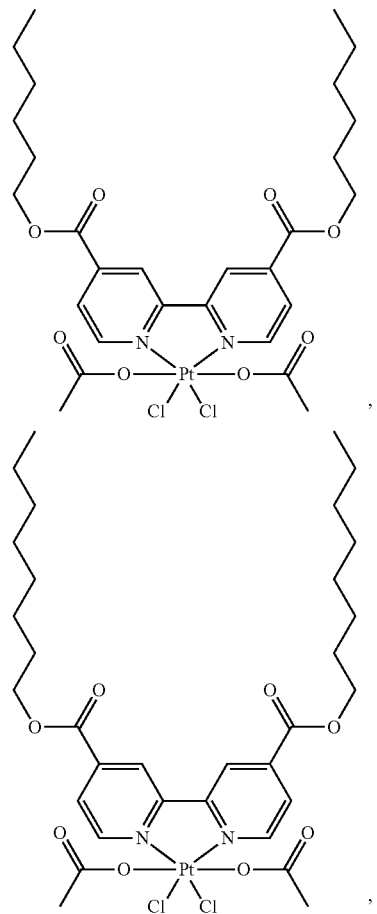

31
-continued
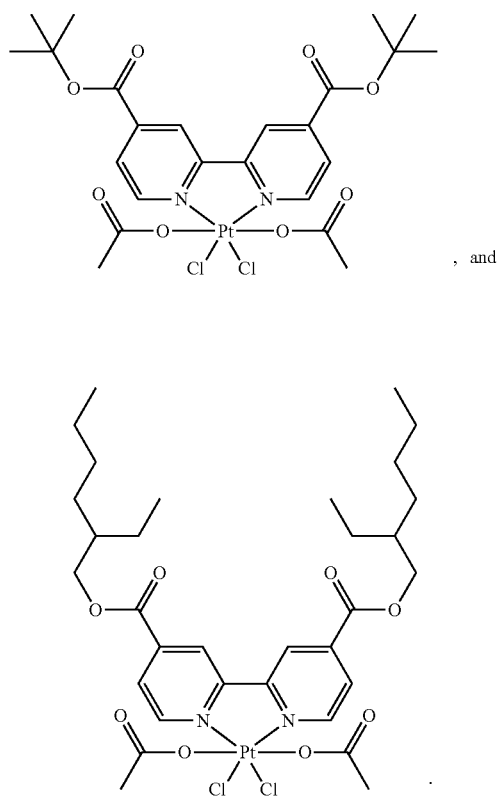
32
-continued
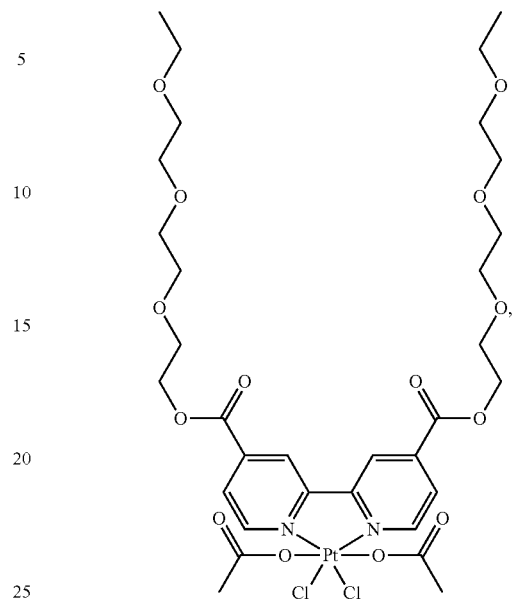
, and
In a further aspect, disclosed are platinum complexes having a structure selected from:
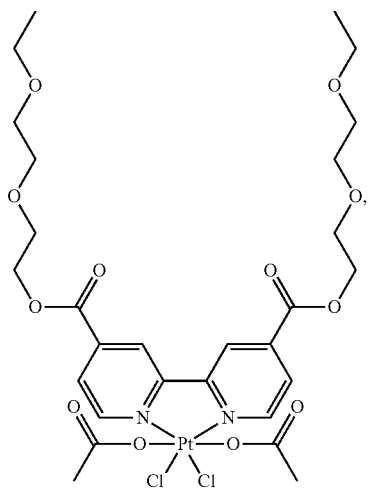
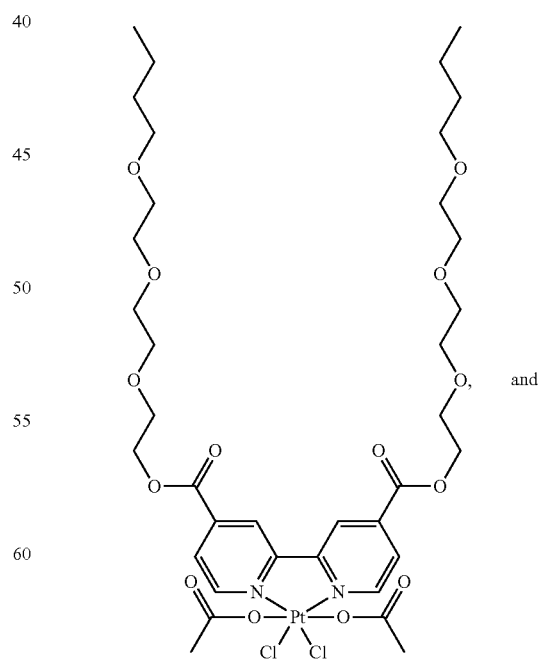
, and 33
-continued

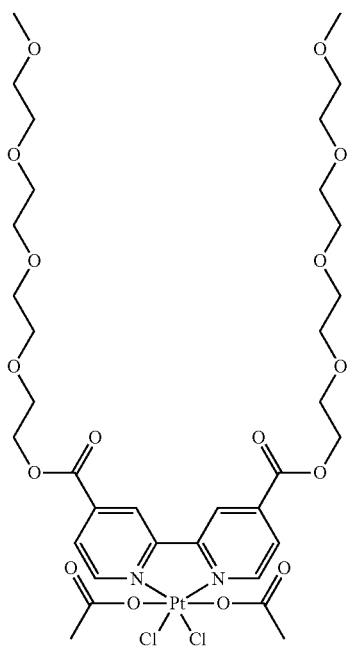

C. METHODS OF MAKING PLATINUM COMPLEXES

In one aspect, the invention relates to methods of making complexes useful in the treatment of a cancer. The complexes of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Platinum complexes as described herein can be generated using any suitable method, including those described herein and those described elsewhere (see, e.g., Price et al., *Inorg Chem* 11:1280-1284, 1972). In certain specific examples, the disclosed complexes can be prepared by the routes described and exemplified below.

In a further aspect, a complex comprises the product of the disclosed methods. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one disclosed complex or at least one product of the disclosed methods with a pharmaceutically acceptable carrier or diluent.

1. Route I

In one aspect, substituted Pt(II) intermediates can be prepared as shown below.

34

SCHEME 1A.

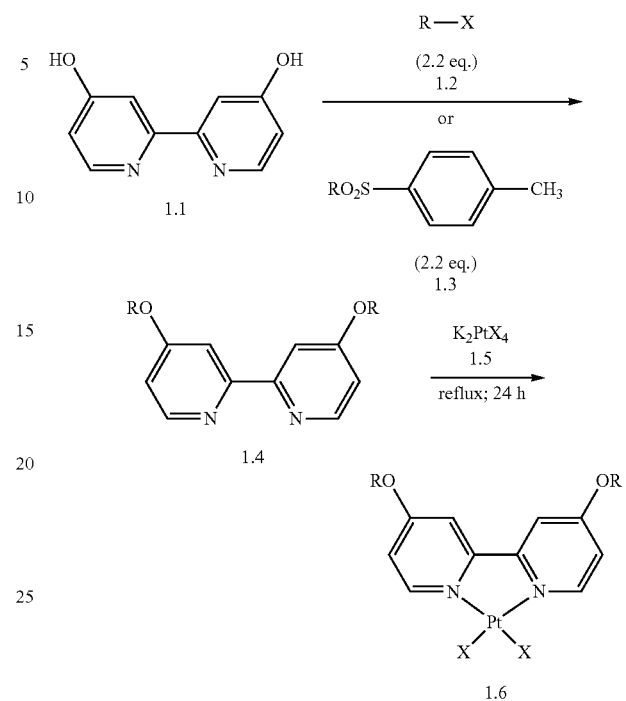

Compounds are represented in generic form, with substituents as noted in compound descriptions elsewhere herein. A more specific example is set forth below.

SCHEME 1B.

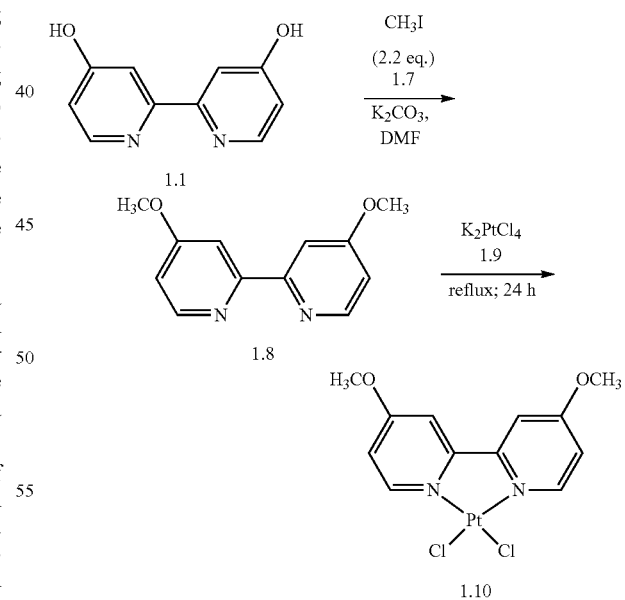

In one aspect, the synthesis of Pt(IV) analogs can begin with [2,2'-bipyridine]-4,4'-diol. [2,2'-Bipyridine]-4,4'-diol is commercially available or readily prepared by one skilled in the art. Thus, compounds of type 1.10, and similar compounds, can be prepared according to reaction Scheme 1B above. Compounds of type 1.8 can be prepared by an alkylation reaction of an appropriate bipyridine, e.g., 1.1 as shown above. The alkylation reaction is carried out in the presence of 2.2 equivalents of an appropriate alkyl halide or alkyl tosylate, e.g., 1.7 as shown above, and an appropriate base, e.g., cesium carbonate or potassium carbonate as shown above, at an appropriate temperature, e.g., refluxing conditions, in an appropriate solvent, e.g., dimethylformamide (DMF), for an appropriate period of time, e.g., 48 h. Compounds of type 1.10 can be prepared by a displacement reaction of an appropriate alkali and alkaline platinum salt, e.g., 1.9 as shown above. Appropriate alkali and alkaline platinum salts, including monovalent, e.g., Na$^+$, K$^+$, and Li$^+$, and divalent, e.g., Ca$^{+2}$ and Mg$^{+2}$, salts, are commercially available or prepared by methods known to one skilled in the art. The displacement reaction is carried out in the presence of an appropriate solvent, e.g., acetone, at an appropriate temperature, e.g., refluxing conditions, for an appropriate period of time, e.g., 24 h. As can be appreciated by one skilled in the art, the above reaction provides an example of a generalized approach wherein compounds similar in structure to the specific reactants above (compounds similar to compounds of type 1.1, 1.2, 1.3, 1.4, and 1.5), can be substituted in the reaction to provide substituted Pt(II) intermediates similar to Formula 1.6.

2. Route II

In one aspect, substituted Pt(II) intermediates can be prepared as shown below.

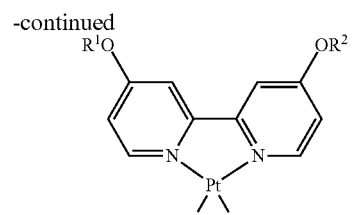

Compounds are represented in generic form, with substituents as noted in compound descriptions elsewhere herein. A more specific example is set forth below.

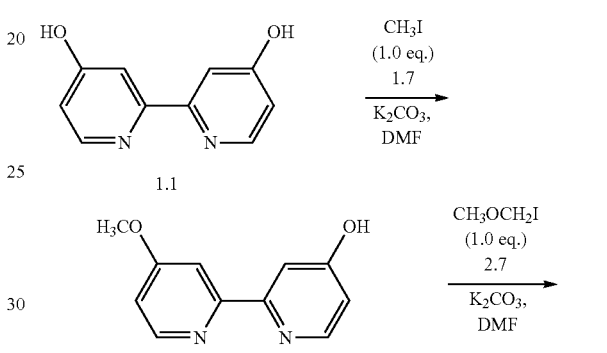

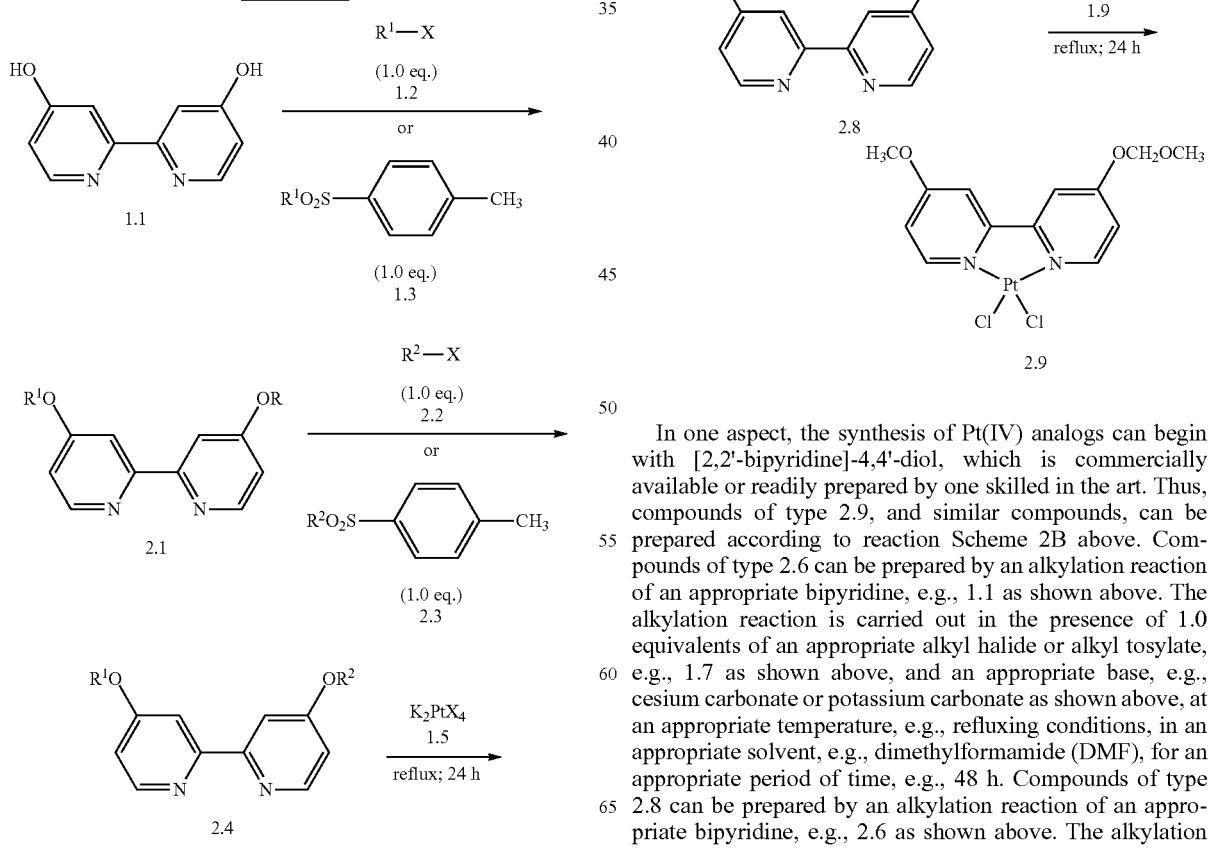

In one aspect, the synthesis of Pt(IV) analogs can begin with [2,2'-bipyridine]-4,4'-diol, which is commercially available or readily prepared by one skilled in the art. Thus, compounds of type 2.9, and similar compounds, can be prepared according to reaction Scheme 2B above. Compounds of type 2.6 can be prepared by an alkylation reaction of an appropriate bipyridine, e.g., 1.1 as shown above. The alkylation reaction is carried out in the presence of 1.0 equivalents of an appropriate alkyl halide or alkyl tosylate, e.g., 1.7 as shown above, and an appropriate base, e.g., cesium carbonate or potassium carbonate as shown above, at an appropriate temperature, e.g., refluxing conditions, in an appropriate solvent, e.g., dimethylformamide (DMF), for an appropriate period of time, e.g., 48 h. Compounds of type 2.8 can be prepared by an alkylation reaction of an appropriate bipyridine, e.g., 2.6 as shown above. The alkylation reaction is carried out in the presence of 1.0 equivalents of an appropriate alkyl halide or alkyl tosylate, e.g., 2.7 as shown above, and an appropriate base, e.g., cesium carbonate or potassium carbonate as shown above, at an appropriate temperature, e.g., refluxing conditions, in an appropriate solvent, e.g., dimethylformamide (DMF), for an appropriate period of time, e.g., 48 h. Compounds of type 2.9 can be prepared by a displacement reaction of an appropriate alkali and alkaline platinum salt, e.g., 1.9 as shown above. Appropriate alkali and alkaline platinum salts, including monovalent, e.g., $Na^+$, $K^+$, and $Li^+$, and divalent, e.g., $Ca^{+2}$ and $Mg^{+2}$, salts, are commercially available or prepared by methods known to one skilled in the art. The displacement reaction is carried out in the presence of an appropriate solvent, e.g., acetone, at an appropriate temperature, e.g., refluxing conditions, for an appropriate period of time, e.g., 24 h. As can be appreciated by one skilled in the art, the above reaction provides an example of a generalized approach wherein compounds similar in structure to the specific reactants above (compounds similar to compounds of type 1.1, 1.2, 1.3, 1.5, 2.1, 2.2, 2.3, and 2.4), can be substituted in the reaction to provide substituted Pt(II) intermediates similar to Formula 2.5.

3. Route III

In one aspect, substituted Pt(IV) complexes can be prepared as shown below.

SCHEME 3A.

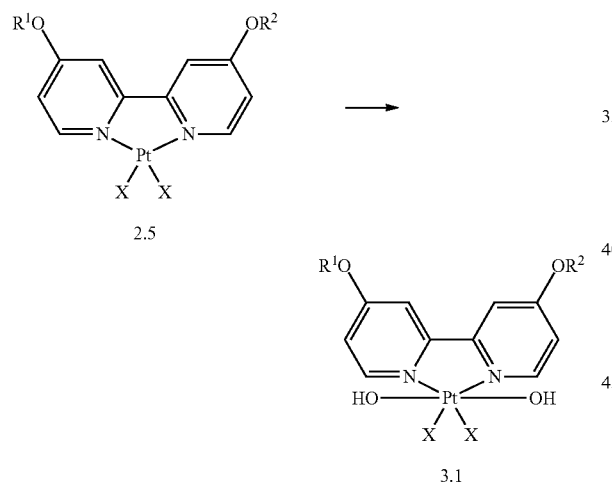

2.5

3.1

Compounds are represented in generic form, with substituents as noted in compound descriptions elsewhere herein. A more specific example is set forth below.

SCHEME 3B.

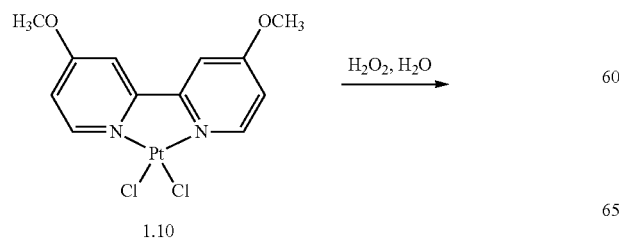

1.10

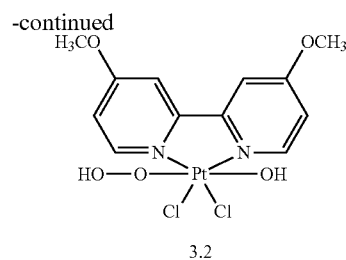

3.2

In one aspect, substituted Pt(IV) analogs can be prepared via oxidation of Pt(II) compounds. See, e.g., Lee et al., *Inorg Chem Commun* 6:249-251, 2003. Thus, compounds of type 3.2, and similar compounds, can be prepared according to reaction Scheme 3B above. Compounds of type 3.2 can be prepared by oxidation of an appropriate Pt(II) compound, e.g., 1.10 as shown above. The oxidation is carried out in the presence of an appropriate oxidant, e.g., hydrogen peroxide as shown above. As can be appreciated by one skilled in the art, the above reaction provides an example of a generalized approach wherein compounds similar in structure to the specific reactants above (compounds similar to compounds of type 2.5), can be substituted in the reaction to provide substituted Pt(IV) complexes similar to Formula 3.1.

4. Route IV

In one aspect, substituted Pt(IV) complexes can be prepared as shown below.

SCHEME 4A.

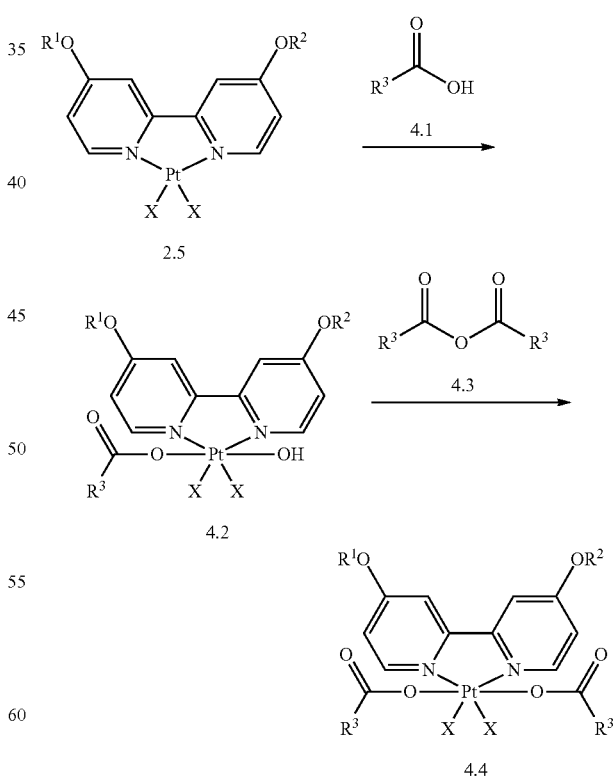

Compounds are represented in generic form, with substituents as noted in compound descriptions elsewhere herein. A more specific example is set forth below.

SCHEME 4B.

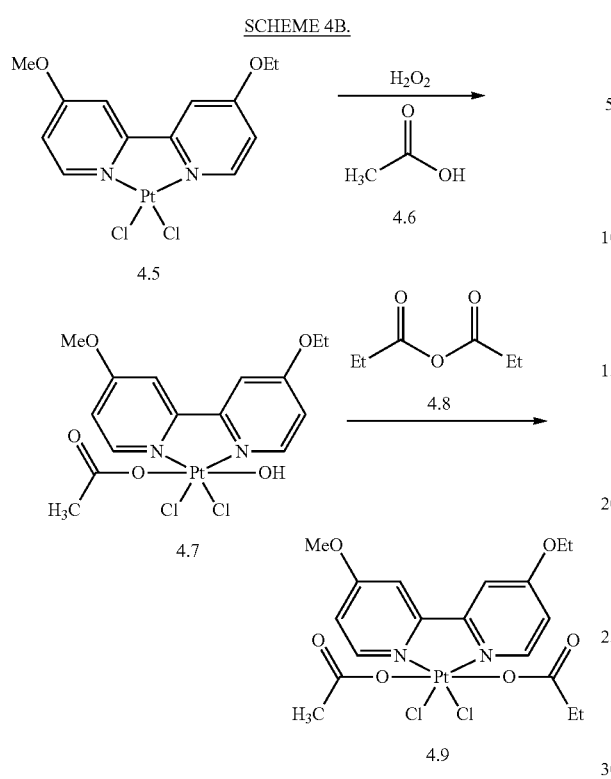

In one aspect, substituted Pt(IV) analogs can be prepared via oxidation of Pt(II) compounds. See, e.g., Lee et al., *Inorg Chem Commun* 6:249-251, 2003. Thus, compounds of type 4.9, and similar compounds, can be prepared according to reaction Scheme 4B above. Compounds of type 4.7 can be prepared by oxidation of an appropriate Pt(II) compound, e.g., 4.5 as shown above. The oxidation is carried out in the presence of an appropriate oxidant, e.g., hydrogen peroxide as shown above, and an appropriate carboxylic acid, e.g., 4.6 as shown above. Compounds of type 4.9 can be prepared by esterification of an appropriate Pt(IV) complex, e.g., 4.7 as shown above. The esterification is carried out in the presence of an appropriate anhydride, e.g., 4.8 as shown above. As can be appreciated by one skilled in the art, the above reaction provides an example of a generalized approach wherein compounds similar in structure to the specific reactants above (compounds similar to compounds of type 2.5, 4.1, 4.2, and 4.3), can be substituted in the reaction to provide substituted Pt(IV) complexes similar to Formula 4.4.

5. Route V

In one aspect, substituted Pt(IV) complexes can be prepared as shown below.

SCHEME 5A.

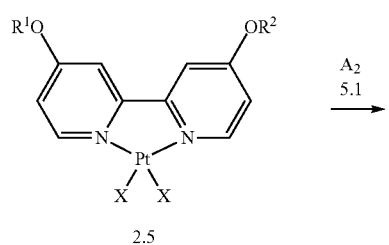

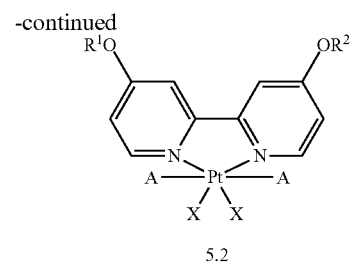

Compounds are represented in generic form, with substituents as noted in compound descriptions elsewhere herein. A more specific example is set forth below.

SCHEME 5B.

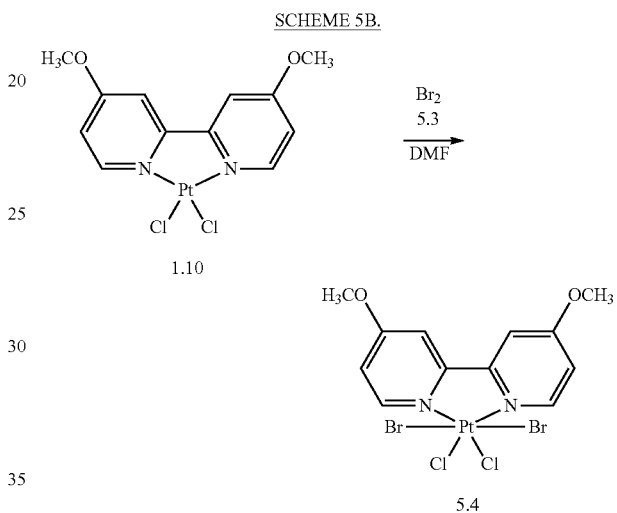

In one aspect, substituted Pt(IV) analogs can be prepared via oxidation of Pt(II) compounds. Thus, compounds of type 5.4, and similar compounds, can be prepared according to reaction Scheme 5B above. Compounds of type 5.4 can be prepared by oxidation of an appropriate Pt(II) compound, e.g., 1.10 as shown above. The oxidation is carried out in the presence of an appropriate halide, e.g., 5.3 as shown above. As can be appreciated by one skilled in the art, the above reaction provides an example of a generalized approach wherein compounds similar in structure to the specific reactants above (compounds similar to compounds of type 2.5 and 5.1), can be substituted in the reaction to provide substituted Pt(IV) complexes similar to Formula 5.4.

6. Route VI

In one aspect, substituted bipyridine ligands can be prepared as shown below.

SCHEME 6A.

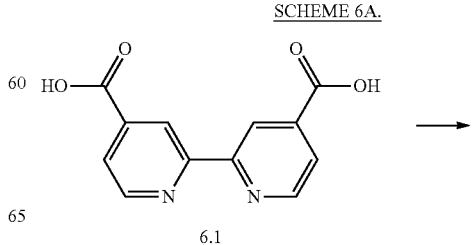

-continued

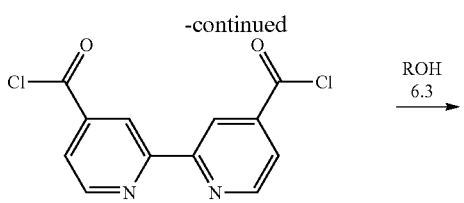

Compounds are represented in generic form, with substituents as noted in compound descriptions elsewhere herein. A more specific example is set forth below.

SCHEME 6B.

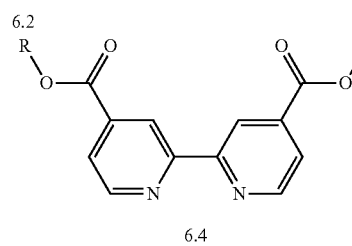

In one aspect, the synthesis of bipyridine ligands can begin with [2,2'-bipyridine]-4,4'-dicarboxylic acid. [2,2'-Bipyridine]-4,4'-dicarboxylic acid is commercially available or readily prepared by one skilled in the art. Thus, compounds of type 6.6, and similar compounds, can be prepared according to reaction Scheme 6B above. Compounds of type 6.2 can be prepared by a substitution reaction of an appropriate carboxylic acid, e.g., 6.1 as shown above. The substitution reaction is carried out in the presence of an appropriate halide source, e.g., thionyl chloride, at an appropriate temperature, e.g., refluxing conditions. Compounds of type 6.6 can be prepared by a displacement reaction of an appropriate acid chloride, e.g., 6.2 as shown above. The displacement reaction is carried out in the presence of an appropriate alcohol, e.g., 6.5 as shown above, at an appropriate temperature, e.g., refluxing conditions. As can be appreciated by one skilled in the art, the above reaction provides an example of a generalized approach wherein compounds similar in structure to the specific reactants above (compounds similar to compounds of type 6.1, 6.2, and 6.3), can be substituted in the reaction to provide substituted bipyridine ligands similar to Formula 6.4.

7. Route VII

In one aspect, substituted bipyridine ligands can be prepared as shown below.

SCHEME 7A.

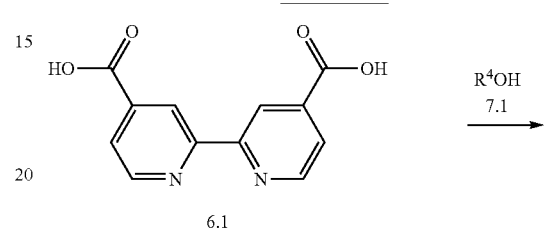

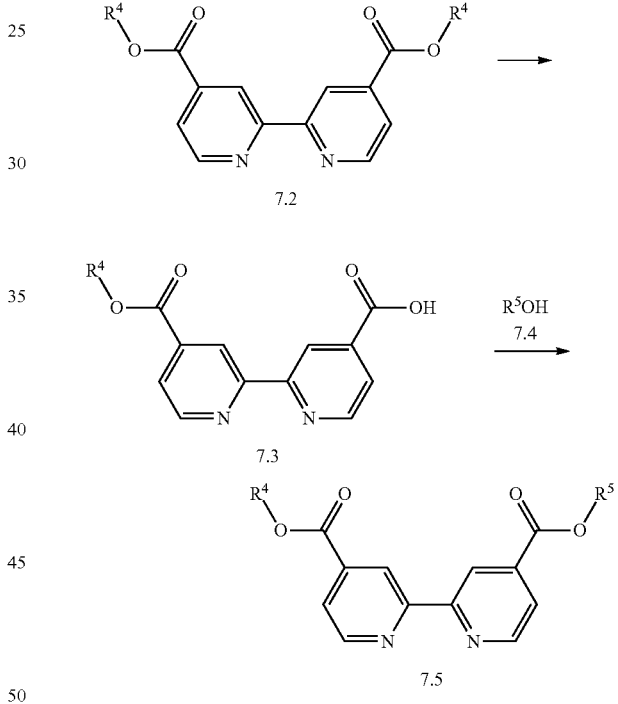

Compounds are represented in generic form, with substituents as noted in compound descriptions elsewhere herein. A more specific example is set forth below.

SCHEME 7B.

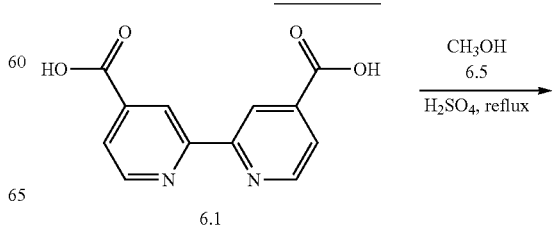

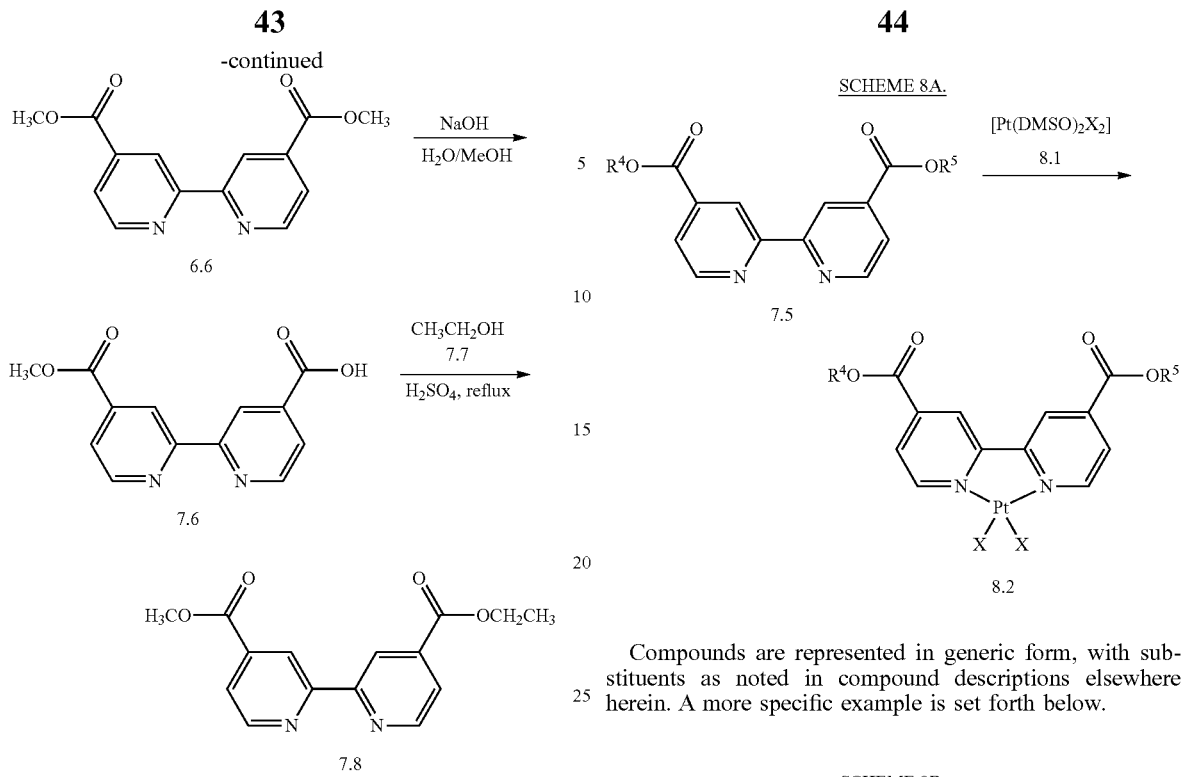

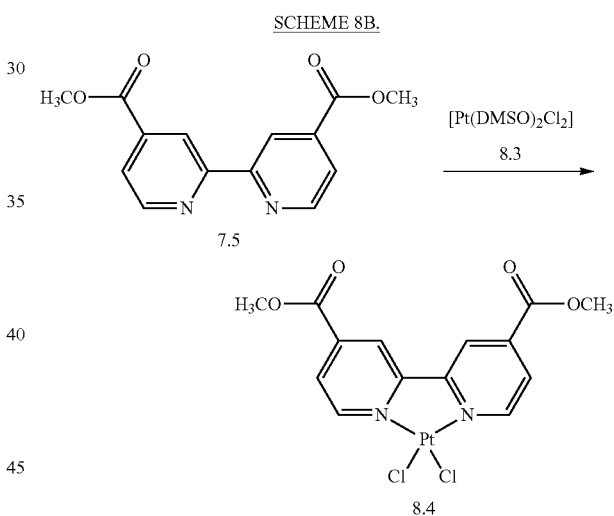

In one aspect, the synthesis of bipyridine ligands can begin with [2,2'-bipyridine]-4,4'-dicarboxylic acid. [2,2'-Bipyridine]-4,4'-dicarboxylic acid is commercially available or readily prepared by one skilled in the art. Thus, compounds of type 7.8, and similar compounds, can be prepared according to reaction Scheme 7B above. Compounds of type 6.6 can be prepared by an esterification reaction of an appropriate carboxylic acid, e.g., 6.1 as shown above. The esterification reaction is carried out in the presence of an appropriate alcohol, e.g., 6.5 as shown above, and an appropriate acid, e.g., sulphuric acid, at an appropriate temperature, e.g., refluxing conditions. Compounds of type 7.6 can be prepared by hydrolysis of an appropriate ester, e.g., 6.6 as shown above. See, e.g., Rose et al. (2008) *J. Med. Chem.* 51(22): 7053-7056. The hydrolysis is carried out in the presence of an appropriate base, e.g., sodium hydroxide, in an appropriate solvent system, e.g., water and methanol. Alternatively, compounds of type 7.6 may be obtained from a commercial source. Compounds of type 7.8 can be prepared by an esterification reaction of an appropriate carboxylic acid, e.g., 7.6 as shown above. The esterification reaction is carried out in the presence of an appropriate alcohol, e.g., 7.7 as shown above, and an appropriate acid, e.g., sulphuric acid, at an appropriate temperature, e.g., refluxing conditions. As can be appreciated by one skilled in the art, the above reaction provides an example of a generalized approach wherein compounds similar in structure to the specific reactants above (compounds similar to compounds of type 6.1, 7.1, 7.2, 7.3, and 7.4), can be substituted in the reaction to provide substituted bipyridine ligands similar to Formula 7.5.

8. Route VIII

In one aspect, substituted Pt(II) intermediates can be prepared as shown below.

Compounds are represented in generic form, with substituents as noted in compound descriptions elsewhere herein. A more specific example is set forth below.

In one aspect, the synthesis of Pt(IV) analogs can begin with substituted bipyridine ligands. Thus, compounds of type 8.4, and similar compounds, can be prepared according to reaction Scheme 8B above. Compounds of type 8.4 can be prepared by a displacement reaction of an appropriate platinum salt, e.g., 8.3 as shown above. Appropriate platinum salts can be readily prepared by one skilled in the art using, for example, the methods disclosed in the Examples section herein. The displacement reaction is carried out in the presence of an appropriate solvent system, e.g., 1:1 methanol:dichloromethane, at an appropriate temperature, e.g., refluxing conditions, for an appropriate period of time, e.g., 48 h. As can be appreciated by one skilled in the art, the above reaction provides an example of a generalized approach wherein compounds similar in structure to the specific reactants above (compounds similar to compounds of type 7.5 and 8.1), can be substituted in the reaction to provide substituted Pt(II) intermediates similar to Formula 8.2.

9. Route IX

In one aspect, substituted Pt(IV) complexes can be prepared as shown below.

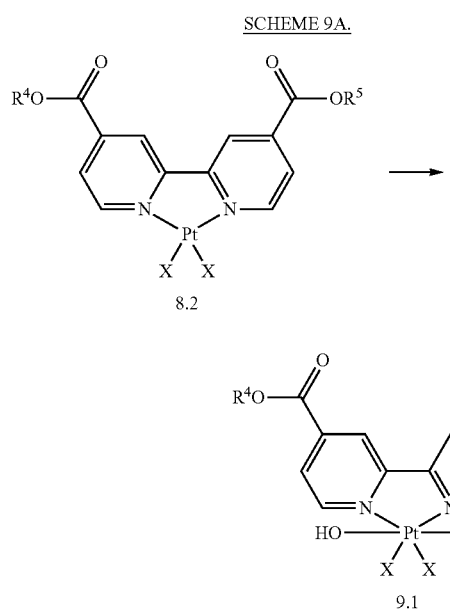

Compounds are represented in generic form, with substituents as noted in compound descriptions elsewhere herein. A more specific example is set forth below.

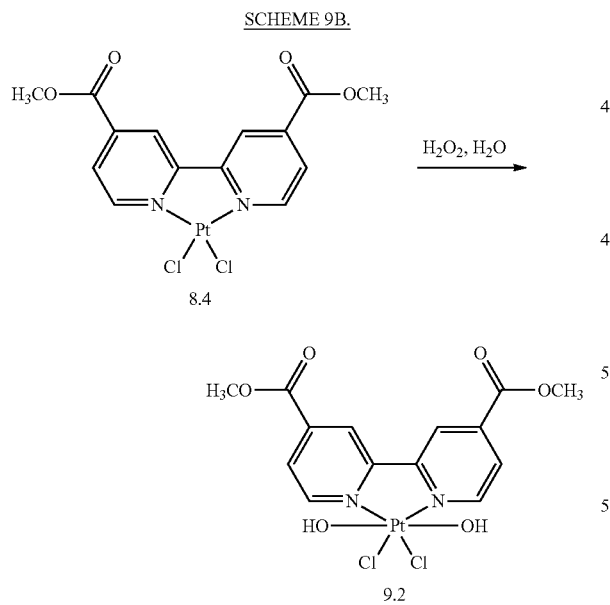

In one aspect, substituted Pt(IV) analogs can be prepared via oxidation of Pt(II) compounds. See, e.g., Lee et al., *Inorg Chem Commun* 6:249-251, 2003. Thus, compounds of type 9.2, and similar compounds, can be prepared according to reaction Scheme 9B above. Compounds of type 9.2 can be prepared by oxidation of an appropriate Pt(II) compound, e.g., 8.4 as shown above. The oxidation is carried out in the presence of an appropriate oxidant, e.g., hydrogen peroxide as shown above. As can be appreciated by one skilled in the art, the above reaction provides an example of a generalized approach wherein compounds similar in structure to the specific reactants above (compounds similar to compounds of type 8.2), can be substituted in the reaction to provide substituted Pt(IV) complexes similar to Formula 9.1.

10. Route X

In one aspect, substituted Pt(IV) complexes can be prepared as shown below.

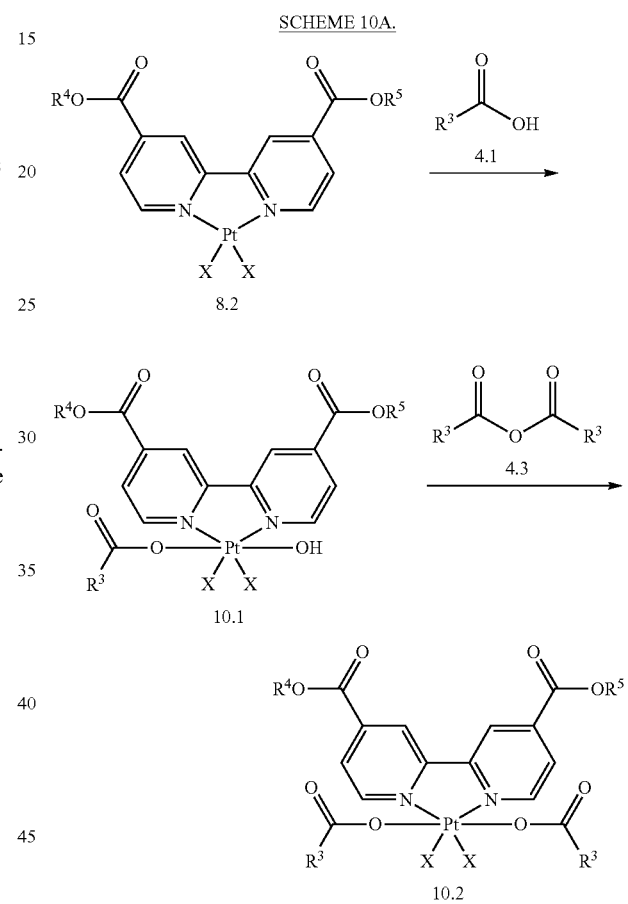

Compounds are represented in generic form, with substituents as noted in compound descriptions elsewhere herein. A more specific example is set forth below.

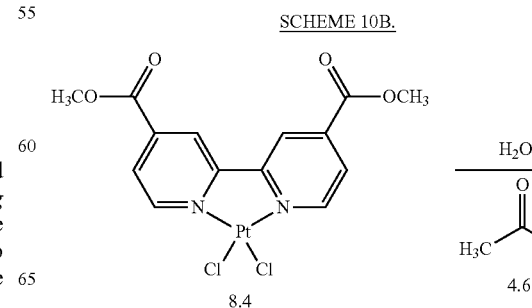

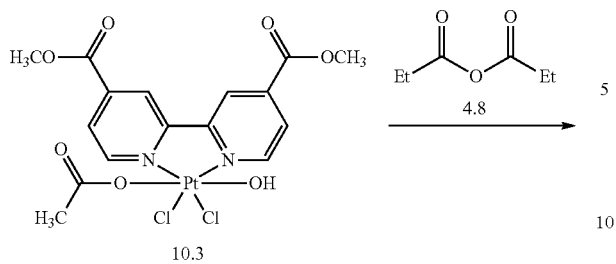

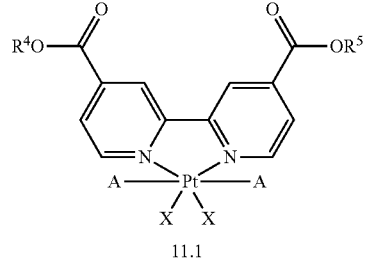

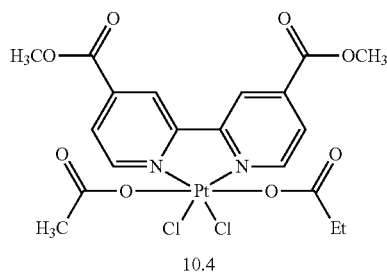

In one aspect, substituted Pt(IV) analogs can be prepared via oxidation of Pt(II) compounds. See, e.g., Lee et al., *Inorg Chem Commun* 6:249-251, 2003. Thus, compounds of type 10.4, and similar compounds, can be prepared according to reaction Scheme 10B above. Compounds of type 10.3 can be prepared by oxidation of an appropriate Pt(II) compound, e.g., 8.4 as shown above. The oxidation is carried out in the presence of an appropriate oxidant, e.g., hydrogen peroxide as shown above, and an appropriate carboxylic acid, e.g., 4.6 as shown above. Compounds of type 10.4 can be prepared by esterification of an appropriate Pt(IV) complex, e.g., 10.3 as shown above. The esterification is carried out in the presence of an appropriate anhydride, e.g., 4.8 as shown above. As can be appreciated by one skilled in the art, the above reaction provides an example of a generalized approach wherein compounds similar in structure to the specific reactants above (compounds similar to compounds of type 4.1, 4.3, 8.2, and 10.1), can be substituted in the reaction to provide substituted Pt(IV) complexes similar to Formula 10.2.

11. Route XI

In one aspect, substituted Pt(IV) complexes can be prepared as shown below.

SCHEME 11A.

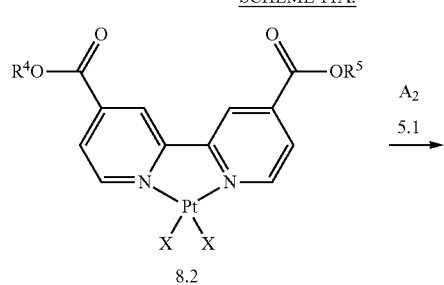

Compounds are represented in generic form, with substituents as noted in compound descriptions elsewhere herein. A more specific example is set forth below.

SCHEME 11B.

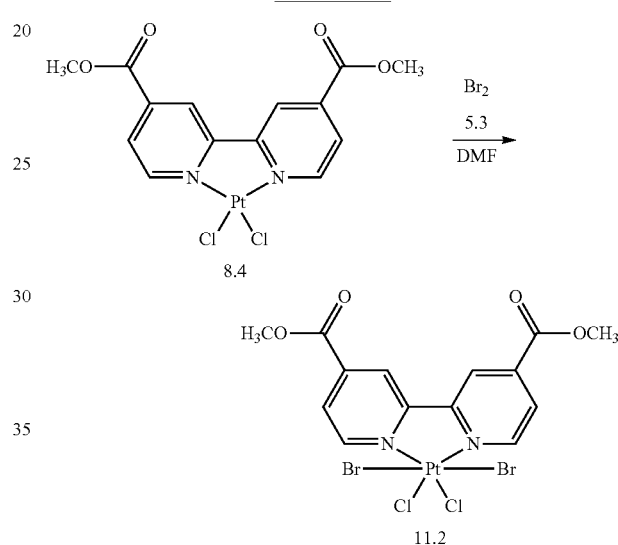

In one aspect, substituted Pt(IV) analogs can be prepared via oxidation of Pt(II) compounds. Thus, compounds of type 11.2, and similar compounds, can be prepared according to reaction Scheme 11B above. Compounds of type 11.2 can be prepared by oxidation of an appropriate Pt(II) compound, e.g., 8.4 as shown above. The oxidation is carried out in the presence of an appropriate halide, e.g., 5.3 as shown above. As can be appreciated by one skilled in the art, the above reaction provides an example of a generalized approach wherein compounds similar in structure to the specific reactants above (compounds similar to compounds of type 5.1 and 8.2), can be substituted in the reaction to provide substituted Pt(IV) complexes similar to Formula 11.1.

D. PHARMACEUTICAL COMPOSITIONS

In one aspect, the invention relates to pharmaceutical compositions comprising the disclosed complexes. That is, a pharmaceutical composition can be provided comprising a therapeutically effective amount of at least one disclosed complex or at least one product of a disclosed method and a pharmaceutically acceptable carrier.

Platinum complexes as provided herein can be incorporated into compositions for contacting cancer cells in vitro or in vivo. A composition can contain, for example, one or more pharmaceutically acceptable carriers, diluents and/or adjuvants. A "pharmaceutically acceptable carrier" (also referred to as an "excipient" or a "carrier") is a pharmaceutically acceptable solvent, suspending agent, stabilizing agent, or any other pharmacologically inert vehicle for delivering one or more therapeutic compounds to a subject (e.g., a human, non-human primate, mouse, rat, pig, dog, cat, sheep, or cow), which is nontoxic to the cell or mammal being exposed thereto at the dosages and concentrations employed. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers include, by way of example and not limitation: water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Pharmaceutically acceptable carriers also include aqueous pH buffered solutions or liposomes (small vesicles composed of various types of lipids, phospholipids and/or surfactants which are useful for delivery of a drug to a mammal). Further examples of pharmaceutically acceptable carriers include buffers such as phosphate, citrate, and other organic acids, antioxidants such as ascorbic acid, low molecular weight (less than about ten residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Pharmaceutical compositions can be formulated by mixing one or more platinum complexes with one or more physiologically acceptable carriers, diluents, and/or adjuvants, and optionally other agents that are usually incorporated into formulations to provide improved transfer, delivery, tolerance, and the like. Pharmaceutical compositions can be formulated, e.g., in lyophilized formulations, aqueous solutions, dispersions, or solid preparations, such as tablets, dragees or capsules. A multitude of appropriate formulations can be found in the formulary known to pharmaceutical chemists: *Remington's Pharmaceutical Sciences* (18th ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies as described herein, provided that the active agent in the formulation is not inactivated by the formulation and the formulation is physiologically compatible and tolerable with the route of administration. See, also, Baldrick, *Regul Toxicol Pharmacol* 32:210-218, 2000; Wang, *Int J Pharm* 203:1-60, 2000; Charman *J Pharm Sci* 89:967-978, 2000; and Powell et al., *PDA J Pharm Sci Technol* 52:238-311, 1998), and the citations therein for additional information related to formulations, excipients and carriers well known to pharmaceutical chemists.

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Compositions and formulations can include sterile aqueous solutions, which also can contain buffers, diluents and other suitable additives (e.g., penetration enhancers, carrier compounds and other pharmaceutically acceptable carriers). Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

In various aspects, a composition containing a Pt(IV) complex as provided herein can be in the form of a solution or powder with or without a diluent to make an injectable suspension. The composition may contain additional ingredients including, without limitation, pharmaceutically acceptable vehicles, such as saline, water, lactic acid, mannitol, or combinations thereof, for example. It is to be noted that suspension or dissolution of the Pt(IV) complexes without encapsulation or carriage in a lipid or liposome (i.e., without fatty carriers) can be particularly useful.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for the treatment of one or more cancers in mammals (e.g., humans) comprising combining one or more disclosed complexes, products, or compositions with a pharmaceutically acceptable carrier or diluent. Thus, in one aspect, the invention relates to a method for manufacturing a medicament comprising combining at least one disclosed complex or at least one disclosed product with a pharmaceutically acceptable carrier or diluent.

The disclosed pharmaceutical compositions can further comprise other therapeutically active complexes, which are usually applied in the treatment of the above mentioned pathological conditions.

In a further aspect, the pharmaceutical composition further comprises a chemotherapeutic agent. In a still further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent, or a pharmaceutically acceptable salt thereof. In yet a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof. In an even further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof. In a still further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof. In yet a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof. In an even further aspect, the mTor inhibitor agent is selected from one or more of the group consisting of everolimus, siroliumus, and temsirolimus, or a pharmaceutically acceptable salt thereof.

It is understood that the disclosed pharmaceutical compositions can be prepared from the disclosed complexes. It is also understood that the disclosed pharmaceutical compositions can be employed in the disclosed methods of using.

E. METHODS OF USING THE COMPLEXES AND COMPOSITIONS

The pharmaceutical compositions and methods of the present invention can further comprise other therapeutically active compounds and/or complexes as noted herein which are usually applied in the treatment of the above mentioned pathological conditions.

The disclosed complexes can be used as single agents or in combination with one or more other drugs in the treatment, prevention, control, amelioration, or reduction of risk of the aforementioned diseases, disorders and conditions, where the combination of drugs together are safer or more effective than either drug alone. The other drug(s) can be administered by a route and in an amount commonly used therefore, contemporaneously or sequentially with a disclosed complex. When a disclosed complex is used contemporaneously with one or more other drugs, a pharmaceutical composition in unit dosage form containing such drugs and the disclosed complex is preferred. However, the combination therapy can also be administered on overlapping schedules. It is also envisioned that the combination of one or more active ingredients and a disclosed complex will be more efficacious than either as a single agent.

1. Treatment Methods

The compounds disclosed herein are useful for treating, preventing, ameliorating, controlling or reducing the risk of a cancer. Thus, in one aspect, provided is a method for treating a cancer, the method comprising administering to a subject at least one disclosed complex; at least one disclosed pharmaceutical composition; and/or at least one disclosed product in a dosage and amount effective to treat the cancer in the subject. Also provided is a method for the treatment of a cancer in a mammal comprising the step of administering to the mammal at least one disclosed complex, composition, or medicament.

In one aspect, methods for treating a subject having cancer, the method comprising administering to the subject an effective amount of a composition comprising a complex having a structure represented by a formula:

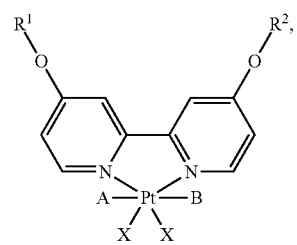

wherein each X is independently —Br, —Cl, or —I; and wherein each of A and B is independently selected from —Br, —Cl, —I, —OH, and —OC(O)R³; wherein R³ is —(CH₂)ₚCH₃; and wherein p is selected from 0, 1, 2, 3, 4, 5, 6, 7, 8, 9, and 10; wherein each of R¹ and R² is independently selected from —(CH₂)ₙCH₃, —(CH₂)ₙOCH₃, and —(CH₂)[O(CH₂)ₘ]ᵧO(CH₂)_zCH₃; wherein n is selected from 1, 2, 3, 4, 5, 6, 7, 8, 9, and 10; wherein each of m, y, and z is independently selected from 0, 1, 2, 3, 4, 5, 6, 7, 8, 9, and 10, or a pharmaceutically acceptable derivative thereof are disclosed.

In one aspect, methods for treating a subject having cancer, the method comprising administering to the subject an effective amount of a composition comprising a complex have a structure represented by a formula selected from:

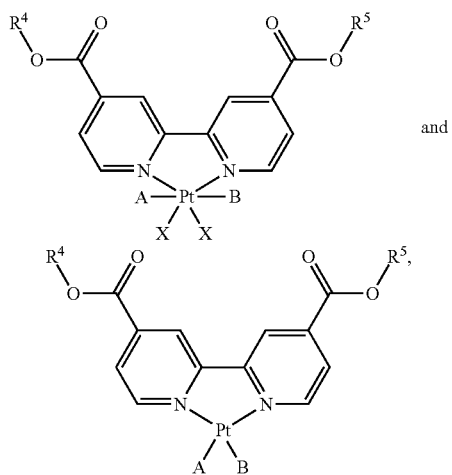

and wherein each of $R^4$ and $R^5$ is independently selected from $-(CH_2)_tCH_3$, $-C(CH_3)_3$, $-CH_2CH(CH_2CH_3)CH_2CH_2CH_2CH_3$, $-(CH_2CH_2O)_2CH_2CH_3$, $-(CH_2CH_2O)_3$ $CH_2CH_3$, $-(CH_2CH_2O)_3(CH_2)_3CH_3$, and $-(CH_2CH_2O)_4$ $CH_3$; wherein t is selected from 0, 1, 2, 3, 4, 5, 6, and 7; wherein each X is independently —Br, —Cl, or —I; and wherein each of A and B is independently selected from —Br, —Cl, —I, —OH, and —OC(O)$R^3$; wherein $R^3$ is $-(CH_2)_pCH_3$; and wherein p is selected from 0, 1, 2, 3, 4, 5, 6, 7, 8, 9, and 10, or a pharmaceutically acceptable derivative thereof are disclosed.

The invention is directed at the use of the described chemical compositions to treat cancer in patients (preferably human) by administering one or more disclosed complexes, compositions, or products.

In various aspects, the Pt(IV) complexes described herein can be used to treat cancer patients. Thus, this document provides methods for treating cancer patients, and for reducing the in vivo viability of cancer cells (e.g., breast cancer cells, lung cancer cells, prostate cancer cells, and melanoma cancer cells) in cancer patients. The methods can include, for example, identifying a cancer patient (e.g., a patient identified as having a cancer such as breast cancer, lung cancer, prostate cancer, or melanoma), and administering to the patient a Pt(IV) compound or a composition containing a Pt(IV) compound as described herein, at an amount effective to reduce the viability of cancer cells in the patient.

The term "treatment" as used herein is a term well understood in the field of medical technology. It is noted that "treatment" is not equivalent to a cure, but it is a procedure with effects on, for example, reducing the number or concentration of cancer cells, slowing the growth of tumors or cancer cells, limiting the reproducibility of cancer cells, causing deterioration of cancer cells, or increasing the mortality of cancer cells, any of which can have benefits over the absence of treatment.

The complexes and compositions can be provided to an affected tissue using, for example, general administration (e.g., oral, intravenous, topical, or transdermal administration), or targeted administration (e.g., diffusion from a catheter, implantation, perfusion through a catheter, injection, or infusion). Thus, administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral. In addition, a composition containing a platinum complex as described herein can be administered prior to, after, or in lieu of surgical resection of a tumor.

A composition containing a platinum complex can be administered in any appropriate amount, at any appropriate frequency, and for any appropriate duration effective to achieve a desired outcome (e.g., to increase progression-free survival, or to reduce progression of the cancer).

Any suitable concentration or amount of the complexes and compositions provided herein can be used. An effective amount of a composition containing a platinum complex as provided herein can be any amount that reduces a symptom of the condition being treated, without significant toxicity. With cancer, an effective amount can reduce the progression rate of the cancer, increase the progression-free survival rate, increase the median time to progression, slow cancer cell or tumor growth, reduce the number or concentration of cancer cells, limit cancer cell reproducibility, cause cancer cell deterioration, and/or increase cancer cell mortality, for example. Optimum dosages can vary depending on the relative potency of individual complexes, and generally can be estimated based on $EC_{50}$ found to be effective in in vitro and in vivo animal models. Typically, dosage is from 0.01 µg to 100 g per kg of body weight. For example, an effective amount of an antibody or fusion protein can be from about 1 mg/kg to about 100 mg/kg (e.g., about 5 mg/kg, about 10 mg/kg, about 20 mg/kg, about 50 mg/kg, or about 75 mg/kg). If a particular subject fails to respond to a particular amount, then the amount of the antibody can be increased by, for example, two fold. After receiving this higher concentration, the subject can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the clinical condition may require an increase or decrease in the actual effective amount administered.

In some embodiments, for example, the concentration of a complex administered locally may be effective in picogram quantities at the site (e.g., at least 1.0 pg/mm² of cancerous cell environment, or about 20 to 100 mg/m² for six to eight hours where the environment is the entire volume of the region where cells have been identified and the in vivo blood supply of the patient to be treated and not the volume of cancerous cells themselves. Higher concentrations or amounts of the complexes and compositions also can be used, such as with general administration, with nanogram concentrations (e.g., 1 to 100 ng/mm cancerous cell environment), or even milligram concentrations (e.g., about 1 mg/mm cancerous cell environment). This amount may be greatly increased over time (e.g., these amounts may be delivered over 10 seconds, thirty seconds, minutes, hours, or days), as the treatments typically are not single events but rather are episodic or continuous treatments.

The frequency of administration can be any frequency that has a desired effect (e.g., reduces the progression rate of cancer, increases the progression-free survival rate, increases the median time to progression, slows cancer cell or tumor growth, reduces the number or concentration of cancer cells, limits cancer cell reproducibility, causes cancer cell deterioration, and/or increases cancer cell mortality) without producing significant toxicity to the mammal. For example, the frequency of administration can be once or more daily, biweekly, weekly, monthly, or even less. The frequency of administration can remain constant or can be variable during the duration of treatment. A course of treatment can include rest periods. For example, a complex or composition can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition provided herein can be any duration that, for example, reduces the progression rate of cancer, increases the progression-free survival rate, increases the median time to progression, slows cancer cell or tumor growth, reduces the number or concentration of cancer cells, limits cancer cell reproducibility, causes cancer cell deterioration, and/or increases cancer cell mortality, without producing significant toxicity to the mammal. Thus, the effective duration can vary from several days to several weeks, months, or years. In general, the effective duration for the treatment of cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer.

After administering a platinum complex or composition as provided herein to a cancer patient, the patient can be monitored to determine whether or not the treatment was effective. For example, a patient can be assessed after treatment to determine whether or not the progression rate of the cancer has been reduced. Any method, including those that are standard in the art, can be used to assess progression and survival rates.

Also provided is a method of use of a disclosed complex, composition, or medicament. In one aspect, the method of use is directed to the treatment of a cancer. In a further aspect, the disclosed complexes can be used as single agents or in combination with one or more other drugs in the treatment, prevention, control, amelioration or reduction of risk of the aforementioned diseases, disorders and conditions for which the complex or the other drugs have utility, where the combination of drugs together are safer or more effective than either drug alone. The other drug(s) can be administered by a route and in an amount commonly used therefore, contemporaneously or sequentially with a disclosed complex. When a disclosed complex is used contemporaneously with one or more other drugs, a pharmaceutical composition in unit dosage form containing such drugs and the disclosed complex is preferred. However, the combination therapy can also be administered on overlapping schedules. It is also envisioned that the combination of one or more active ingredients and a disclosed complex can be more efficacious than either as a single agent.

In a further aspect, the cancer is a sarcoma. In a still further aspect, the cancer is a carcinoma. In yet a further aspect, the cancer is a hematological cancer. In an even further aspect, the cancer is a solid tumor.

It is understood that cancer refers to or describe the physiological condition in mammals that is typically characterized by unregulated cell growth. The cancer may be multi-drug resistant (MDR) or drug-sensitive. Examples of cancer include, but are not limited to, carcinoma, lymphoma, blastoma, sarcoma, and leukemia. More particular examples of such cancers include, but are not limited to, breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers include, but are not limited to, basal cell carcinoma, biliary tract cancer; bone cancer; brain and CNS cancer; choriocarcinoma; connective tissue cancer; esophageal cancer; eye cancer; cancer of the head and neck; gastric cancer; intraepithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

In a further aspect, the cancer is breast cancer, prostate cancer, lung cancer, or melanoma.

In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In a further aspect, the cancer is selected from a cancer of the breast, cervix, gastrointestinal tract, colorectal tract, brain, skin, prostate, ovary, thyroid, testes, genitourinary tract, pancreas, and endometrias. In a still further aspect, the cancer is a cancer of the breast. In yet a further aspect, the cancer of the breast is a hormone resistant cancer. In an even further aspect, the cancer of the breast is a hormone resistant cancer. In a still further aspect, the cancer is a cancer of the cervix. In yet a further aspect, the cancer is a cancer of the ovary. In an even further aspect, the cancer is a cancer of the endometrias. In a still further aspect, the cancer is a cancer of the genitourinary tract. In yet a further aspect, the cancer is a cancer of the colorectal tract. In an even further aspect, the cancer of the colorectal tract is a colorectal carcinoma. In a still further aspect, the cancer is a cancer of the gastrointestinal tract. In yet a further aspect, the cancer of the gastrointestinal tract is a gastrointestinal stromal tumor. In an even further aspect, the cancer is a cancer of the skin. In a still further aspect, the cancer of the skin is a melanoma. In yet a further aspect, the cancer is a cancer of the brain. In an even further aspect, the cancer of the brain is a glioma. In a still further aspect, the glioma is glioblastoma multiforme. In yet a further aspect, glioma is selected from is selected from a ependymoma, astrocytoma, oligodendroglioma, and oligoastrocytoma. In an even further aspect, the cancer of the brain is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, and hemangiopercytoma. In a still further aspect, the hematological cancer is selected from a leukemia, lymphoma, chronic myeloproliferative disorder, myelodysplastic syndrome, myeloproliferative neoplasm, and plasma cell neoplasm (myeloma). In yet a further aspect, the hematological cancer is leukemia. In an even further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia. In a still further aspect, the leukemia is acute lymphocytic leukemia. In yet a further aspect, the hematological cancer is lymphoma. In an even further aspect, the hematological cancer is myeloma. In a still further aspect, the myeloma is multiple myeloma.

In a further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer is selected from breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

In a further aspect, the cancer is treatment-resistant. In a still further aspect, the cancer is resistant to treatment with the at least one chemotherapeutic agent. In yet a further aspect, the cancer is resistant to treatment with the at least one hormone therapy agent.

The complexes are further useful in a method for the prevention, treatment, control, amelioration, or reduction of risk of the diseases, disorders and conditions noted herein. The complexes are further useful in a method for the prevention, treatment, control, amelioration, or reduction of risk of the aforementioned diseases, disorders and conditions in combination with other agents.

The present invention is further directed to administration of a disclosed complex for improving treatment outcomes in the context of cancer. That is, in one aspect, the invention relates to a cotherapeutic method comprising the step of administering to a mammal an effective amount and dosage of at least one complex of the invention in connection with cancer therapy.

In a further aspect, administration improves treatment outcomes in the context of cancer therapy. Administration in connection with cancer therapy can be continuous or intermittent. Administration need not be simultaneous with therapy and can be before, during, and/or after therapy. For example, cancer therapy can be provided within 1, 2, 3, 4, 5, 6, 7 days before or after administration of the compound. As a further example, cancer therapy can be provided within 1, 2, 3, or 4 weeks before or after administration of the compound. As a still further example, cancer therapy can be provided before or after administration within a period of time of 1, 2, 3, 4, 5, 6, 7, 8, 9, or 10 half-lives of the administered compound.

In one aspect, the disclosed complexes can be used in combination with one or more other drugs in the treatment, prevention, control, amelioration, or reduction of risk of diseases or conditions for which disclosed complexes or the other drugs can have utility, where the combination of the drugs together are safer or more effective than either drug alone. Such other drug(s) can be administered, by a route and in an amount commonly used therefor, contemporaneously or sequentially with a complex of the present invention. When a complex of the present invention is used contemporaneously with one or more other drugs, a pharmaceutical composition in unit dosage form containing such other drugs and a disclosed complex is preferred. However, the combination therapy can also include therapies in which a disclosed complex and one or more other drugs are administered on different overlapping schedules. It is also contemplated that when used in combination with one or more other active ingredients, the disclosed complexes and the other active ingredients can be used in lower doses than when each is used singly.

Accordingly, the pharmaceutical compositions include those that contain one or more other active ingredients, in addition to a complex of the present invention.

The above combinations include combinations of a disclosed complex not only with one other active complex and/or compound, but also with two or more other active complexes and/or compounds. Likewise, disclosed complexes can be used in combination with other drugs that are used in the prevention, treatment, control, amelioration, or reduction of risk of the diseases or conditions for which the disclosed complexes are useful. Such other drugs can be administered, by a route and in an amount commonly used therefor, contemporaneously or sequentially with a complex of the present invention. When a complex of the present invention is used contemporaneously with one or more other drugs, a pharmaceutical composition containing such other drugs in addition to a disclosed complex is preferred.

Accordingly, the pharmaceutical compositions include those that also contain one or more other active ingredients, in addition to a complex of the present invention.

The weight ratio of a disclosed complex to the second active ingredient can be varied and will depend upon the effective dose of each ingredient. Generally, an effective dose of each will be used. Thus, for example, when a complex of the present invention is combined with another agent, the weight ratio of a disclosed complex to the other agent will generally range from about 1000:1 to about 1;1000, preferably about 200:1 to about 1:200. Combinations of a complex of the present invention and other active ingredients will generally also be within the aforementioned range, but in each case, an effective dose of each active ingredient should be used.

In such combinations a disclosed complex and other active agents can be administered separately or in conjunction. In addition, the administration of one element can be prior to, concurrent to, or subsequent to the administration of other agent(s).

Accordingly, the subject complexes can be used alone or in combination with other agents which are known to be beneficial in the subject indications or other drugs that affect receptors or enzymes that either increase the efficacy, safety, convenience, or reduce unwanted side effects or toxicity of the disclosed complexes. The subject complex and the other agent can be coadministered, either in concomitant therapy or in a fixed combination.

In one aspect, the complex can be employed in combination with anti-cancer therapeutic agents. In a further aspect, the anti-cancer therapeutic agent is selected from 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphaIfosfamide, IL-11IL-2Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Oraprex®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a) Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®.

In another aspect, the subject complexes can be administered in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphaIfosfamide, IL-11IL-2Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a)Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®

In another aspect, the subject complex can be used in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphaIfosfamide, IL-11IL-2Imatinib mesylate, Imidazole CarboxamideInterferon alfa, Interferon Alfa-2b (PEG Conjugate), Interleukin- 2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a)Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid 8, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®

In the treatment of conditions which require inhibition or negative modulation of β-catenin/Tcf protein-protein interaction, an appropriate dosage level will generally be about 0.01 to 1000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The complexes can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific complex employed, the metabolic stability and length of action of that complex, the age, body weight, general health, sex, diet, mode and time of administration, rate of excretion, drug combination, the severity of the particular condition, and the host undergoing therapy.

In a further aspect, the effective amount is a therapeutically effective amount. In a still further aspect, the effective amount is a prophylactically effective amount.

In a further aspect, the subject is a mammal. In a still further aspect, the mammal is a human. In yet a further aspect, the subject has been diagnosed with a need for treatment of the disorder prior to the administering step. In an even further aspect, the subject has been diagnosed with a need for cancer treatment prior to the administering step. In an even further aspect, the method further comprises the step of identifying a subject in need of treatment of the disorder. In a still further aspect, the method further comprises the step of identifying a subject in need for cancer treatment.

In a further aspect, complex has a structure represented by a formula:

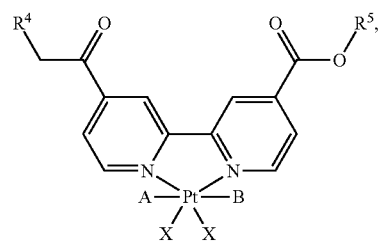

or a pharmaceutically acceptable derivative thereof.

In a further aspect, the complex has a structure represented by a formula:

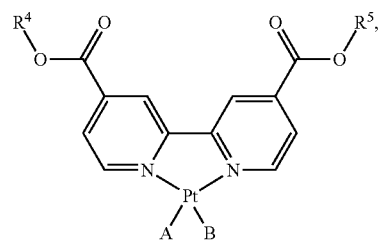

or a pharmaceutically acceptable derivative thereof.

In a further aspect, the complex has a structure represented by a formula selected from:

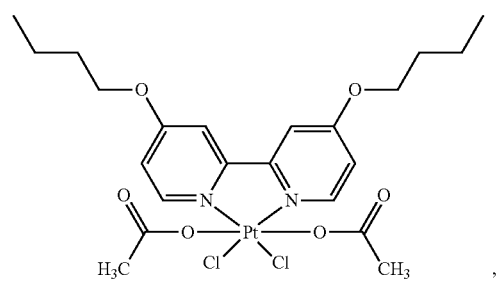

-continued

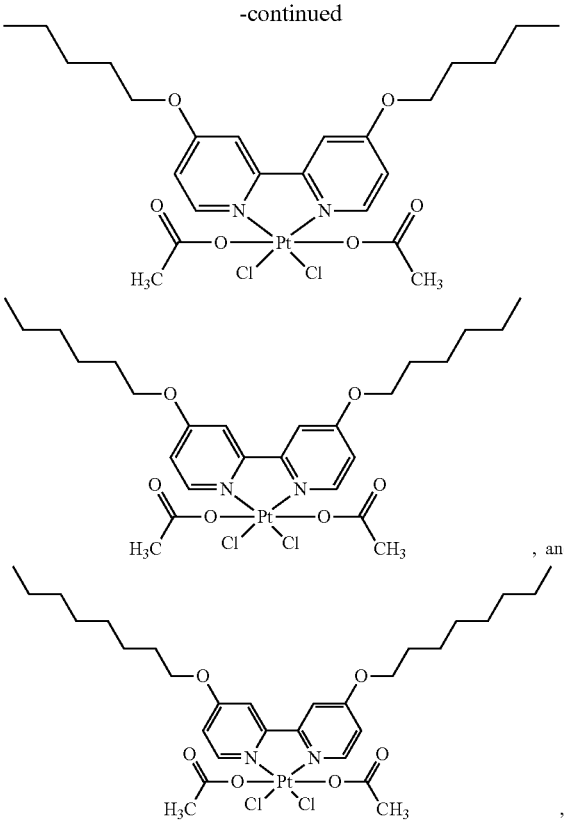

or a pharmaceutically acceptable derivative thereof.

In a further aspect, the complex is:

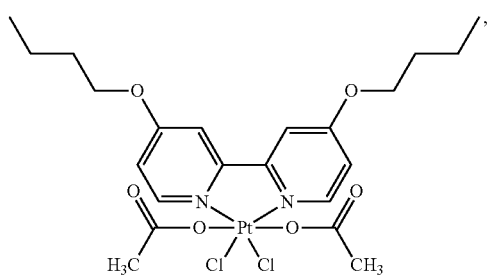

or a pharmaceutically acceptable derivative thereof.

In a further aspect, the complex is:

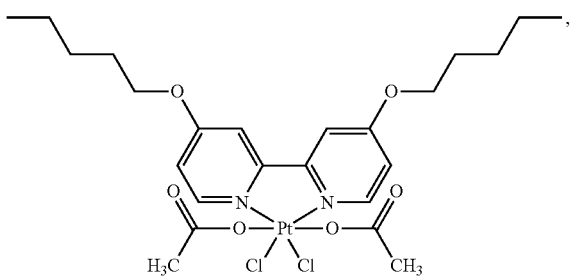

or a pharmaceutically acceptable derivative thereof.

In a further aspect, the complex is:

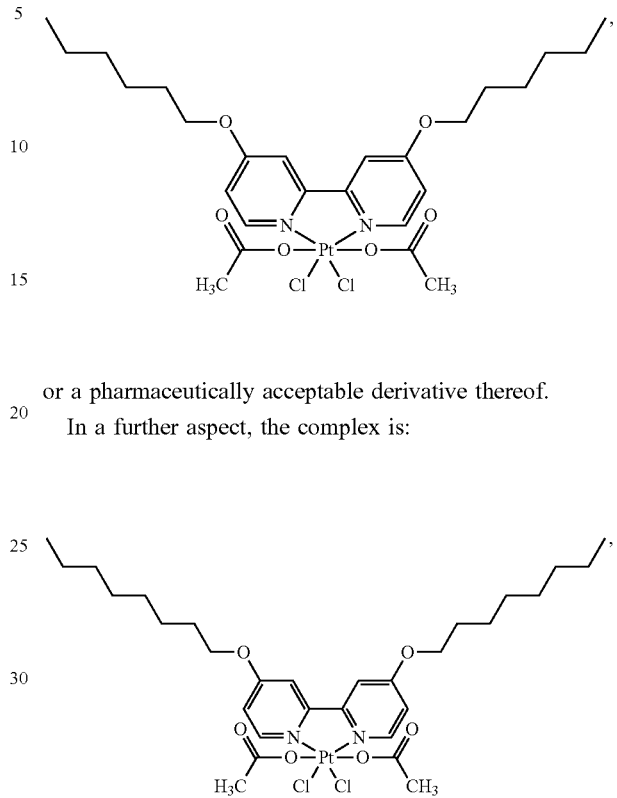

or a pharmaceutically acceptable derivative thereof.

In a further aspect, the complex is:

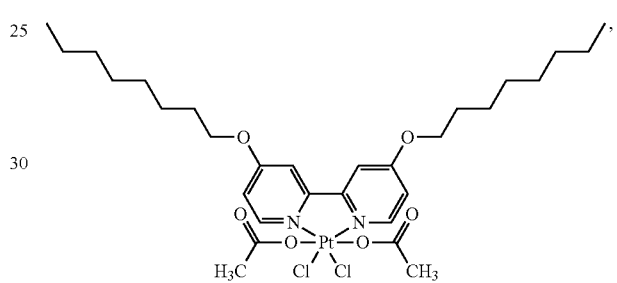

or a pharmaceutically acceptable derivative thereof.

2. Manufacture of a Medicament

In one aspect, the invention relates to a method for the manufacture of a medicament for treatment of a cancer in a mammal comprising combining a therapeutically effective amount of a disclosed complex or product of a disclosed method with a pharmaceutically acceptable carrier or diluent.

In a further aspect, the cancer is a leukemia. In a still further aspect, the cancer is a myeloma. In a yet further aspect, cancer is a solid tumor. In an even further aspect, the cancer is a lymphoma.

In a further aspect, the cancer is selected from cancers of the blood, brain, prostate, genitourinary tract, gastrointestinal tract, colon, rectum, breast, livery, kidney, lymphatic system, stomach, lung, pancreas, and skin. In an even further aspect, the cancer is selected from a cancer of the colon, rectum, breast, prostate, liver, skin and lung. In a still further aspect, the cancer is selected from a cancer of the breast, ovary, testes and prostate. In a yet further aspect, the cancer is a cancer of the breast. In various aspects, the cancer is a cancer of the liver. In a still further aspect, the cancer is a cancer of the prostate. In a yet further aspect, the cancer is a cancer of the colon or rectum.

3. Use of Complexes

In one aspect, the invention relates to the use of a complex having a structure represented by a formula:

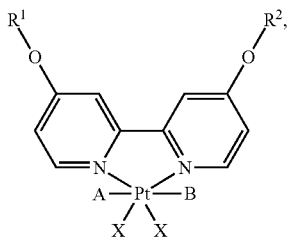

wherein each of $R^1$ and $R^2$ is independently selected from —$(CH_2)_nCH_3$, —$(CH_2)_nOCH_3$, and —$(CH_2)[O(CH_2)_m]_yO(CH_2)_zCH_3$; wherein n is selected from 1, 2, 3, 4, 5, 6, 7, 8, 9, and 10; wherein each of m, y, and z is independently selected from 0, 1, 2, 3, 4, 5, 6, 7, 8, 9, and 10; wherein each X is independently —Br, —Cl, or —I; and wherein each of A and B is independently selected from —Br, —Cl, —I, —OH, and —OC(O)$R^3$; wherein $R^3$ is —$(CH_2)_pCH_3$; and wherein p is selected from 0, 1, 2, 3, 4, 5, 6, 7, 8, 9, and 10, or a pharmaceutically acceptable derivative thereof.

In one aspect, the invention relates to the use of a complex having a structure represented by a formula selected from:

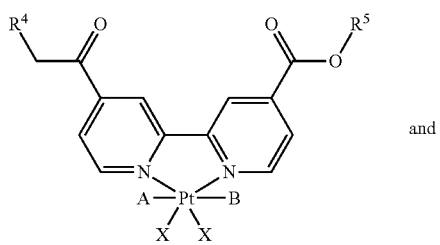

and

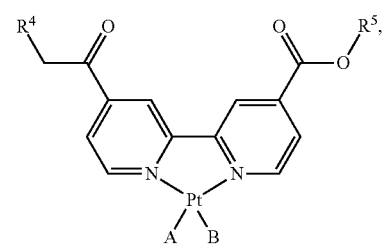

wherein each of $R^4$ and $R^5$ is independently selected from —$(CH_2)_tCH_3$, —$C(CH_3)_3$, —$CH_2CH(CH_2CH_3)CH_2CH_2CH_2CH_3$, —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$; wherein t is selected from 0, 1, 2, 3, 4, 5, 6, and 7; wherein each X is independently —Br, —Cl, or —I; and wherein each of A and B is independently selected from —Br, —Cl, —I, —OH, and —OC(O)$R^3$, provided that A, B, and each X are not simultaneously —Br, simultaneously —Cl, or simultaneously —I; wherein $R^3$ is —$(CH_2)_pCH_3$; and wherein p is selected from 0, 1, 2, 3, 4, 5, 6, 7, 8, 9, and 10, or a pharmaceutically acceptable derivative thereof.

In one aspect, the invention relates to the use of a complex having a structure represented by a formula selected from:

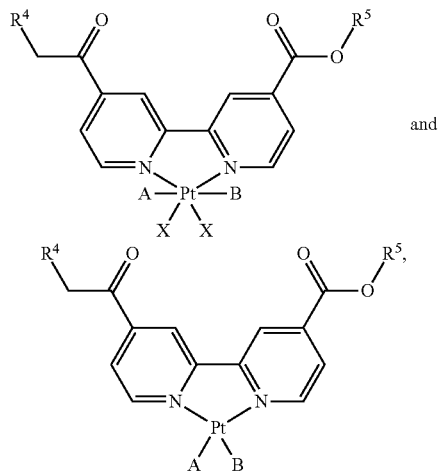

wherein each of $R^4$ and R is independently selected from —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$; wherein t is selected from 0, 1, 2, 3, 4, 5, 6, and 7; wherein each X is independently —Br, —Cl, or —I; and wherein each of A and B is independently selected from —Br, —Cl, —I, —OH, and —OC(O)$R^3$; wherein $R^3$ is —$(CH_2)_pCH_3$; and wherein p is selected from 0, 1, 2, 3, 4, 5, 6, 7, 8, 9, and 10, or a pharmaceutically acceptable derivative thereof.

In a further aspect, the invention relates to the use of at least one disclosed complex for administration to a subject; wherein the subject has a cancer.

In a still further aspect, the use is therapeutic treatment of a mammal. In a yet further aspect, the mammal is human.

In a further aspect, the cancer is a leukemia. In a still further aspect, the cancer is a myeloma. In a yet further aspect, cancer is a solid tumor. In an even further aspect, the cancer is a lymphoma.

In a further aspect, the cancer is selected from cancers of the blood, brain, prostate, genitourinary tract, gastrointestinal tract, colon, rectum, breast, livery, kidney, lymphatic system, stomach, lung, pancreas, and skin. In an even further aspect, the cancer is selected from a cancer of the colon, rectum, breast, prostate, liver, skin and lung. In a still further aspect, the cancer is selected from a cancer of the breast, ovary, testes and prostate. In a yet further aspect, the cancer is a cancer of the breast. In various aspects, the cancer is a cancer of the liver. In a still further aspect, the cancer is a cancer of the prostate. In a yet further aspect, the cancer is a cancer of the colon or rectum.

4. Kits

In one aspect, the invention relates to a kit comprising at least one complex having a structure represented by a formula:

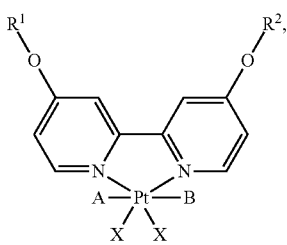

wherein each of $R^1$ and $R^2$ is independently selected from —$(CH_2)_nCH_3$, —$(CH_2)_nOCH_3$, and —$(CH_2)_n[O(CH_2)_m]_yO(CH_2)_zCH_3$; wherein n is selected from 1, 2, 3, 4, 5, 6, 7, 8, 9, and 10; wherein each of m, y, and z is independently selected from 0, 1, 2, 3, 4, 5, 6, 7, 8, 9, and 10; wherein each X is independently —Br, —Cl, or —I; and wherein each of A and B is independently selected from —Br, —Cl, —I, —OH, and —OC(O)$R^3$; wherein $R^3$ is —$(CH_2)_pCH_3$; and wherein p is selected from 0, 1, 2, 3, 4, 5, 6, 7, 8, 9, and 10, or a pharmaceutically acceptable derivative thereof, and one or more of: at least one agent known to treat cancer; or instructions for treating cancer.

In one aspect, the invention relates to a kit comprising at least one complex having a structure represented by a formula selected from:

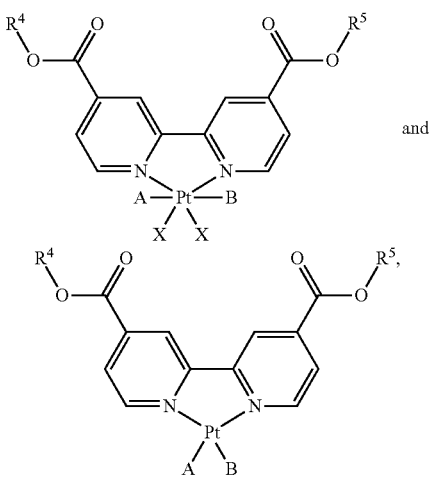

and wherein each of $R^4$ and $R^5$ is independently selected from —$(CH_2)_tCH_3$, —$C(CH_3)_3$, —$CH_2CH(CH_2CH_3)CH_2CH_2CH_2CH_3$, —$(CH_2CH_2O)_2CH_2CH_3$, —$(CH_2CH_2O)_3 CH_2CH_3$, —$(CH_2CH_2O)_3(CH_2)_3CH_3$, and —$(CH_2CH_2O)_4 CH_3$; wherein t is selected from 0, 1, 2, 3, 4, 5, 6, and 7; wherein each X is independently —Br, —Cl, or —I; and wherein each of A and B is independently selected from —Br, —Cl, —I, —OH, and —OC(O)$R^3$, provided that A, B, and each X are not simultaneously —Br, simultaneously —Cl, or simultaneously —I; wherein $R^3$ is —$(CH_2)_pCH_3$; and wherein p is selected from 0, 1, 2, 3, 4, 5, 6, 7, 8, 9, and 10, or a pharmaceutically acceptable derivative thereof, and one or more of: at least one agent known to treat cancer; or instructions for treating cancer.

In one aspect, the invention relates to a kit comprising at least one complex having a structure represented by a formula selected from:

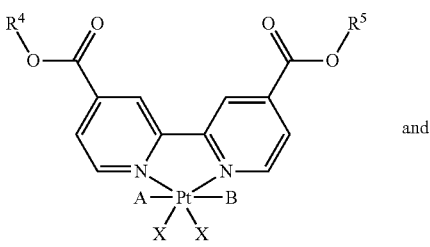

and

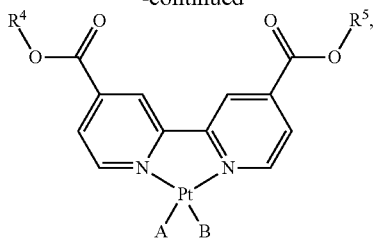

wherein each of $R^4$ and $R^5$ is independently selected from —$(CH_2CH_2O)_2CH_2CH_3$, —$(CH_2CH_2O)_3CH_2CH_3$, —$(CH_2CH_2O)_3(CH_2)_3CH_3$, and —$(CH_2CH_2O)_4CH_3$; wherein t is selected from 0, 1, 2, 3, 4, 5, 6, and 7; wherein each X is independently —Br, —Cl, or —I; and wherein each of A and B is independently selected from —Br, —Cl, —I, —OH, and —OC(O)$R^3$; wherein $R^3$ is —$(CH_2)_pCH_3$; and wherein p is selected from 0, 1, 2, 3, 4, 5, 6, 7, 8, 9, and 10, or a pharmaceutically acceptable derivative thereof, and one or more of: at least one agent known to treat cancer; or instructions for treating cancer.

In a further aspect, the complex of the kit is a disclosed complex or a product of a disclosed method of making a complex.

In a further aspect, the at least one complex and the at least one agent are co-formulated. In a still further aspect, the at least one complex or the at least one product and the at least one agent are co-packaged.

In a further aspect, the at least one agent is a hormone therapy agent. In a yet further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the at least one agent is a chemotherapeutic agent. In a yet further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

In a further aspect, the mTor inhibitor agent is selected from one or more of the group consisting of everolimus, siroliumus, and temsirolimus, or a pharmaceutically acceptable salt, hydrate, solvate, or polymorph thereof.

In a further aspect, the disorder of uncontrolled cellular proliferation is associated with a β-catenin/Tcf protein-protein interaction dysfunction. In a still further aspect, the disorder of uncontrolled cellular proliferation is a cancer. In an even further aspect, cancer is a leukemia. In a still further aspect, the cancer is a sarcoma. In a yet further aspect, cancer is a solid tumor. In an even further aspect, the cancer is a lymphoma. In a still further aspect, the cancer is selected from chronic lymphocytic leukemia, small lymphocytic lymphoma, B-cell non-Hodgkin lymphoma, and large B-cell lymphoma. In a yet further aspect, the cancer is selected from cancers of the blood, brain, genitourinary tract, gastrointestinal tract, colon, rectum, breast, livery, kidney, lymphatic system, stomach, lung, pancreas, and skin. In an even further aspect, the cancer is selected from a cancer of the lung and liver. In a still further aspect, the cancer is selected from a cancer of the breast, ovary, testes and prostate. In a yet further aspect, the cancer is a cancer of the breast. In various aspect, the cancer is a cancer of the ovary. In a still further aspect, the cancer is a cancer of the prostate. In a yet further aspect, the cancer is a cancer of the testes.

In a further aspect, the instructions further comprise providing the complex in connection with a surgical procedure. In a still further aspect, the instructions provide that surgery is performed prior to the administering of at least one complex. In yet a further aspect, the instructions provide that surgery is performed after the administering of at least one complex. In an even further aspect, the instructions provide that the administering of at least one complex is to effect presurgical debulking of a tumor. In a still further aspect, the instructions provide that the administering of at least one complex is to effect presurgical debulking of a tumor.

In a further aspect, the instructions further comprise providing the complex in connection with radiotherapy. In a still further aspect, the instructions provide that radiotherapy is performed prior to the administering of at least one complex. In yet a further aspect, the instructions provide that radiotherapy is performed after the step of the administering of at least one complex. In an even further aspect, the instructions provide that radiotherapy is performed at about the same time as the step of the administering of at least one complex.

In a further aspect, the instructions further comprise providing the complex in connection with at least one agent that is a chemotherapeutic agent.

F. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way.

1. Materials and Methods

All starting materials and reagents for the synthetic procedures were purchased from commercial vendors (Sigma-Aldrich, TCI, Alfa-Aesar, or Acros) unless otherwise noted. They were of high purity and were used without further purification unless noted in the procedure. [Pt(II)Cl$_2$(4,4'-dialkoxy-2,2'-bipyridine)] complexes were synthesized as described herein. Minimum essential medium (MEM), fetal bovine serum (FBS), phosphate buffered saline (PBS), trypsin-EDTA, and penicillin-streptomycin were purchased from Life Technologies (Carlsbad, Calif.). RPMI 1640 medium was purchased from ATCC (Manassas, Va.). Cisplatin (CDDP), carboplatin, HEPES, albumin from bovine serum (BSA), propidium iodide, Hoechst 33342, methanol, and dimethyl sulfoxide (DMSO) were purchased from Sigma-Aldrich. All reagents and enzymes used for flow cytometry were of analytical grade qualities and were purchased from Sigma-Aldrich, unless otherwise noted.

All NMR spectra were obtained utilizing a Varian spectrometer at 298 K or the indicated temperature using deuterated DMSO (DMSO-d$_6$) or chloroform (CDCl$_3$) as the solvents: $^1$H NMR, 400 MHz; and $^{13}$C NMR, 100 MHz. Either residual solvent or tetramethylsilane (TMS) were used as the internal chemical shift reference. Thermal transitions were determined by using a TA Instruments DSC 2010 differential scanning calorimeter in nitrogen at heating and cooling rates of 10° C./min. The temperature axis of the DSC thermogram was calibrated with reference standards of high purity indium and tin before use. An amount of 2-3 mg of the compounds was used for measurements. The T$_{onset}$ and T$_{max}$ temperatures of a melting endotherm of a compound were recorded from the DSC thermogram as Mp (T$_{onset}$-T$_{max}$). Elemental analysis was determined by NuMega Resonance Labs Inc. (San Diego, Calif.) using a Perkin Elmer PE2400-Series II with a CHNS/O analyzer.

1. Synthesis of 4,4'-bis[RO]-2,2'-bipyridine Ligands

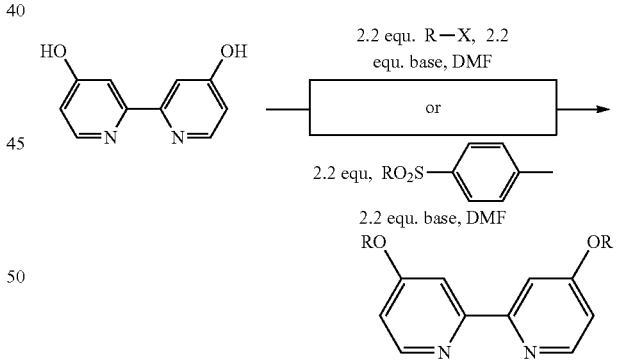

The 4,4'-bis[RO]-2,2'-bipyridine ligands were synthesized as shown above. The alkyl halide or alkyl tosylate containing the desired alkyl group (2.2 equiv.) was added to a mixture of 2,2'-bipyridine-4,4'-diol (1 equiv.) and K$_2$CO$_3$ or Cs$_2$CO$_3$ (2.2 equiv.) in DMF at ~60° C. The suspension was heated to reflux for 48 hours and then allowed to cool to ambient temperature. The salt was removed by vacuum filtration and washed with dimethylformamide (DMF). A rotary evaporator was used to remove the solvent from the filtrate. The solid residue was washed with water and collected by vacuum filtration. In most cases, recrystallization in the appropriate solvent revealed the pure product as shiny, white crystals.

2. Synthesis of Ligands L-COOC$_1$ to L-COOC$_4$

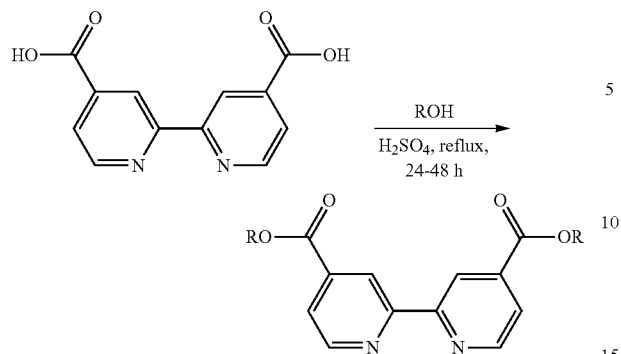

The 4,4'-bis[C(O)OR]-2,2'-bipyridine ligands (L-COOC$_1$ to L-COOC$_4$) were synthesized as described elsewhere for the synthesis of L-COOC$_1$ (Liu et al., Polymer 52:3318-3324, 2011), with slight modifications of the procedure. Briefly, concentrated sulfuric acid (20.4 equiv) was slowly added to a suspension of 4,4'-dicarboxylic acid-2,2'-bipyridine (1 equiv) in the desired alcohol (~25 ml of alcohol per 1 g of diacid used). Once the heat subsided, the reaction mixture was refluxed for 24 hours. At the end of the reaction, the volume of the resulting bright, hot pink solution was reduced using a rotary evaporator. The crude product was precipitated out in ice water and neutralized with a 40% NaOH solution. The pure product was obtained by recrystallization in ethanol, unless otherwise noted.

a. L-COOC$_1$

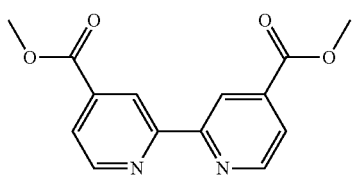

Yield: 86%. Mp=210.0° C. [lit. mp=210-211° C. (Case, J Am Chem Soc 68:2574-2577, 1946). $^1$H NMR (298 K, 400 MHz, DMSO-d$_6$): δ (ppm)=8.94 (d, J=4.9 Hz, 1H), 8.85 (d, J=0.6 Hz, 1H), 7.93 (dd, J=5.0, 1.7 Hz, 1H), 3.97 (s, 3H).

b. L-COOC$_2$

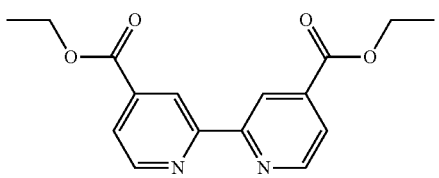 [SMILES: CCOC(=O)c1ccnc(-c2cc(C(=O)OCC)ccn2)c1]

Yield: 90%. Mp=161.5° C. [lit. mp=157° C. (Bellusci et al., Inorg Chem 44:1818-1825, 2005). $^1$H NMR (298 K, 400 MHz, CDCl$_3$): δ (ppm)=8.95 (dd, J=1.6, 0.9 Hz, 1H), 8.87 (dd, J=5.0, 0.9 Hz, 1H), 7.92 (dd, J=5.0, 1.6 Hz, 1H), 4.46 (q, 2H), 1.45 (t, 3H).

c. L-COOC$_3$

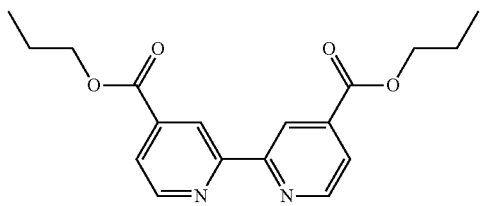 [SMILES: CCCOC(=O)c1ccnc(-c2cc(C(=O)OCCC)ccn2)c1]

Yield: 59%. Mp=114.5° C. $^1$H NMR (298 K, 400 MHz, CDCl$_3$): δ (ppm)=8.95 (dd, J=1.6, 0.9 Hz, 1H), 8.87 (dd, J=5.0, 0.9 Hz, 1H), 7.91 (dd, J=5.0, 1.6 Hz, 1H), 4.37 (t, 2H), 1.92-1.80 (m, 2H), 1.06 (t, 3H). $^{13}$C NMR (298 K, 100 MHz, CDCl$_3$): δ (ppm)=165.17, 156.49, 150.03, 138.95, 123.18, 120.53, 67.39, 22.00, 10.42. Anal. calcd for C$_{18}$H$_{20}$N$_2$O$_4$ (328.36 g mol$^{-1}$): C, 65.84; H, 6.14; N, 8.53%; found: C, 66.29; H, 6.57; N, 8.73%.

d. L-COOC$_4$

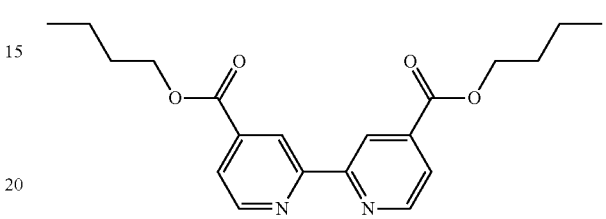

Yield: 52%, white crystals (column chromatography: chloroform). Mp=112.9° C. [lit. mp=108-110° C. (Bos et al., Synthetic Communications 9:497-504, 1979). $^1$H NMR (298 K, 400 MHz, CDCl$_3$): δ (ppm)=8.92 (dd, J=1.6, 0.9 Hz, 1H), 8.85 (dd, J=5.0, 0.9 Hz, 1H), 7.88 (dd, J=5.0, 1.6 Hz, 1H), 4.38 (t, 2H), 1.83-1.72 (m, 2H), 1.48 (m, 2H), 0.98 (t, 3H).

3. Synthesis of Ligands L-COOC$_5$ to L-COOC$_8$

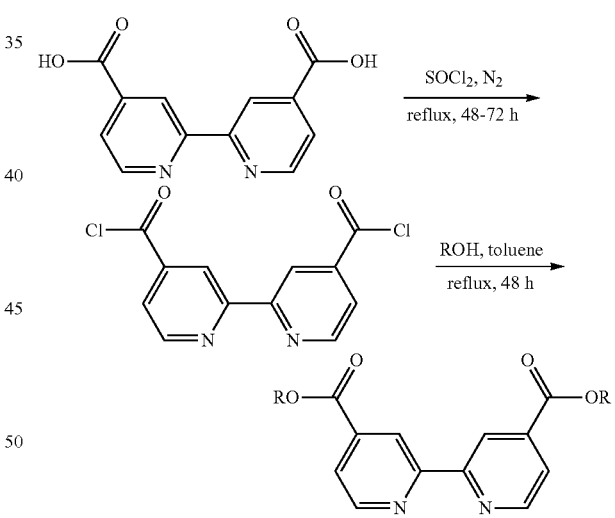

Figure 4A:
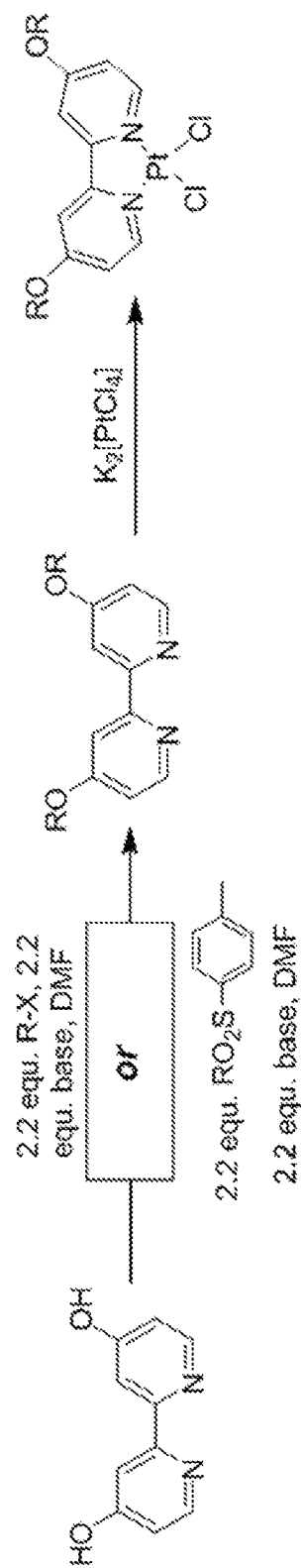
Figure 4B:
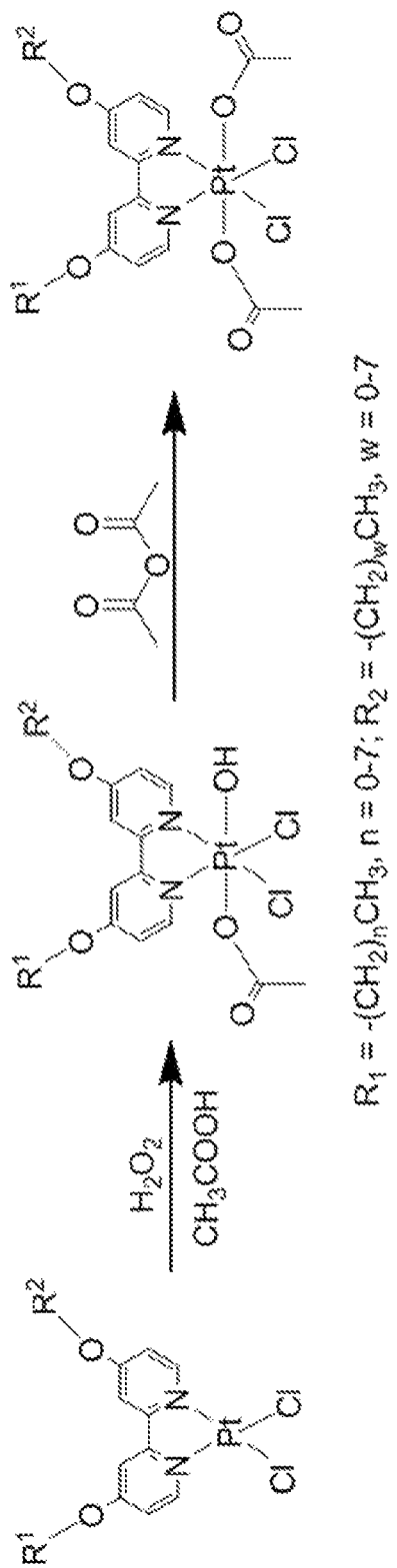
FIG. 4B shows a reaction scheme for making Pt(IV) complexes containing alkoxy groups.
Figure 4C:
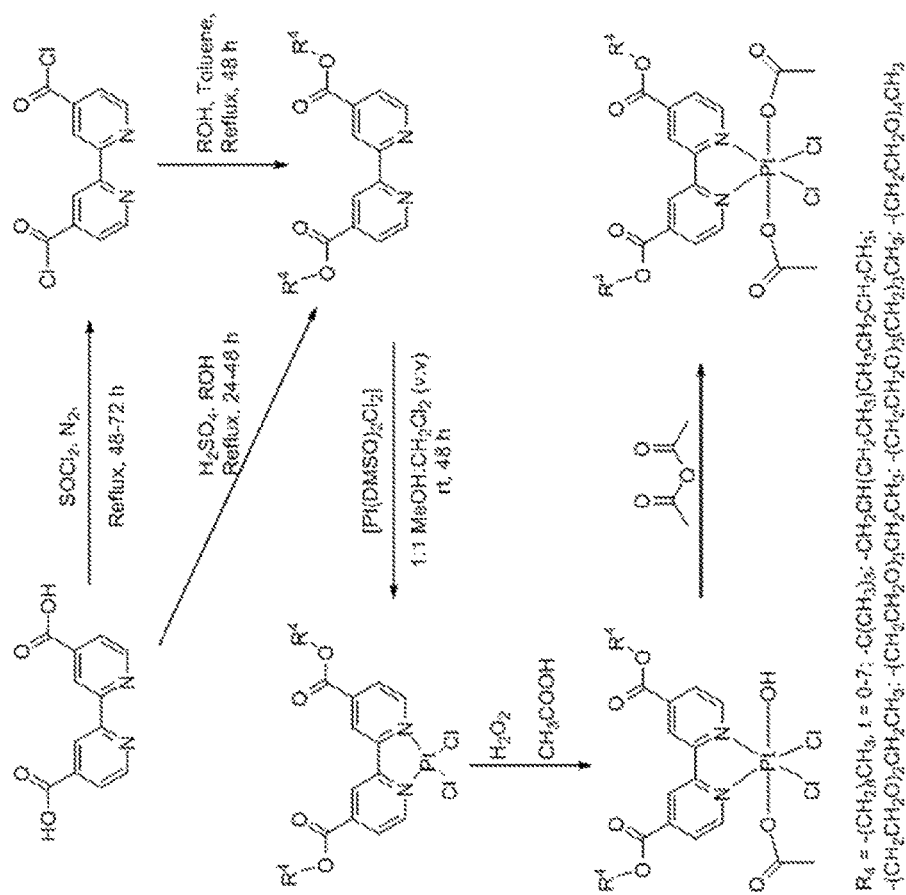
FIG. 4C shows a reaction scheme for making Pt(II) and Pt(IV) complexes containing ester groups.

The procedure for synthesizing the 4,4'-bis[C(O)OR]-2,2'-bipyridine ligands, (L-COOC$_5$ to L-COOC$_8$) was adapted from the synthetic procedure of L-COOC$_8$ described elsewhere (Pucci et al., Mol Cryst Liq Cryst 395:325-335, 2003) (FIG. 4C). Thionyl chloride (25-30 mL) was added to a flask containing 4,4'-dicarboxylic acid-2,2'-bipyridine (3.28 mmol, 1 equiv.) and the mixture was refluxed under nitrogen until a clear yellow solution was obtained. The excess thionyl chloride was removed and the residue was dried overnight in vacuo. The residue was suspended in toluene (~24 mL) and a slight excess of the desired alcohol (3.94 mmol, 1.2 equiv,) was added. The mixture was heated at reflux for 24-48 hours until a weakly pink solution was obtained. The crude product was isolated by extraction with CHCl$_3$ and the mixture was washed with a solution of NaHCO$_3$. The organic layer was washed with water, dried over Na$_2$SO$_4$, filtered, and evaporated to dryness with a rotary evaporator. The pure product was obtained by recrystallization with ethanol, which yielded colorless crystals.

a. L-COOC$_5$

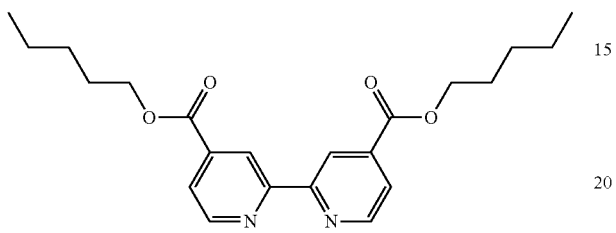

Yield: 66%. Mp=73.3° C. $^1$H NMR (298 K, 400 MHz, CDCl$_3$): δ (ppm)=8.95 (dd, J=1.6, 0.9 Hz, 1H), 8.87 (dd, J=4.9, 0.9 Hz, 1H), 7.90 (dd, J=5.0, 1.6 Hz, 1H), 4.40 (t, 2H), 1.87-1.76 (m, 2H), 1.51-1.33 (m, 4H), 0.95 (t, 3H). $^{13}$C NMR (298 K, 100 MHz, CDCl$_3$): δ (ppm)=165.16, 156.51, 150.03, 138.93, 123.14, 120.50, 65.98, 28.28, 28.04, 22.30, 13.92. Anal. calcd for C$_{22}$H$_{28}$N$_2$O$_4$ (384.47 g mol$^{-1}$): C, 68.73; H, 7.34; N, 7.29%; found: C, 68.33; H, 7.80; N, 7.39%.

b. L-COOC$_6$

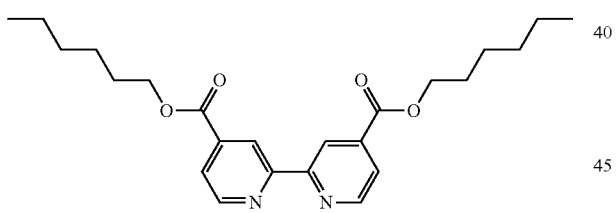

Yield: 65%. Mp=76.91° C. $^1$H NMR (298 K, 400 MHz, CDCl3): δ (ppm)=8.95 (dd, J=1.6, 0.9 Hz, 1H), 8.87 (dd, J=5.0, 0.9 Hz, 1H), 7.90 (dd, J=4.9, 1.6 Hz, 1H), 4.40 (t, 2H), 1.88-1.75 (m, 2H), 1.53-1.42 (m, 2H), 1.42-1.28 (m, 4H), 0.96-0.87 (m, 3H). $^{13}$C NMR (298 K, 100 MHz, CDCl$_3$): δ (ppm)=165.17, 156.51, 150.03, 138.94, 123.15, 120.51, 66.01, 31.40, 28.55, 25.58, 22.49, 13.95. Anal. calcd for C$_{24}$H$_{32}$N$_2$O$_4$ (412.52 g mol$^{-1}$): C, 69.88; H, 7.82; N, 6.79%; found: C, 69.78; H, 8.23; N, 6.96%.

c. L-COOC$_7$

Yield: 58%. Mp=59.4° C. $^1$H NMR (298 K, 400 MHz, CDCl$_3$): δ (ppm)=8.94 (dd, J=1.6, 0.9 Hz, 1H), 8.86 (dd, J=5.0, 0.9 Hz, 1H), 7.90 (dd, J=5.0, 1.6 Hz, 1H), 4.39 (t, 2H), 1.87-1.75 (m, 2H), 1.51-1.24 (m, 8H), 0.93-0.85 (m, 3H). $^{13}$C NMR (298 K, 100 MHz, CDCl$_3$): δ (ppm)=165.18, 156.52, 150.03, 138.95, 123.15, 120.51, 66.02, 31.67, 28.89, 28.59, 25.88, 22.54, 14.02. Anal. calcd for C$_{26}$H$_{36}$N$_2$O$_4$ (440.50 g mol$^{-1}$): C, 70.88; H, 8.24; N, 6.36%; found: C, 70.47; H, 8.70; N, 6.47%.

d. L-COOC$_8$

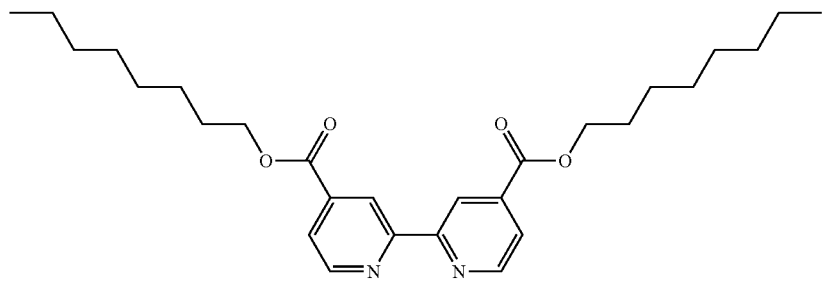 [SMILES: CCCCCCCCOC(=O)c1ccnc(-c2cc(C(=O)OCCCCCCCC)ccn2)c1]

Yield: 81%. Mp=69.4° C. [lit. mp=64° C. (Pucci et al., supra). $^1$H NMR (298 K, 400 MHz, CDCl$_3$): δ (ppm)=8.95 (dd, J=1.6, 0.9 Hz, 1H), 8.87 (dd, J=5.0, 0.9 Hz, 1H), 7.90 (dd, J=5.0, 1.6 Hz, 1H), 4.39 (t, 2H), 1.88-1.75 (m, 2H), 1.52-1.40 (m, 2H), 1.40-1.20 (m, 8H), 0.93-0.84 (m, 3H).

4. Synthesis of Ligand L-COO(C₂O)₂C₂

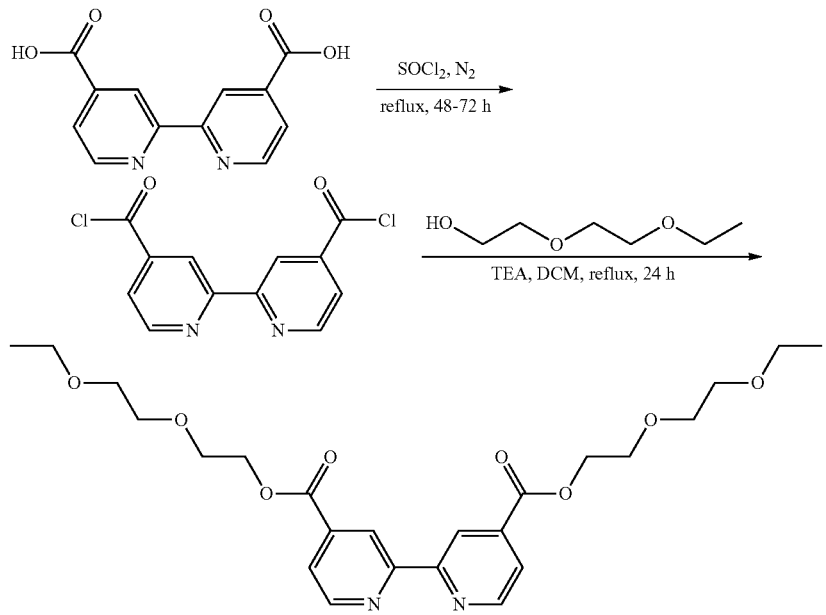

L-COO(C₂O)₂C₂ was synthesized as described elsewhere (Wang et al., *J Supercritical Fluids* 51:181-187, 2009) with slight modifications of the procedure (FIG. 4C). A suspension of 4,4'-dicarboxylic acid-2,2'-bipyridine (3.28 mmol, 1 equiv.) in thionyl chloride (25-30 mL) was refluxed under nitrogen until all the diacid dissolved yielding a clear, light yellow solution (36-72 hours). A rotary evaporator was used to remove the excess thionyl chloride, and the light yellow solid was dried in vacuo at room temperature overnight. Due to the reactivity of the product, the entire amount was used in next step without further purification. The diacid chloride was dissolved in warm CH₂Cl₂ and slowly added to a solution of 2-(2-ethoxyethoxy)ethanol (8.19 mmol, 2.5 equiv.) and triethylamine (7.21 mmol, 2.2 equiv) in CH₂Cl₂ (20 mL) (CAUTION: flame observed). During addition of the diacid chloride solution, the reaction turned from light yellow to a maroon color prior to reflux. The reaction was refluxed for 24 hours. The product was isolated by extraction using 0.1 M HCl, NaHCO₃ (aq), water, dried over Na₂SO₄, filtered, and evaporated to dryness with a rotary evaporator. Recrystallization from ethanol-hexane yielded the pure product as white solid. Yield: 59% (0.921 g; 1.93 mmol). Mp=72.0° C. (lit. mp=67-68° C.). ¹H NMR (298 K, 400 MHz, CDCl₃): δ (ppm)=8.96 (dd, J=1.6, 0.9 Hz, 1H), 8.85 (dd, J=5.0, 0.9 Hz, 1H), 7.91 (dd, J=5.0, 1.7 Hz, 1H), 4.59-4.52 (m, 2H), 3.92-3.84 (m, 2H), 3.74-3.67 (m, 2H), 3.65-3.48 (m, 4H), 1.19 (t, 3H).

5. Synthesis of Pt (II) Complexes

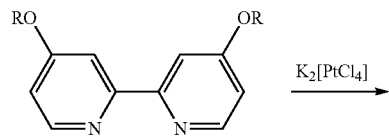

According to the flow scheme shown above, K₂PtCl₄ (tetrachloro platinum 1.2 equiv.) was dissolved in 1-2 mL of H₂O and added to a solution of 4,4'-bisalkoxy-2,2'-bipyridine (1 equiv.) in acetone. The mixture was refluxed for 24 hours. A yellow solid precipitated out either under the refluxing conditions or upon cooling. Water was added to ensure complete precipitation of the [Pt(II)Cl₂(4,4'-bis(RO)-2,2'-bipyridine)] product. Crude products were separated by vacuum filtration, and pure products were obtained by recrystallization or washing with the appropriate solvent.

6. Synthesis of [Pt(DMSO)₂Cl₂]

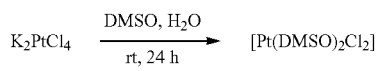

[Pt(DMSO)₂Cl₂] was prepared as described elsewhere (Price et al., supra) with slight modifications of the procedure. K₂[PtCl₄] (1 equiv.) was dissolved in water (5-10 mL) and filtered to removed insoluble impurities. DMSO (4 equiv.) was added to the K₂[PtCl₄] solution and the mixture was stirred at room temperature (protected from light) for 24 hours. The resultant light yellow solid was collected by vacuum filtration, washed with water, and dried in vacuo at 80° C. overnight. Yield: 98%. Mp=230° C. [lit. mp=224-228° C. (Al-Allaf, et al., *Transition Met Chem* 23:403-406, 1998)]. ¹H NMR (298 K, 400 MHz, CDCl₃): δ (ppm)=3.54 (s, 6H). Anal. calcd for C₄H₁₂Cl₂O₂PtS₂ (422.26 g/mol): C, 11.38; H, 2.86; S, 15.19%; found: C, 11.36; H, 2.84; S, 15.20%.

7. Preparation of Ligand-Pt Complexes (Pt(II)-COOC₁— Pt(II)-COOC₈)

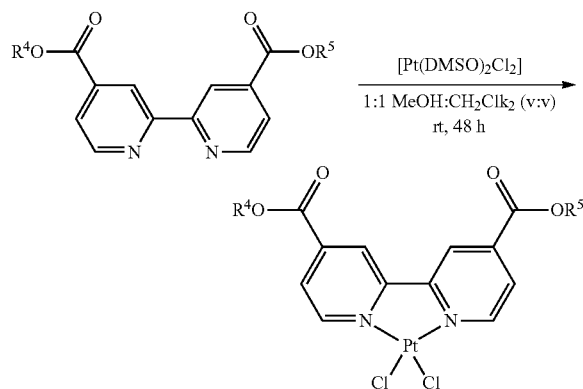

Pt(II)-COOC₁ to Pt(II)-COOC₈ were prepared as described elsewhere (McGarrah and Eisenberg, *Inorg Chem* 42:4355-4365, 2003) with slight modifications of the procedure that resulted in almost quantitative yields. A solution of 1:1 MeOH/CH₂Cl₂ (20-25 mL) was added to an Erlenmeyer flask containing the desired ligand (1.0 equiv.) and [Pt(DMSO)₂Cl₂] (1.0 equiv.). The suspension was protected from light and stirred at room temperature for 24 hours to give an orange solid or solution. The solvent was removed completely using a rotary evaporator and the crude product was dried in vacuo at 50° C. overnight. Unless otherwise noted, the orange solid was dissolved in CH₂Cl₂ and the solution was filtered through Celite. The solvent was removed using a rotary evaporator resulting in shiny orange solids. The product was dried in vacuo overnight.

a. Pt(II)-COOC₁

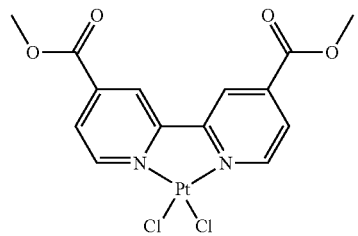

Mp=316.4° C. decomposed [lit. mp=312° C. decomposed; Allenbaugh et al., *Chem Mater* 24:4517-4530, 2012; was not filtered through Celite). ¹H NMR (298 K, 400 MHz, DMSO-d₆): δ (ppm)=9.65 (d, J=6.1 Hz, 1H), 9.05 (d, J=1.9 Hz, 1H), 8.23 (dd, J=6.0, 1.8 Hz, 1H), 4.00 (s, 3H). ¹³C NMR (298 K, 400 MHz, DMSO-d₆): δ (ppm)=164.14, 157.75, 150.07, 140.59, 127.64, 124.36, 53.81. Anal. Calcd for C₁₄H₁₂Cl₂N₂O₄Pt (538.25 g mol⁻¹): C, 31.24; H, 2.25; N, 5.20%; found: C, 30.97; H, 2.36; N, 5.20%.

b. Pt(II)-COOC₂

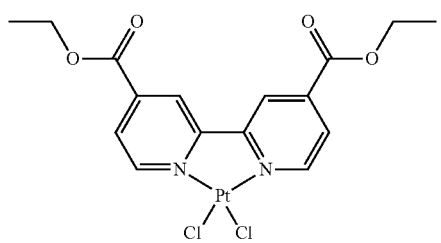

Mp=339.3° C. decomposed [lit. mp=335° C. decomposed (Allenbaugh et al., supra). ¹H NMR (298 K, 400 MHz, CDCl₃): δ (ppm)=9.73 (d, J=6.0 Hz, 1H), 8.60 (s, 1H), 8.06 (dd, J=6.1, 1.7 Hz, 1H), 4.55 (q, J=7.1 Hz, 2H), 1.51 (t, J=7.1 Hz, 3H). ¹³C NMR (298 K, 400 MHz, CDCl₃): δ (ppm)= 162.94, 157.42, 150.03, 140.38, 126.82, 123.18, 63.25, 14.21. Anal. Calcd. for C₁₆H₁₆Cl₂N₂O₄Pt (566.30 g mol⁻¹): C, 33.93; H, 2.85; N, 4.95%; found: C, 33.87; H, 3.09; N, 5.15%.

c. Pt(II)-COOC₄

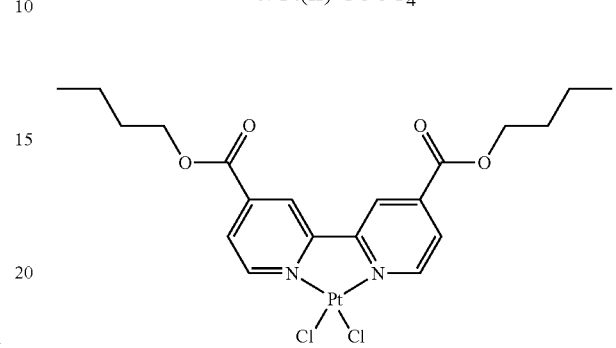

¹H NMR (298 K, 400 MHz, CDCl₃): δ (ppm)=9.78 (dd, J=6.0, 0.6 Hz, 1H), 8.59 (dd, J=1.8, 0.7 Hz, 1H), 8.07 (dd, J=6.0, 1.8 Hz, 1H), 4.49 (t, 2H), 1.92-1.81 (m, 2H), 1.52 (m, 2H), 1.04 (t, 3H).

d. Pt(II)-COOC₅

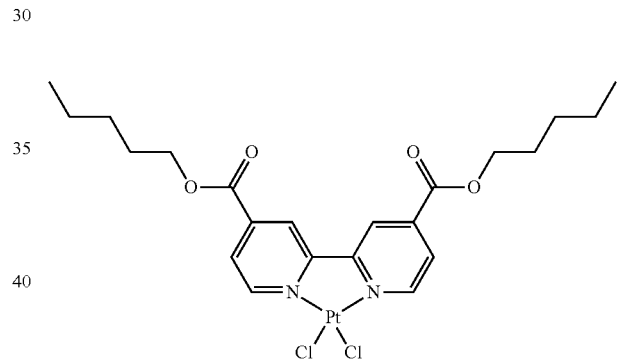

¹H NMR (298 K, 400 MHz, CDCl₃): δ (ppm)=9.74 (dd, J=6.1, 0.6 Hz, 1H), 8.58 (d, J=1.5 Hz, 1H), 8.05 (dd, J=6.0, 1.8 Hz, 1H), 4.47 (t, 2H), 1.93-1.83 (m, 2H), 1.53-1.36 (m, 4H), 1.02-0.92 (m, 3H).

e. Pt(II)-COOC₆

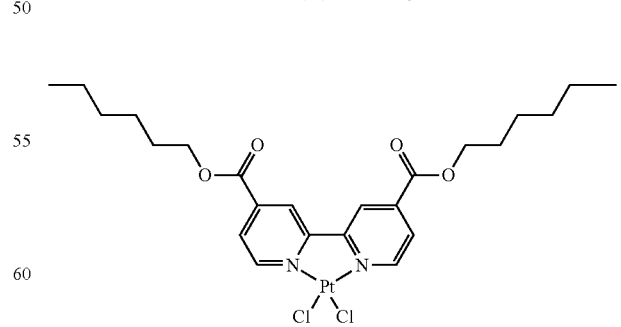

¹H NMR (298 K, 400 MHz, CDCl₃): δ (ppm)=9.73 (dd, J=6.0, 0.6 Hz, 1H), 8.59 (d, J=1.4 Hz, 1H), 8.05 (dd, J=6.0, 1.8 Hz, 1H), 4.47 (t, 2H), 1.87 (p, 2H), 1.55-1.42 (m, 2H), 1.42-1.31 (m, 4H), 0.98-0.88 (m, 3H).

f. Pt(II)-COOC$_7$

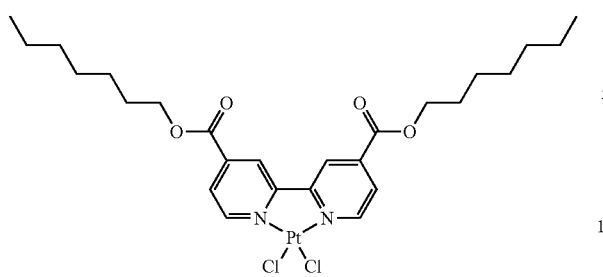

$^1$H NMR (298 K, 400 MHz, CDCl$_3$): δ (ppm)=9.78 (dd, J=6.1, 0.6 Hz, 1H), 8.59 (d, J=1.5 Hz, 1H), 8.07 (dd, J=6.0, 1.8 Hz, 1H), 4.47 (t, 2H), 1.93-1.81 (m, 2H), 1.54-1.29 (m, 8H), 0.96-0.87 (m, 3H).

g. Pt(II)-COOC$_8$

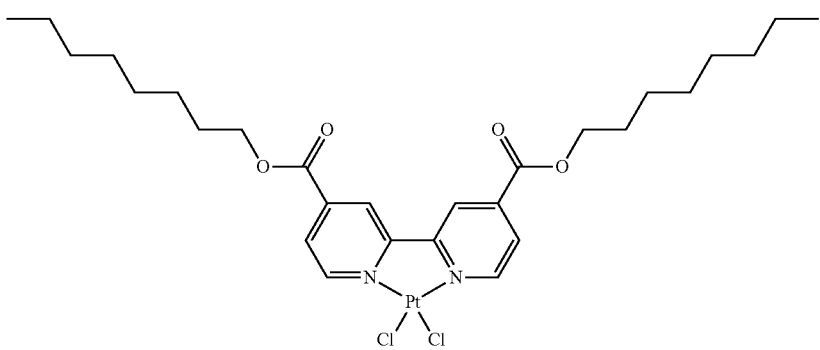

$^1$H NMR Mp=206.5° C. [lit. mp=202.4° C. (Allenbaugh et al., supra). (298 K, 400 MHz, CDCl$_3$): δ (ppm)=9.79 (dd, J=6.1, 0.6 Hz, 1H), 8.60 (d, J=1.5 Hz, 1H), 8.07 (dd, J=6.0, 1.8 Hz, 1H), 4.47 (t, 2H), 1.93-1.81 (m, 2H), 1.54-1.26 (m, 10H), 0.94-0.86 (m, 3H).

8. Preparation of Pt(II)-COO(C$_2$O)$_2$C$_2$

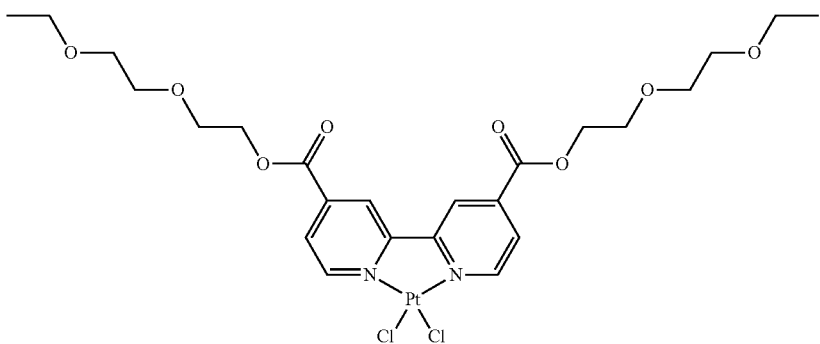

Pt(II)-COO(C$_2$O)$_2$C$_2$, yield 69%, prepared using the same procedure as for the [Pt(II)Cl$_2$ (4,4'-dialkoxy-2,2'-bipyridine)] complexes with further purification using column chromatography (eluent: 20% acetone: 80% chloroform) to obtain the pure product. Mp=106.0° C. $^1$H NMR (298 K, 400 MHz, CDCl$_3$): δ (ppm)=9.60 (d, J=6.1 Hz, 1H), 8.60 (d, J=2.0 Hz, 1H), 8.04 (dd, J=6.0, 1.8 Hz, 1H), 4.65-4.58 (m, 2H), 3.95-3.87 (m, 2H), 3.76-3.69 (m, 2H), 3.66-3.59 (m, 2H), 3.53 (q, 2H), 1.19 (t, 3H). $^{13}$C NMR (298 K, 100 MHz, CDCl$_3$): δ (ppm)=162.95, 157.37, 149.86, 140.09, 126.94, 123.52, 70.77, 69.79, 68.67, 66.67, 65.89, 15.16. Anal. calcd for C$_{24}$H$_{32}$Cl$_2$N$_2$O$_8$Pt (742.51 g mol$^{-1}$): C, 38.82; H, 4.34; N, 3.77%; found: C, 38.96; H, 4.65; N, 3.80%.

9. Synthesis of Pt(IV) Complexes

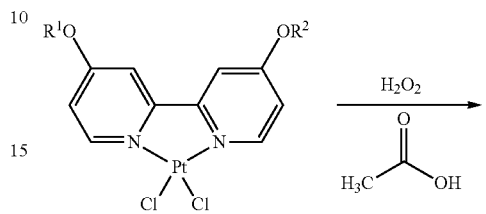

-continued

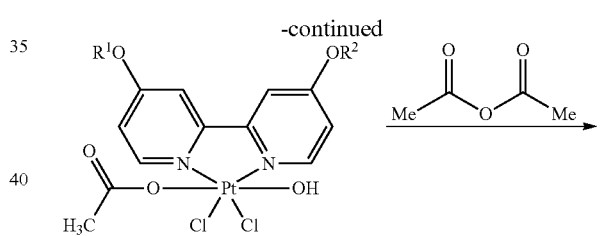

-continued

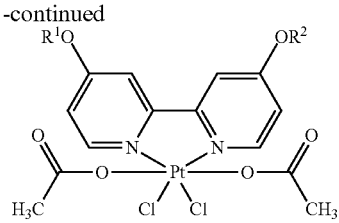

Pt(IV) complexes were prepared from the corresponding Pt(II) complexes as described elsewhere (Mackay et al., supra), with slight modifications of the reaction condition. [Pt(II)Cl$_2$(4,4'-disubstituted-2,2'-bipyridine)] (1 equiv.) was suspended in 40 mL glacial acetic acid (>99%) and H$_2$O$_2$ (30%, 33 equiv.) was added. The bright yellow suspension was protected from light and stirred at 298 K for 24 hours to obtain a light yellow solution. The solvent was removed completely and 30 mL of acetic anhydride was added to the pale yellow residue. A pale yellow suspension was obtained after stirring for 1 to 2 days at 298 K. The solvent was removed and ice-cold H$_2$O was added. The crude product (pale yellow solid) was collected by vacuum filtration. Unless otherwise noted, products were purified by extraction with CHCl$_3$, drying over Na$_2$SO$_4$, removing the solvent with a rotary evaporator, and then drying in vacuo at 80° C.

Seven [Pt(IV)Cl$_2$(OAc)$_2$(4,4'-dialkoxy-2,2'-bipyridine)] complexes were synthesized and characterized by $^1$H NMR, $^{13}$C NMR spectroscopy, elemental analysis, and differential scanning calorimetry (DSC) measurements. The in vitro anti-proliferative activities of these Pt(IV) complexes were examined in a panel of human breast, prostate, and lung cancer cell lines. Comparison of the EC$_{50}$ values showed varying degrees of activities in the ten cell lines tested; however, the Pt(IV) complexes were generally more effective than cisplatin. A structure-activity relationship was observed in which complexes with increasing carbon number on the alkoxy substituents had increasing anti-proliferative activity. These Pt(IV) complexes exhibited improved solubility in organic solvents compared to the Pt(II) precursors.

A. [Pt(IV)Cl$_2$(OAc)$_2$(4,4'-dimethoxy-2,2'-bipyridine)] (Pt(IV)-1C)

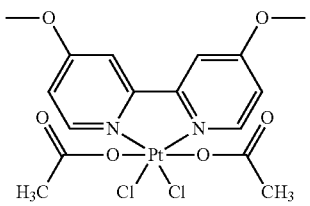

Yield: 87%, pale yellow powder (obtained by washing the crude product with water without further purification). Mp 249° C. (decomposed). $^1$H NMR (298 K, 400 MHz, DMSO-d$_6$): δ (ppm)=9.30 (d, 1H, J=6.9 Hz), 8.37 (s, 1H), 7.58 (d, 1H, J=7.0 Hz), 4.14 (s, 3H), 1.60 (s, 3H). $^{13}$C NMR (298 K, 100 MHz, DMSO-d$_6$): δ (ppm)=174.66, 170.03, 158.03, 149.74, 113.24, 111.20, 58.12, 22.38. Anal. Calcd for C$_{16}$H$_{18}$Cl$_2$N$_2$O$_6$Pt (600.31 g/mol): C, 32.01; H, 3.02; N, 4.67%; found: C, 32.07; H, 3.11; N, 4.61%.

b. [Pt(IV)Cl$_2$(OAc)$_2$(4,4'-diethoxy-2,2'-bipyridine)] (Pt(IV)-2C)

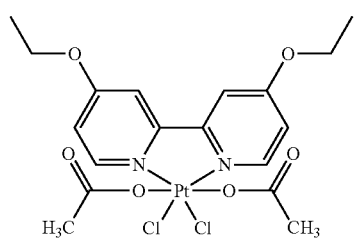

Yield: 90%, pale yellow powder. Mp 260° C. (decomposed). $^1$H NMR (298 K, 400 MHz, DMSO-d$_6$): δ (ppm)=9.27 (d, J=6.9 Hz, 1H), 8.35 (d, J=2.9 Hz, 1H), 7.54 (dd, J=7.0, 2.8 Hz, 1H), 4.43 (q, J=6.8 Hz, 2H), 1.59 (s, 3H), 1.44 (t, J=6.5 Hz, 3H). $^{13}$C NMR (298 K, 100 MHz, DMSO-d$_6$): δ (ppm)=173.79, 168.41, 157.23, 148.83, 112.59, 110.47, 65.85, 21.54, 13.69. Anal. Calcd for C$_{18}$H$_{22}$Cl$_2$N$_2$O$_6$Pt (628.37 g/mol): C, 34.41; H, 3.53; N, 4.46%; found: C, 34.58; H, 3.89; N, 4.59%.

c. [Pt(IV)Cl$_2$(OAc)$_2$(4,4'-dipropoxy-2,2'-bipyridine)] (Pt(IV)-3C)

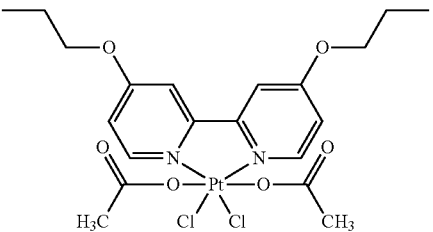

Yield: 64%, pale yellow powder. Mp 243° C. (decomposed). $^1$H NMR (298 K, 400 MHz, DMSO-d$_6$): δ (ppm)= .27 (d, J=7.0 Hz, 1H), 8.37 (d, J=2.9 Hz, 1H), 7.55 (dd, J=7.1, 2.9 Hz, 1H), 4.34 (t, J=6.5 Hz, 2H), 1.90-1.81 (m, 2H), 1.60 (s, 3H), 1.05 (t, J=7.4 Hz, 3H). $^{13}$C NMR (298 K, 100 MHz, DMSO-d$_6$): δ (ppm)=174.66, 169.42, 158.09, 149.69, 113.44, 111.38, 72.12, 22.39, 22.04, 10.62. Anal. Calcd for C$_{20}$H$_{26}$Cl$_2$N$_2$O$_6$Pt (656.42 g/mol): C, 36.59; H, 3.99; N, 4.27%; found: C, 36.47; H, 4.08; N, 4.60%.

d. [Pt(IV)Cl$_2$(OAc)$_2$(4,4'-dibutoxy-2,2'-bipyridine)] (Pt(IV)-4C)

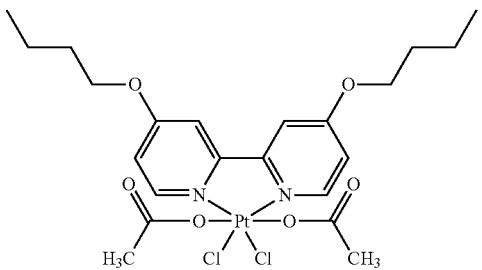

Yield: 67%, pale yellow powder (further purified by recrystallization in CHCl$_3$-hexane). Mp 219° C. (decomposed). $^1$H NMR (298 K, 400 MHz, DMSO-d$_6$): δ (ppm)= 9.25 (d, J=7.0 Hz, $^1$H), 8.34 (d, J=3.0 Hz, $^1$H), 7.54 (dd, J=7.2, 2.8 Hz, 1H), 4.36 (t, J=6.4 Hz, 2H), 1.83-1.76 (m, 2H), 1.58 (s, 3H), 1.53-1.44 (m, 2H), 0.96 (t, J=7.5 Hz, 3H). $^{13}$C NMR (298 K, 100 MHz, DMSO-d$_6$): δ (ppm)=174.67, 169.43, 158.09, 149.69, 113.46, 111.40, 70.45, 30.64, 22.41, 18.99, 14.06. Anal. Calcd for C$_{22}$H$_{30}$Cl$_2$N$_2$O$_6$Pt (684.47 g/mol): C, 38.60; H, 4.42; N, 4.09%; found: C, 38.48; H, 4.75; N, 4.10%.

e. [Pt(IV)Cl₂(OAc)₂(4,4'-dipentoxy-2,2'-bipyridine)] (Pt(IV)-5C)

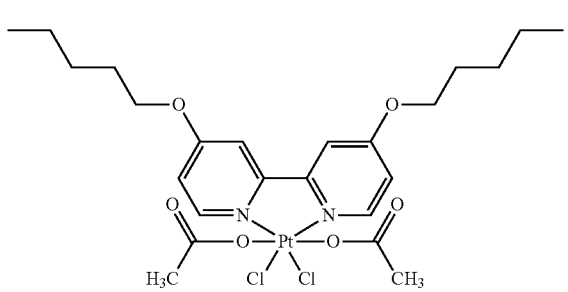

Yield: 92%, pale yellow powder. Mp 222° C. (decomposed). ¹H NMR (298 K, 400 MHz, CDCl₃): δ (ppm)=9.57 (d, J=6.9 Hz, 1H), 7.46 (d, J=2.8 Hz, 1H), 7.16 (dd, J=7.0, 2.7 Hz, 1H), 4.20 (t, J=6.4 Hz, 2H), 1.91-1.84 (m, 2H), 1.82 (s, 3H), 1.54-1.34 (m, 4H), 0.96 (t, J=7.1 Hz, ³H). ¹³C NMR (298 K, 100 MHz, CDCl₃): δ (ppm)=177.23, 169.18, 158.72, 150.21, 111.62, 110.01, 70.49, 28.46, 28.03, 22.90, 22.43, 14.05. Anal. Calcd for C₂₄H₃₄Cl₂N₂O₆Pt (712.53 g/mol): C, 40.46; H, 4.81; N, 3.93%; found: C, 40.46; H, 5.12; N, 4.05%.

f. [Pt(IV)Cl₂(OAc)₂(4,4'-dihexyloxy-2,2'-bipyridine)] (Pt(IV)-6C)

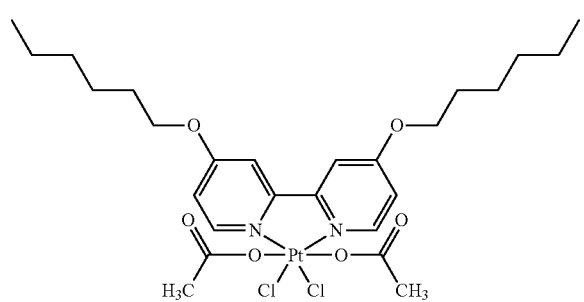

Yield: 74%, pale yellow powder (further purified by recrystallization in acetone-hexane). Mp 219° C. (decomposed). ¹H NMR (298 K, 400 MHz, CDCl₃): δ (ppm)=9.58 (d, J=6.9 Hz, 1H), 7.45 (d, J=2.9 Hz, 1H), 7.15 (dd, J=7.1, 2.9 Hz, 1H), 4.21 (t, J=6.4 Hz, 2H), 1.92-135 1.85 (m, 2H), 1.83 (s, 3H), 1.56-1.43 (m, 2H), 1.42-1.32 (m, 4H), 0.93 (t, J=6.7 Hz, 3H). ¹³C NMR (298 K, 100 MHz, CDCl₃): δ (ppm)=177.12, 169.04, 158.54, 150.09, 111.44, 109.88, 77.32, 77.00, 76.69, 70.35, 31.33, 28.59, 25.46, 22.75, 22.50, 13.96. Anal. Calcd for C₂₆H₃₈Cl₂N₂O₆Pt (740.58 g/mol): C, 42.17; H, 5.17; N, 3.78%; found: C, 42.08; H, 5.44; N, 3.80%.

g. [Pt(IV)Cl₂(OAc)₂(4,4'-dioctyloxy-2,2'-bipyridine)] (Pt(IV)-8C)

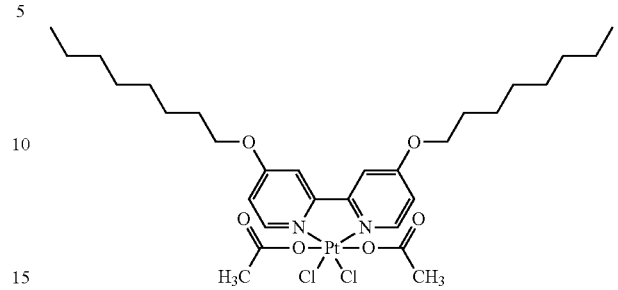

Yield: 85%, pale yellow powder (further purified by recrystallization in acetone-hexane). Mp 203° C. (decomposed). ¹H NMR (298 K, 400 MHz, CDCl₃): δ (ppm) 9.57 (d, J=6.9 Hz, 1H), 7.46 (d, J=2.7 Hz, 1H), 7.15 (dd, J=7.0, 2.7 Hz, 1H), 4.20 (t, J=6.4 Hz, 2H), 1.93-1.84 (m, 2H), 1.82 (s, 3H), 1.54-1.43 (m, 2H), 1.43-1.25 (m, 8H), 0.90 (t, J=6.6 Hz, 3H). ¹³C NMR (298 K, 100 MHz, CDCl₃): δ (ppm)= 177.07, 169.04, 158.58, 150.07, 111.47, 109.86, 70.36, 31.73, 29.15, 29.11, 28.63, 25.78, 22.75, 22.61, 14.07. Anal. Calcd for C₃₀H₄₆Cl₂N₂O₆Pt (796.69 g/mol): C, 45.23; H, 5.82; N, 3.52%; found: C, 45.07; H, 6.10; N, 3.55%.

10. Cell Culture

Human breast (HCC38, MCF-7, MDA-MB-231, SK-BR-3, T-47D, and ZR-75-1), lung (A549 and H520), and prostate (DU145 and PC-3) cancer cell lines were obtained from American Culture Type Collection (ATCC). The HCC38, MCF-7, MDA-MB-231, SK-BR-3, T-47D, ZR-75-1, and A549 cells were grown in MEM supplemented with 10% FBS, 25 mM HEPES buffer (pH 7.4), penicillin (100 U/mL), and streptomycin (100 µg/mL). The H520, DU145, and PC-3 cell lines were grown in RPMI-1640 supplemented with 10% FBS, 25 mM HEPES buffer (pH 7.4), penicillin (100 U/mL), and streptomycin (100 µg/mL). All cell lines were maintained at 37° C. in a humidified, 5% CO₂ atmosphere.

11. Cell Viability Assay

Cells were cultured at a density of 2-3.5×10³ cells per well in flat bottomed 96-well plates in 100 µL of complete growth medium and incubated for 2 days to reach ~50% confluence. The cells were then treated with solvent or the appropriate drugs (CDDP stock was dissolved in 0.15 M NaCl, carboplatin stock was dissolved in 5% glucose, synthesized Pt(IV) complexes were dissolved in DMSO) for 1 hour, washed three times with 100 µL PBS, and incubated in 100 µL of fresh medium. After 2 days, the medium was replaced with 120 µL of medium containing CellTiter 96® Aqueous One Solution Reagent (MTS reagent) (Promega, Madison, Wis.). The cells were incubated at 37° C. for 4 hours and the cell viability was determined by measuring the absorbance at 490 nm using a Tecan Infinite M1000 microplate reader. The 48 h treatment was done in a similar manner, except the cells were not washed after treatment and the MTS reagent was immediately added. Viability of treated groups was calculated as a percent of control and graphed with GraphPad Prism.

12. Flow Cytometry—Propidium Iodide (PI) Staining

Cells (~50 to 60% confluent in 60 mm dishes) were treated as indicated with the platinum compound. After treatment, the floating cells were collected, and both attached and floating cells were washed 2× with PBS. The cells were resuspended in fresh medium and incubated as indicated. The cells were harvested (both the floating and attached cells were collected), counted, and pelleted. The cells were then washed two times with 5 mL PBS, fixed by resuspending in 0.1 mL of PBS and 1 mL of ice-cold 95% ethanol with gentle vortexing. Fixed cells were stored at 4° C. until analysis. For analysis, fixed cells were washed once with 1-2 mL of PBS and centrifuged at 500×g for 5 minutes. The cell pellet was resuspended in 100 µL of a 1.0% Triton X-100 buffer solution, and 100 µL of a 1.0 mg/mL RNAse solution was added and allowed to stand at room temperature for 10-15 minutes. While in the dark, 200 µL of a 100 µg/mL PI stain was added to make a final concentration of 50 µg/mL and gently vortexed. The cell mixture was incubated at room temperature for 30 minutes, and flow cytometry acquisition was done on a Becton Dickinson FACS Calibur with the argon laser set at 488 nm on the linear Flow Channel 2 (FL-2) with Doublet Discriminatory Module (DDM) and threshold set on FL-2.

13. Flow Cytometry—Annexin V-FITC/PI Staining

Cells (~50 to 60% confluent in 60 mm dishes) were treated as indicated with the platinum compound. After treatment, the floating cells were collected, and both attached and floating cells were washed 2× with PBS. The cells were resuspended in fresh medium and incubated as indicated. The cells were harvested (both the floating and attached cells were collected), counted, and pelleted. The cells were then washed two times with 5 mL of $Ca^{2+}$ and $Mg^{2+}$ free PBS. The pellets were then washed in 2.0 mL of 1× Annexin-V Binding buffer (BD Bioscience, San Jose, CAS) and centrifuged at 500×g for 5 minutes. The pellets were treated with Annexin-V-FITC conjugate (BD Bioscience, San Jose, Calif.) and incubated in the dark for 15 minutes. Just before acquisition, the volume of cells-conjugate mixture was adjusted by addition of 1× Annexin-V binding buffer. Acquisition to discriminate between apoptotic and necrotic cells was done by staining the cell-conjugate mixture with 10 µL of PI (50 µg/mL) solution (BD Bioscience, San Jose, Calif.). Acquisitions were done on a FACS Calibur Cytometer on the FL1 (Annexin) and FL3 (PI) channels with threshold and Duplet Discriminating Module (DDM) set at FL1. The level of shift in events distribution in the Annexin-V only and Annexin-V-PI populations in comparison to control is indicative of degree of effectiveness of the treatment agents. A quantitative measure of these event shifts was accomplished by gating.

14. Flow Cytometric Immunofluorescence

Cells (200,000 to 250,000) were seeded in 60 mm dishes and incubated at 37° C. in a humidified, 5% CO2 atmosphere for 2 days to reach ~50-60% confluence. The cells were treated with the platinum complexes as indicated, the floating cells were collected, and both attached and floating cells were washed 2× with PBS. The cells were resuspended in fresh medium and incubated as indicated. After incubation, both the floating and attached cells were collected and fixed by incubation in 4% formaldehyde for 10 minutes at room temperature. The fixed cells were pelleted and permeabilized by incubation in 500 µL of ice-cold methanol at 4° C. for 10 minutes. The samples were stored at −20° C. until analysis. For analysis, the cells were pelleted and washed 2× with 1% BSA in PBS. The cells were resuspended in BD Stain Buffer (BS Biosciences #554656) containing the appropriate conjugated primary antibody [PE Mouse Anti-Cleaved PARP (Asp214) and Alexa Fluor 647 Mouse Anti-H2AX (pS139) antibodies were purchased as a part of a Cell Proliferation Kit (BD Biosciences #562253)], and incubated at 4° C. overnight. After washing 2× with 1% BSA, the cells were resuspended in PBS and analyzed on a Becton Dickinson FACS Calibur.

15. Confocal Microscopy

Cells (100,000 to 125,000) were seeded into 35 mm dishes and incubated for 48 hours at 37° C. The cells were treated with control, Pt(IV)-4C, or Pt(IV)-5C, and while in the dark, the cells were washed 2× with 1 mL PBS. After washing, 1 mL of a 2 µg/mL Hoechst 33342 and 10 µg/mL PI solution (in PBS) was added, and the cells were incubated for 15 minutes at room temperature. Images were acquired within 5 minutes with a Nikon A1R confocal laser scanning microscopy system (CLSM) mounted on a Nikon Eclipse Ti. At least three random areas on each dish were imaged.

16. Statistical Analysis

GraphPad Prism was used to graph viability curves. ModFit version 3.0 was used for the flow cytometry analysis. Microsoft Office Excel was used to perform unpaired Student's t-test; values with p<0.05 were considered significant. Student's t-tests were used to verify significant differences among the $EC_{50}$ values.

G. EXAMPLES

1. Synthesis and Characterization

The activity of Pt(IV) complexes are thought to be due to activation by intracellular enzymatic reduction to Pt(II); thus, the reduction potential of the Pt(IV) compound is important. This is governed by the axial ligands; chlorido ligands are most easily reduced, followed by acetato ligands, and hydroxido ligands are the most difficult to reduce (Graf and Lippard, *Adv Drug Deliv Rev* 64:9931004, 2012).

[Pt(II)Cl$_2$(4,4'-dialkoxy-2,2'-bipyridine)] complexes were synthesized as described herein and used as precursors for the synthesis of the Pt(IV) complexes. Pt(IV) complexes of the formula [Pt(IV)Cl$_2$(OAc)$_2$(4,4'-bis(RO)-2,2'-bipyridine)] (where R=—(CH$_2$)$_n$CH$_3$ and n=0-5, 7) were synthesized with yields ranging from 64% to 92% by following the procedure (FIG. 4B) of Mackay et al. (supra) with slight modification of the reaction condition. The Pt(II) precursors were first converted to unsymmetrical Pt(IV) complexes containing a mixture of OH and OAc axial ligands by an oxidation reaction with H$_2$O$_2$ in acetic acid. The progress of the reaction was visually monitored by the disappearance of the insoluble bright yellow solid of the Pt(II) compounds into a light yellow solution. After removal of the solvent, the [Pt(IV)Cl$_2$(OAc)(OH)(4,4'-bis(RO)-2,2'-bipyridine)] complexes were reacted with acetic anhydride to form the desired [Pt(IV)Cl$_2$(OAc)$_2$(4,4'-bis(RO)-2,2'-bipyridine)] complexes. This step in the reaction was visually monitored by the appearance of a pale yellow suspension. Seven complexes were successfully synthesized, and their chemical structures are shown in FIG. 5A.

Figure 6A:
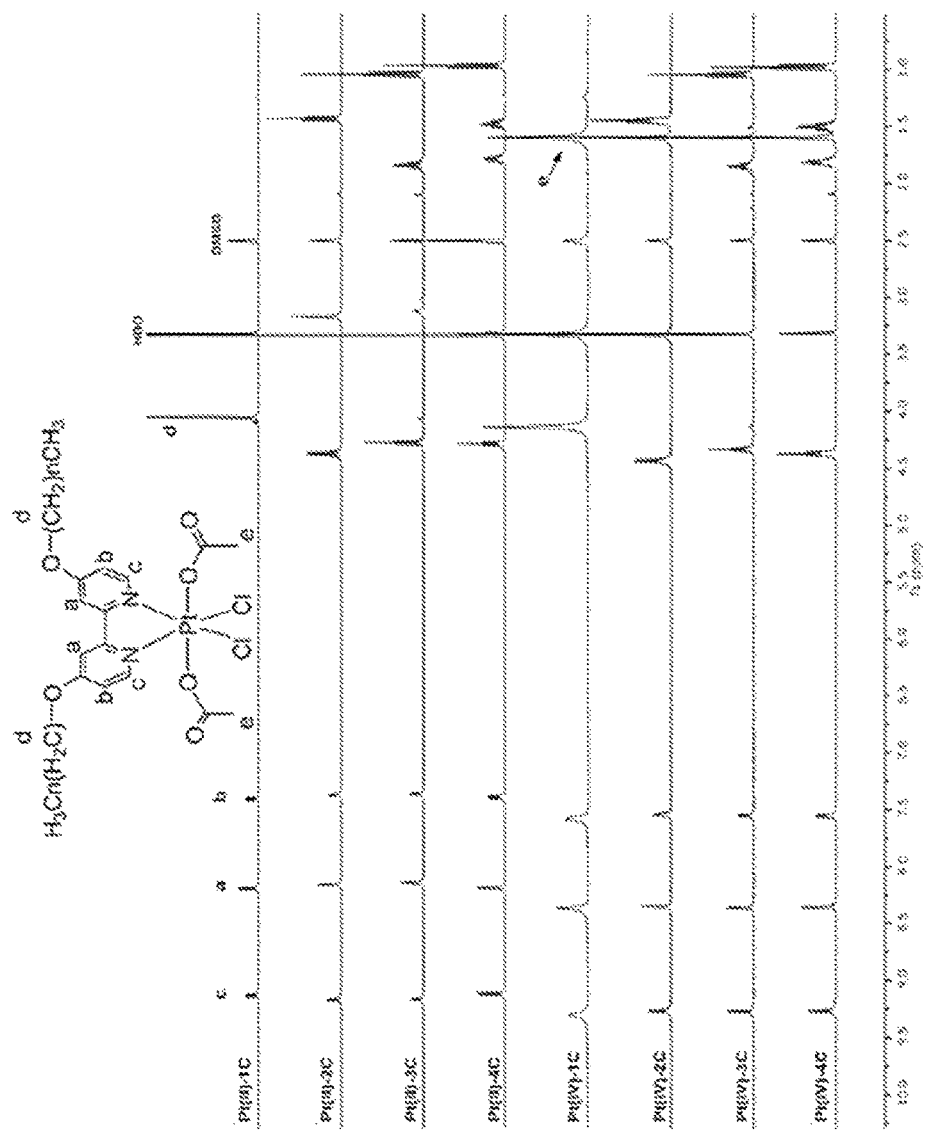
FIG. 6A and FIG. 6B show $^1$H NMR spectra of Pt(II) and Pt(IV) complexes recorded in DMSO-d$_6$ (FIG. 6A) or CDCl$_3$ (FIG. 6B) at room temperature.
Figure 6B:
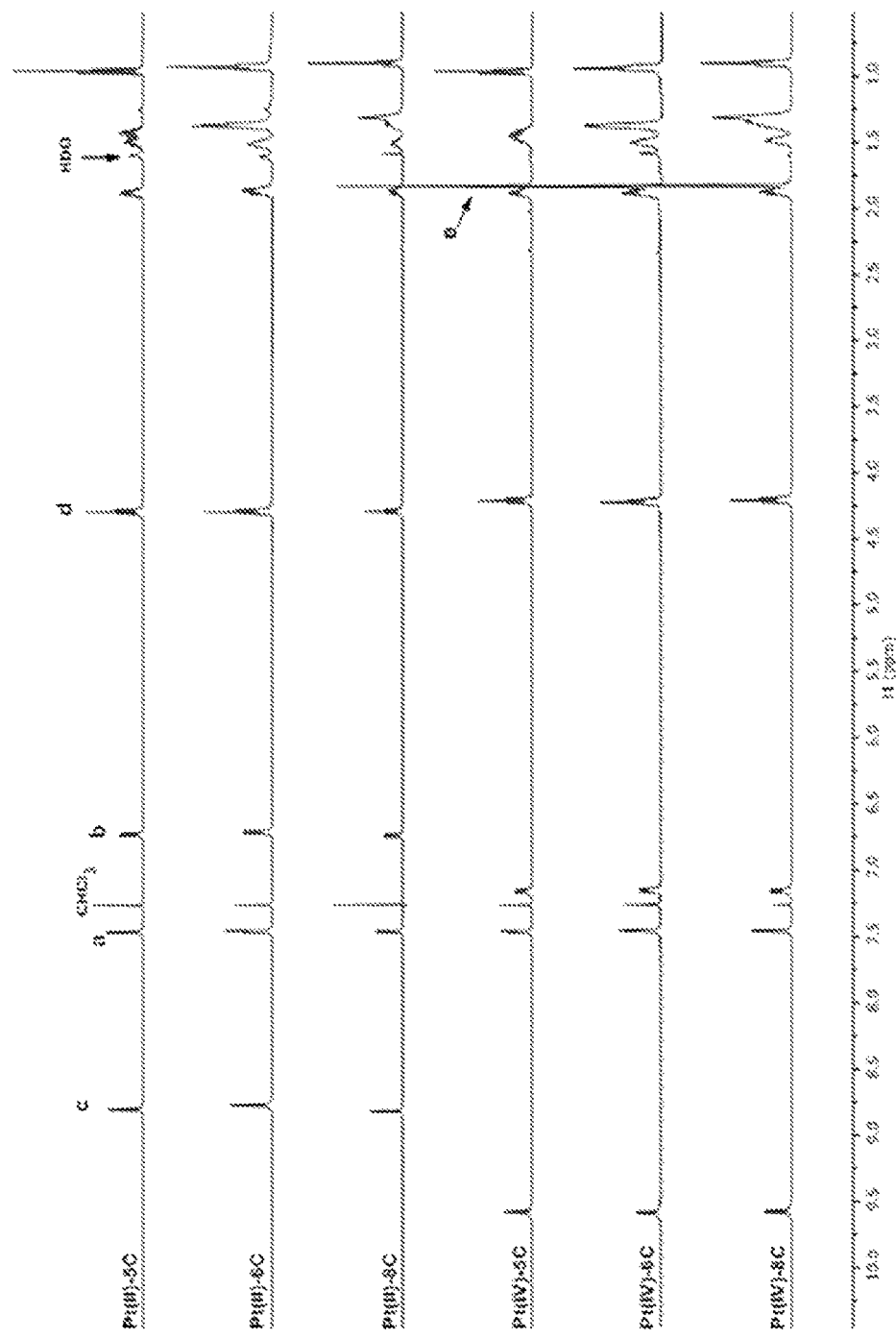

All of the compounds were characterized by $^1$H and $^{13}$C NMR spectroscopy, elemental analysis, and DSC measurements. Elemental analyses of the complexes were in excellent agreement (within 0.5%) with the expected values, thus validating the molecular formulae of these compounds. To compare the NMR chemical shifts of the Pt(IV) complexes to those of the Pt(II) complexes, the Pt(IV) samples were prepared in the same deuterated solvent as the corresponding Pt(II) precursors. The $^1$H and $^{13}$C NMR spectra of Pt(IV)-1C—Pt(IV)-4C were recorded in DMSO-$d_6$, whereas those of Pt(IV)-5C—Pt(IV)-8C were recorded in CDCl$_3$. The spectra of all of the complexes displayed the expected proton and carbon resonances; the $^1$H NMR chemical shifts of the Pt(II) and Pt(IV) complexes are depicted in FIGS. 6A and 6B. The appearance of a singlet peak between 1.6-1.8 ppm in the $^1$H spectra (peak e) and two additional peaks in the $^{13}$C spectra indicate the presence of the diacetato ligands attached to the Pt center. While the chemical shifts of the protons in the alkyl region remained relatively the same between the Pt(II) and Pt(IV) complexes, the chemical shifts of the aromatic protons (peaks a-c) and the methylene protons next to the oxygen attached to the bipyridine ring (peak d) are slightly shifted. All of the aromatic proton peaks (FIG. 6A, peaks a-c) and the methylene protons peak (FIG. 6A, peak d) of the Pt(IV) complexes in DMSO-$d_6$ are shifted downfield compared to Pt(II); however, the methylene proton signal (FIG. 6B, peak d) of the Pt(IV) complexes recorded in CDCl$_3$ is slightly shifted upfield and only the peaks corresponding to the protons at the 6,6' (peak c) and 5,5' (peak b) positions are shifted downfield. Similar to the proton signals, carbon signals of the Pt(IV) complexes are shifted to varying degrees compared to Pt(II) complexes.

Figure 7:
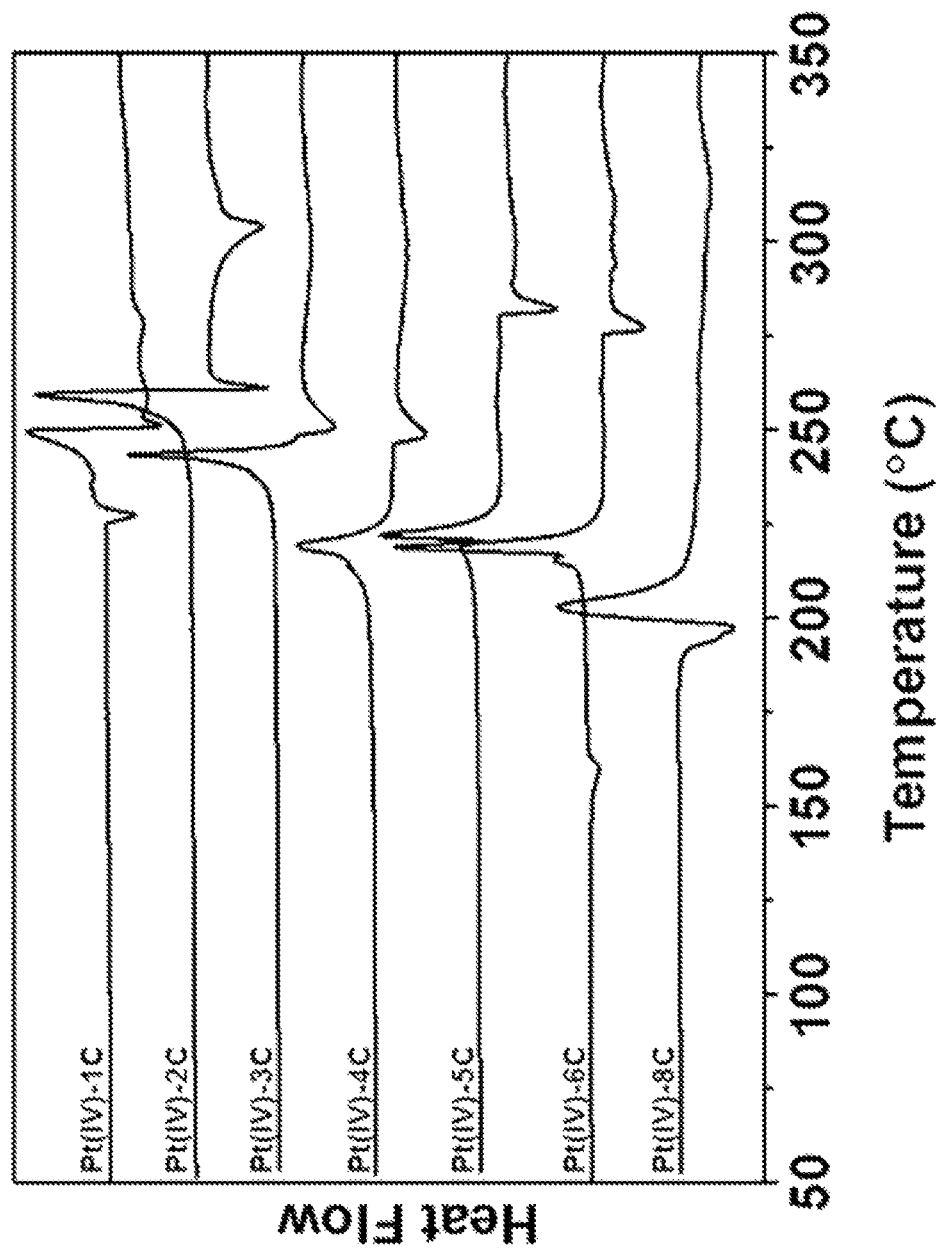
FIG. 7 is a graph plotting DSC thermograms of [Pt(IV)Cl$_2$(OAc)$_2$(4,4'-bis(RO)-2,2'-bipyridine)] complexes obtained in the first heating cycles in nitrogen at a heating rate of 10° C./minute.

The thermal characteristics of the synthesized Pt(IV) compounds were studied using DSC analysis. As depicted in the DSC thermogram (FIG. 7), the thermal transitions of all the synthesized Pt(IV) complexes had a similar trend, but there were slight variations. Although all of the complexes had an exothermic peak indicating decomposition, the $T_{onset}$-$T_{max}$ ranges for the decomposition temperatures of Pt(IV)-1C—Pt(IV)-4C were lower than the melting ranges of the Pt(II) counterparts, and the ranges for Pt(IV)-5C—Pt(IV)-8C were higher than the melting ranges of the Pt(II) (Table 1). All of the Pt(IV) complexes also had an endotherm at varying temperatures after decomposition. Additionally, the DSC thermogram of Pt(IV)-1C displayed an endotherm about 10° C. before the $T_{onset}$ of decomposition, and Pt(IV)-5C and Pt(IV)-8C each had an endotherm immediately before $T_{onset}$ of decomposition. Pt(IV)-6C also had a broad low energy endotherm between 150-160° C. The endotherms occurring before the decomposition temperature may be due to crystal-to-crystal transitions. Since the compounds decompose, only one heating cycle was done instead of performing both heating and cooling cycles.

with concentrations of 10 mM or higher were obtainable, whereas the Pt(II) can only be made at the highest concentration of 5 mM. The solubility of Pt(IV)-8C was markedly improved compared to Pt(II)-8C, which was not evaluated for anti-proliferative activities due to poor solubility in DMSO and other common organic solvents that could be used for in vitro testing.

2. In Vitro Cytotoxic Activity

Figure 8A:
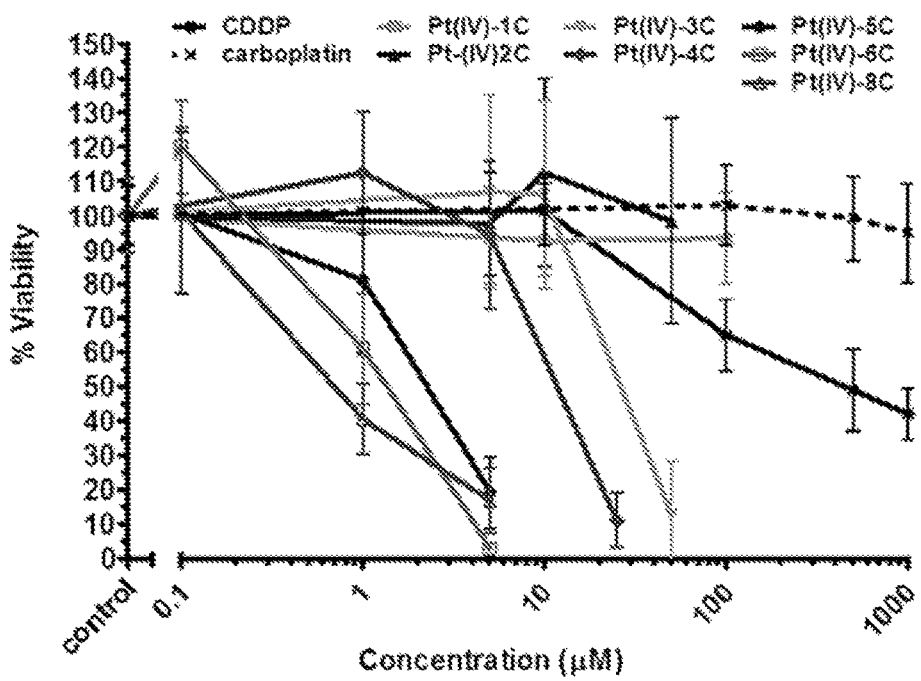
FIG. 8A-8F are graphs plotting the percent viability of DU145 (FIG. 8A), PC-3 (FIG. 8B), SK-BR-3 (FIG. 8C), ZR-75-1 (FIG. 8D), A549 (FIG. 8E), and MCF-7 (FIG. 8F) cells after treatment for 1 hour (top panel of each figure) or 48 hours (bottom panel of each figure) with the indicated Pt(IV) complexes.
Figure 8B:
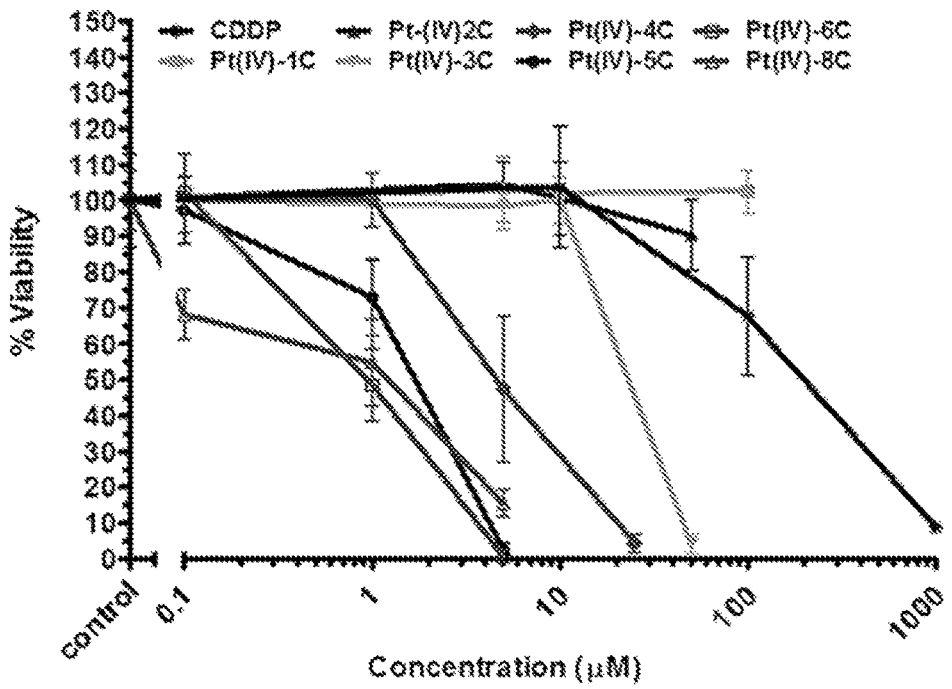
Figure 8B:
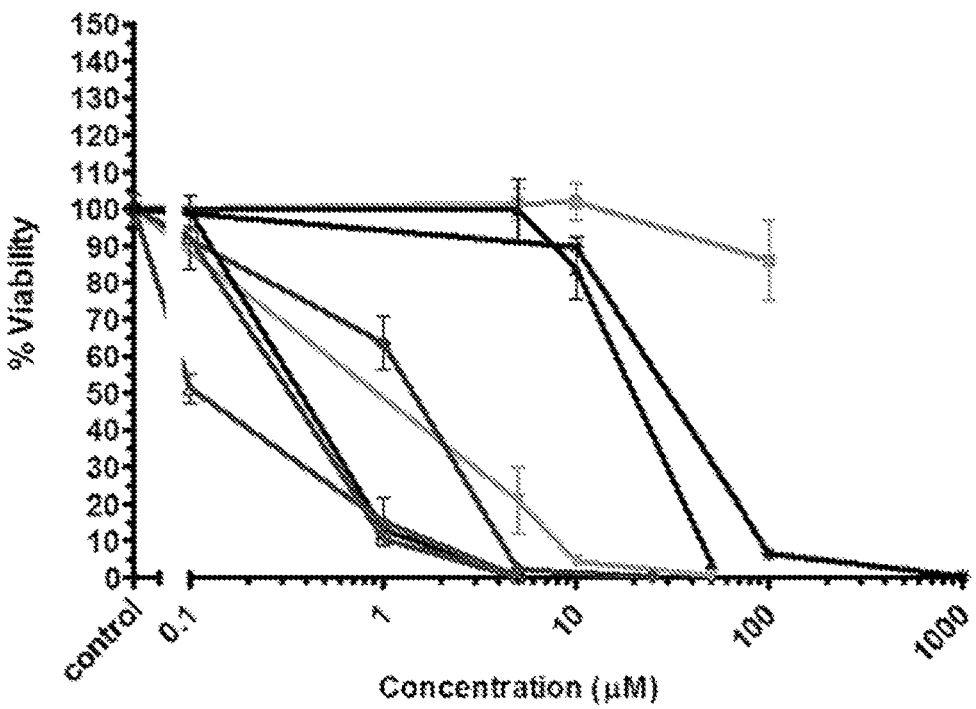
Figure 8C:
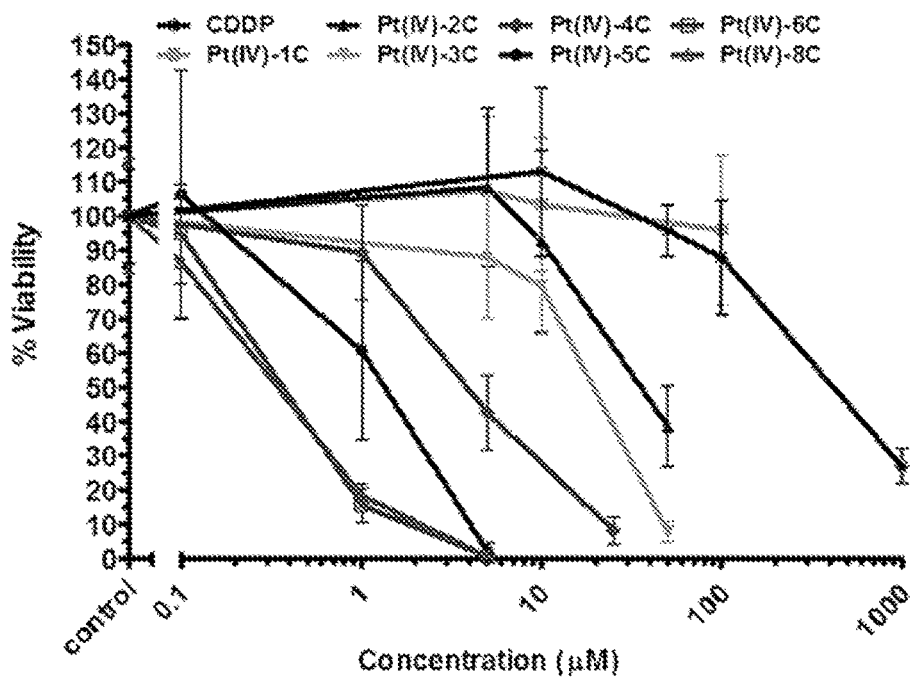
Figure 8C:
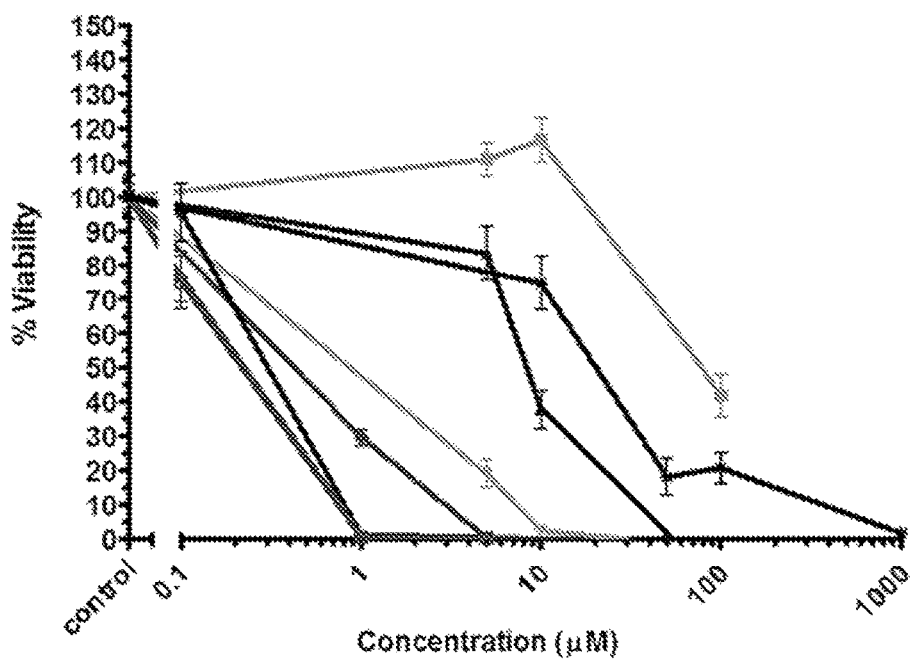
Figure 8D:
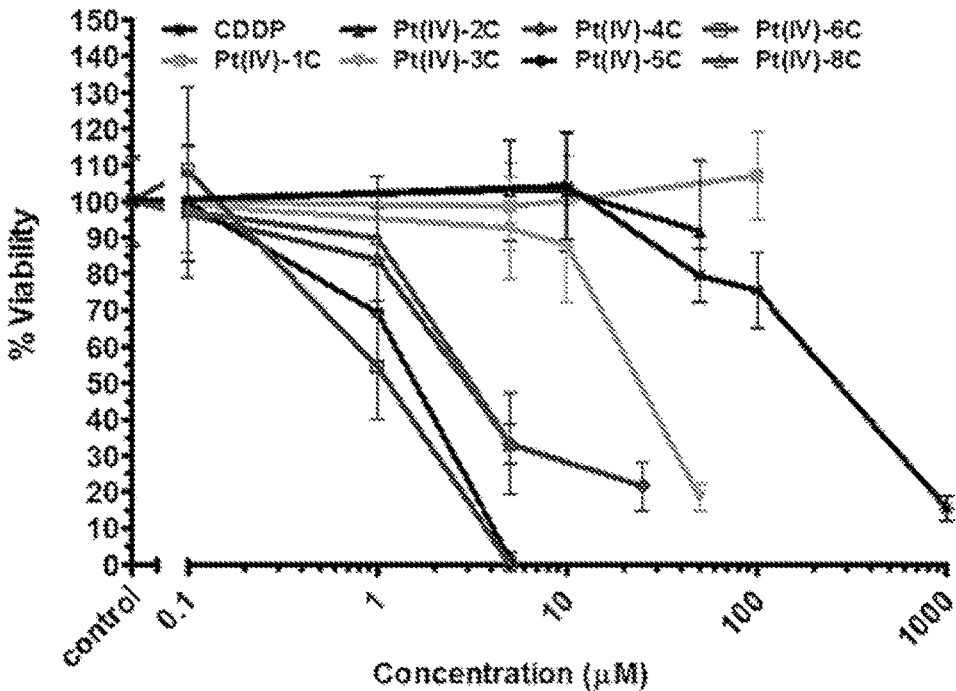
Figure 8D:
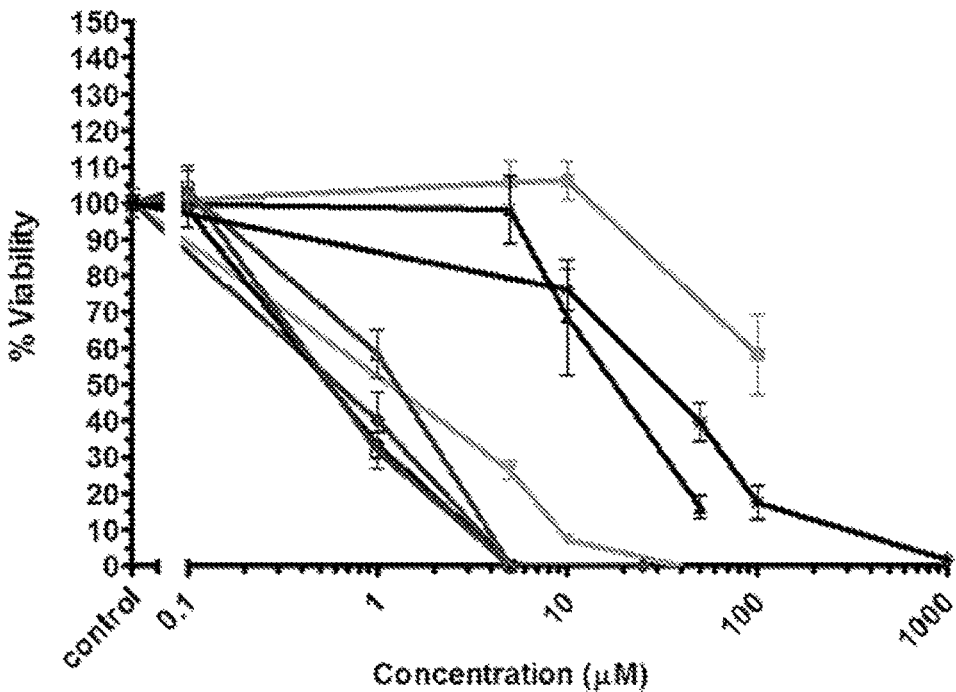
Figure 8E:
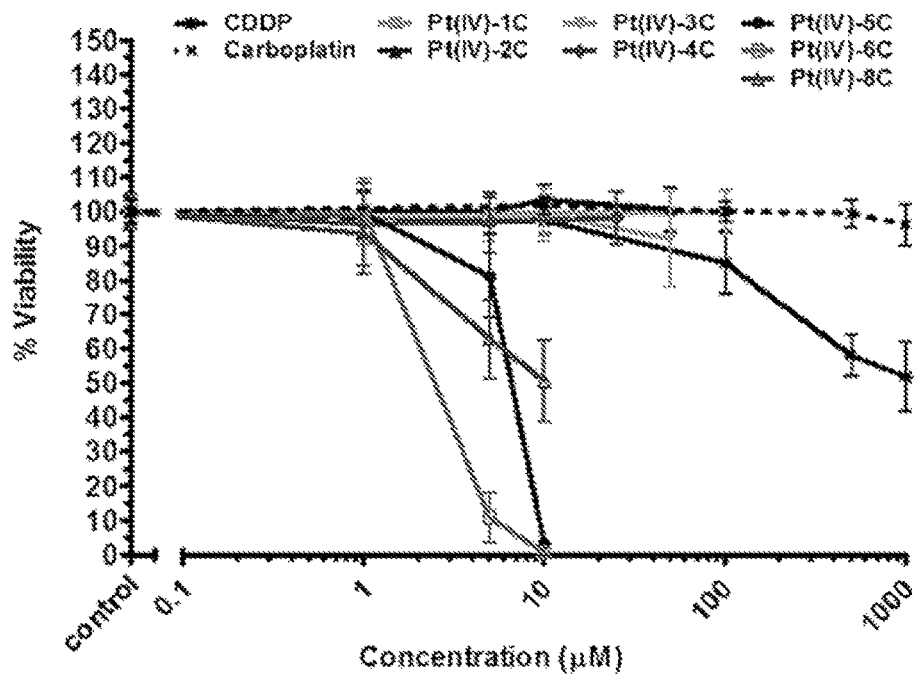
Figure 8E:
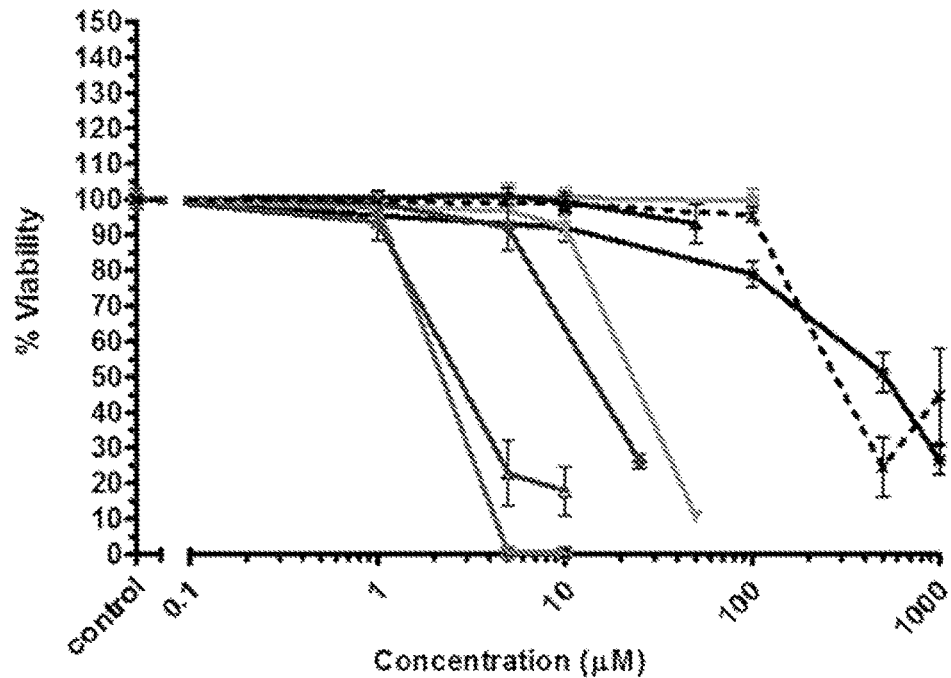
Figure 8F:
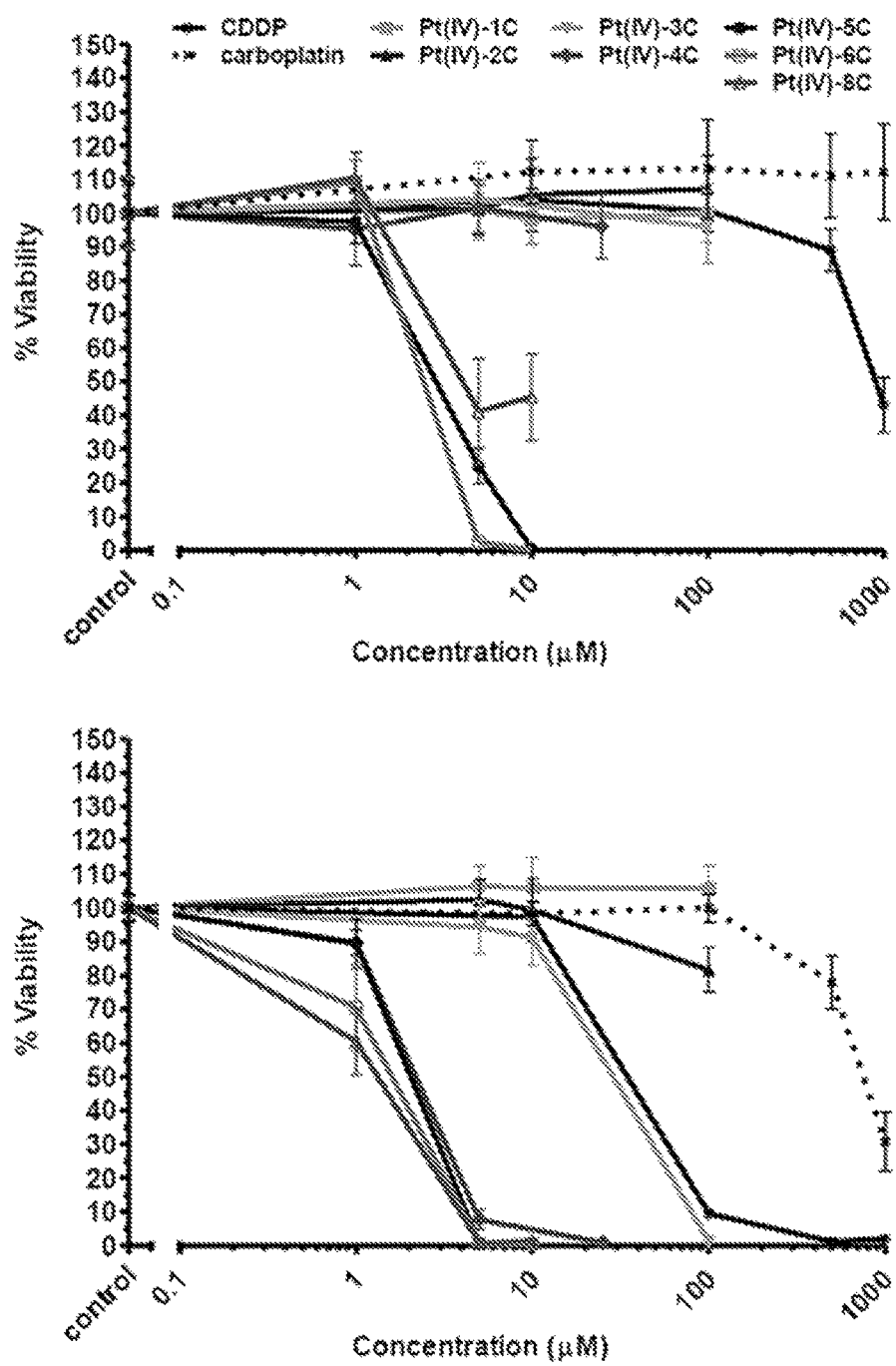

The anti-proliferative activities of Pt(IV) complexes were determined in two lung (A549 and H520), two prostate (DU145 and PC-3), and six breast (HCC38, MCF-7, MDA-MB-231, SK-BR-3, T-47D, and ZR-75-1) cancer cell lines. The cells were treated with increasing concentrations of cisplatin (CDDP), carboplatin, or the Pt(IV) complexes for 1 or 48 hours, and the viability was measured using an MTS colorimetric cell proliferation assay. Graphs of the results are shown for DU145 (FIG. 8A), PC-3 (FIG. 8B), SK-BR-3 (FIG. 8C), ZR-75-1 (FIG. 8D), A549 (FIG. 8E), and MCF-7 (FIG. 8F).

Figure 8G:
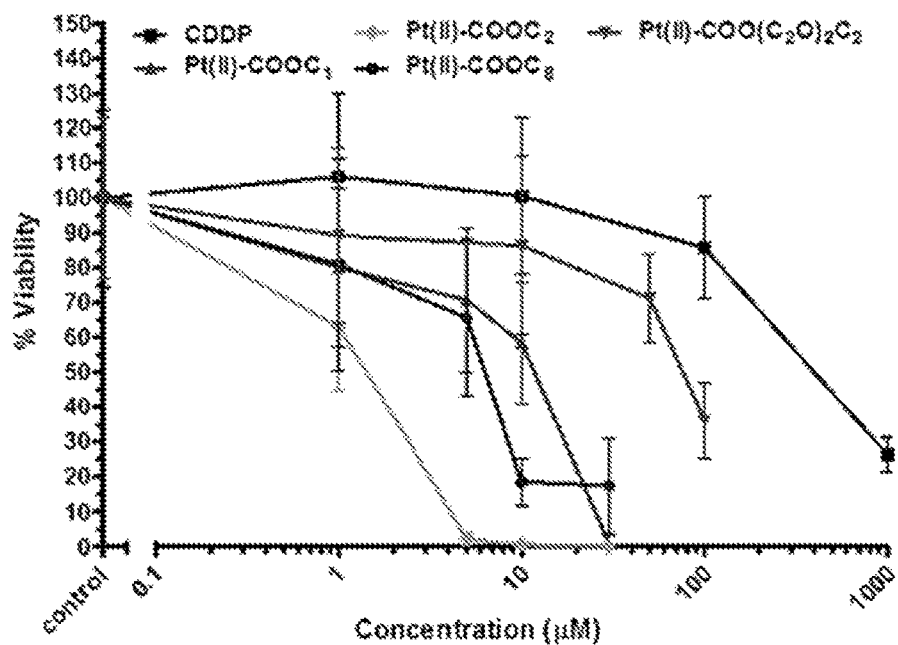
FIG. 8G-8I are graphs plotting the percent viability of SK-BR-3 (FIG. 8G), DU145 (FIG. 8H), and PC-3 (FIG. 8I) cells after treatment for 1 hour (top panel of each figure) or 48 hours (bottom panel of each figure) with the indicated Pt(II) complexes.
Figure 8G:
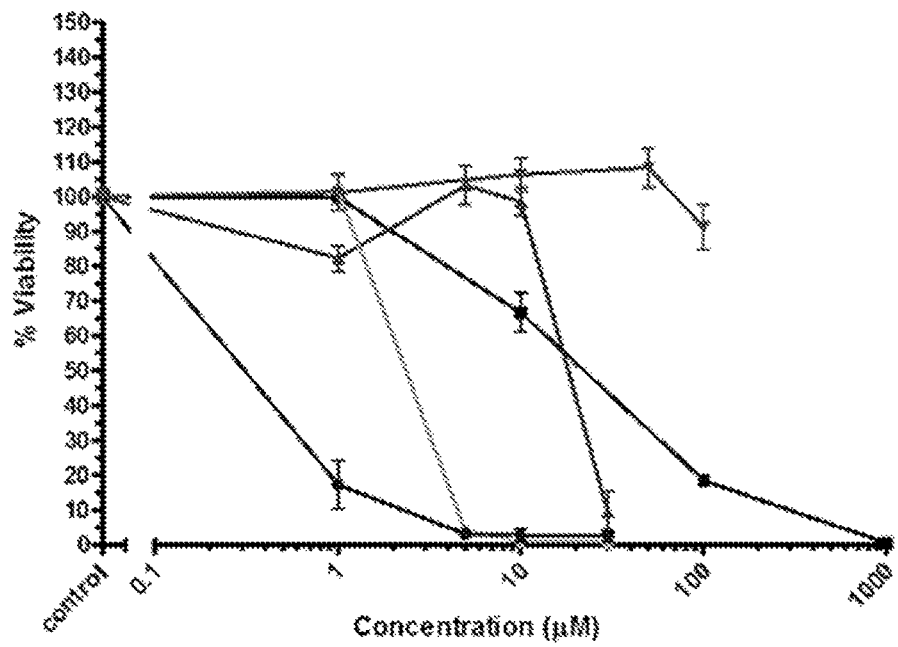
Figure 8H:
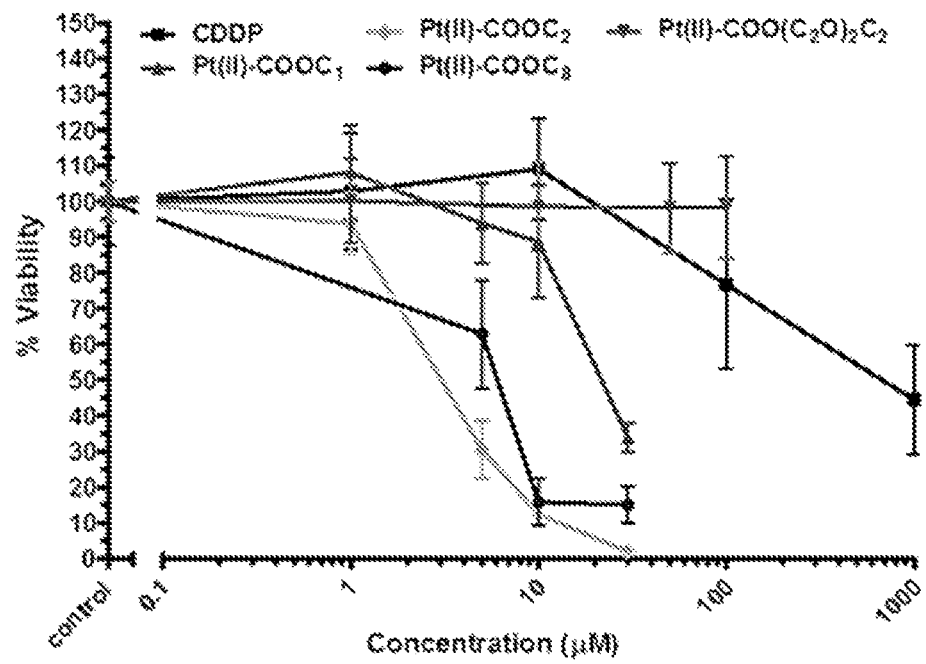
Figure 8H:
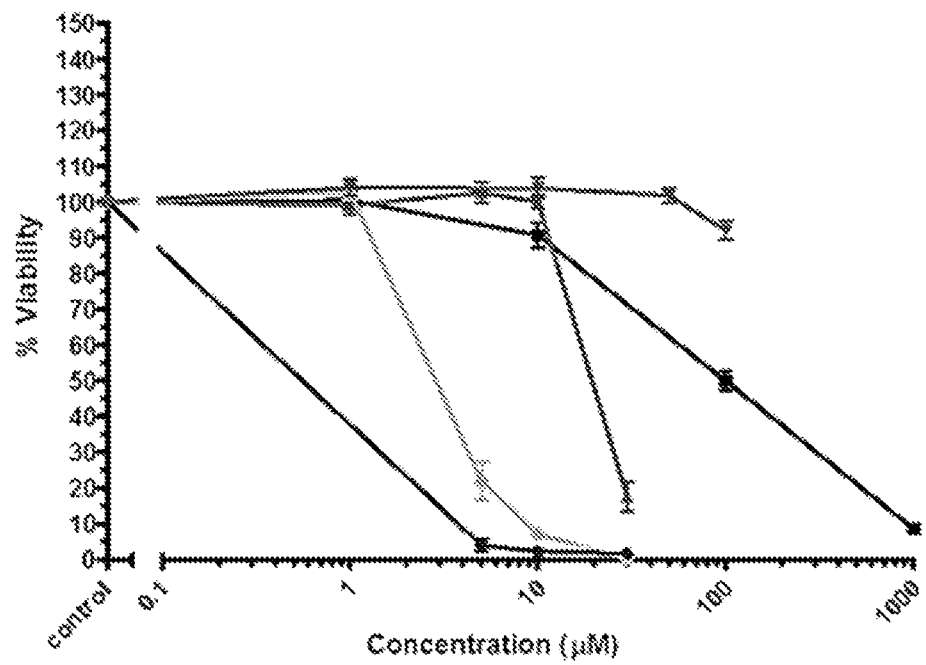
Figure 8I:
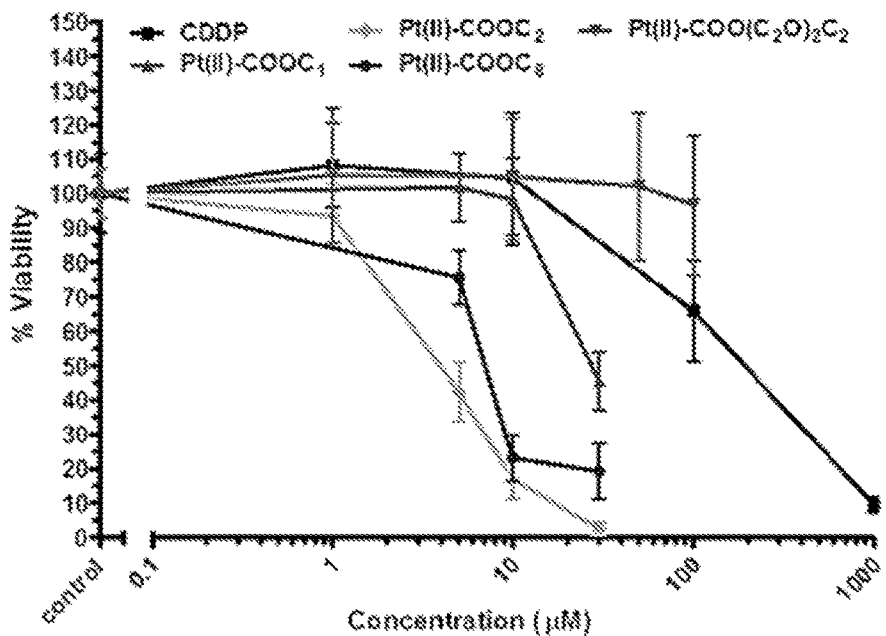
Figure 8I:
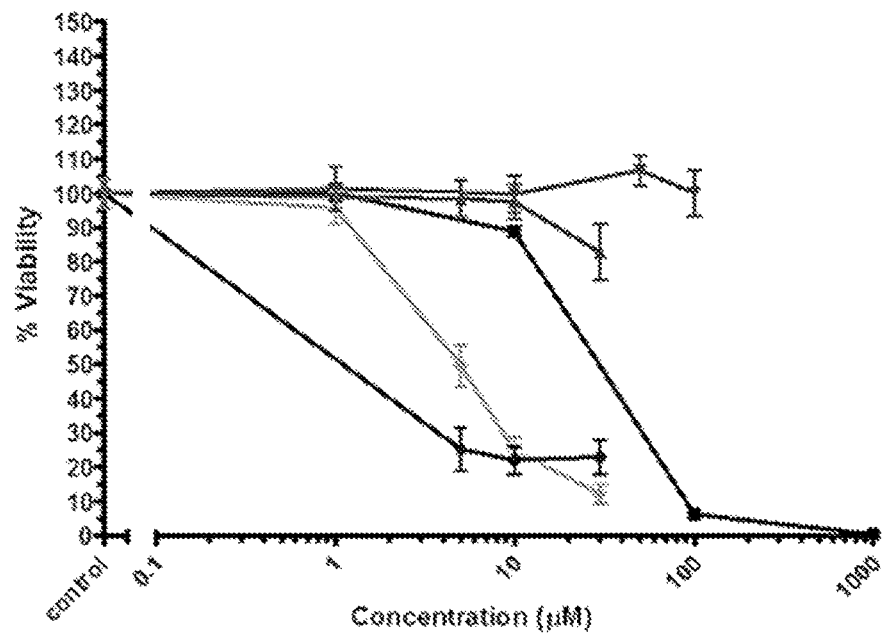

The anti-proliferative activities of certain Pt(II) complexes were determined in DU145, PC-3, and SK-BR-3 cells. The cells were treated with increasing concentrations of cisplatin (CDDP) or the Pt(II) complexes for 1 or 48 hours, and the viability was measured using an MTS colorimetric cell proliferation assay. Graphs of the results are shown in FIGS. 8H-8I.

For the 1 hour treatment of DU145 cells (FIG. 8A, top), cisplatin caused a concentration dependent decrease in cell viability (a 60% reduction by the highest concentration of 1 mM), while carboplatin had no effect even up to 1 mM. The two complexes with short alkoxy substituents, Pt(IV)-1C (one carbon) and Pt(IV)-2C (two carbons), also did not have any effects at the concentrations tested (up to 100 µM for Pt(IV)-1C and 50 µM for Pt(IV)-2C). Complexes Pt(IV)-3C to Pt(IV)-8C all caused a concentration dependent decrease in DU145 cell viability and were more effective than cisplatin. Pt(IV)-3C was the least effective among the five active compounds, followed by Pt(IV)-4C, with Pt(IV)-5C to Pt(IV)-8C having similar activities. When the treatment time was extended to 48 hours (FIG. 8A, bottom), the activities of all the platinum compounds were increased. However, all of the Pt(IV) complexes were still more effective than cisplatin except for Pt(IV)-1C, which was more effective than carboplatin.

Similar trends were observed for A549 (FIG. 8E) and MCF-7 (FIG. 8F) cells, except these cells were not as sensitive to treatment with the platinum complexes as DU145 cells. In addition, Pt(IV)-3C and Pt(IV)-4C did not have any effect on A549 and MCF-7 cells at the concentrations tested for the 1 hour treatment, and Pt(IV)-1C and Pt(IV)-2C had no effect for the 48 hour treatment. The dramatically increased activities of Pt(IV)-3C and Pt(IV)-4C

TABLE 1

| Complex | Pt-1C | Pt-2C | Pt-3C | Pt-4C | Pt-5C | Pt-6C | Pt-8C |
| --- | --- | --- | --- | --- | --- | --- | --- |
| Pt(II) | 311-316 | 318-322 | 269-272 | 229-230 | 173-175 | 176-179 | 169-172 |
| Pt(IV) | 239-249 | 256-259 | 242-243 | 215-219 | 220-222 | 217-219 | 197-203 |

$T_{onset}$-$T_{max}$ (° C.) of the Pt(II) melting temperatures vs. the Pt(IV) decomposition temperatures are shown.

Coordination of the axial ligands to the Pt center improved the solubility of the complexes in common organic solvents. DMSO solutions of the Pt(IV) complexes for the 48 hour treatment compared to the 1 hour treatment is an indication that the anti-proliferative activities of the platinum complexes are not due to a surfactant effect, since interactions of the hydrophobic alkyl chain with the cell membrane would result in a faster response.

The anti-proliferative activities of a few Pt(II) complexes containing diester substituted 2,2'-bipyridine were tested in SK-BR-3 (FIG. 8G) human breast cancer cells, and also in DU145 (FIG. 8H) and PC-3 (FIG. 8I) human prostate cancer cells. Cisplatin caused a concentration dependent decreased in cell viability of the three cell lines tested for both the one and 48 hours treatment, with the 48 hour treatment having a greater effect. Pt(II) complexes containing diester substituted 2,2'-bipyridine also caused a concentration dependent decrease in the cell viability of SK-BR-3, DU145, and PC-3 cells. Pt(II)-COOC$_1$, Pt(II)-COOC$_2$, and Pt(II)-COOC$_8$ were generally more effective than cisplatin, while Pt(II)-COO(C$_2$O)$_2$C$_2$ was not as effective as cisplatin. Interestingly, SK-BR-3 cells treated for one hour with the Pt(II)-COO(C$_2$O)$_2$C$_2$ complex (FIG. 8G, top panel) had a greater reduction in cell viability than when they were treated for 48 hours (FIG. 8G, bottom panel). Similar results were observed for the Pt(II)-COOC$_1$ complex in PC-3 cells. These differences may be due to the washing step during the one hour treatment. Since the Pt(II)-COOC$_1$ and Pt(II)-COOC$_2$ complexes with short chain ester substituents, and the Pt(II)-COOC$_8$ complex with long chain ester substituents all showed anti-proliferative activities, it is likely that the intermediate complexes also have anti-proliferative activities.

It should be noted that while the solubility of the Pt(IV) complexes in organic solvents were increased compared to their Pt(II) precursors, they were still poorly soluble in water. Thus, Pt(IV)-1C to Pt(IV)-3C were limited to a highest concentration of 100 µM. Interestingly, Pt(IV)-4C precipitated out of solution at concentrations of 30 µM or higher when the stock DMSO solution was diluted in the culture medium. Testing of Pt(IV)4C therefore was limited to 25 µM. Pt(IV)-8C gave similar results regardless of whether the stock solution was made in DMSO or ethanol, suggesting that the chloride leaving groups were not displaced by DMSO and that the Pt(IV)-8C structure is stable.

The effective concentration of the Pt(IV) complexes that resulted in 50% cell viability (EC$_{50}$) for all the cell lines tested are given in Tables 2-5. Comparison of the EC$_{50}$ values indicated that the Pt(IV) complexes were generally more effective than cisplatin. A549 and MCF-7 were the most resistant cell lines, while SK-BR-3 and T-47D were the most sensitive. Similar to Pt(II) complexes, the activity of the Pt(IV) complexes increased as the carbon number on the alkoxy substituent was increased. Pt(IV) complexes with short chains of one to three carbons were not as effective as their Pt(II) precursors, while Pt(IV) complexes with longer chains of five to eight carbons were more effective than their Pt(II) precursors. Pt(II)-4C and Pt(IV)-4C (with four carbon chains) had similar activities.

TABLE 2

| | Lung cancer | | Prostate cancer | | Breast cancer | | | | | |
|---|---|---|---|---|---|---|---|---|---|---|
| 1 h treatment | A549 | H520 | DU145 | PC-3 | HCC38 | MCF-7 | MDA-MB-231 | SK-BR-3 | T-47D | ZR-75-1 |
| CDDP | 900 ± 200 | 200 ± 17 | 400 ± 100 | 200 ± 20 | 300 ± 30 | 900 ± 60 | 50 ± 4 | 420 ± 80 | 900 ± 100 | 260 ± 10 |
| Carboplatin | >1000 | ND | >1000 | ND | ND | >1000 | ND | ND | ND | ND |
| Pt(II)-1C | >100 | >100 | 40 ± 10$^a$ | >100 | 80 ± 20$^a$ | >100 | >100 | 19 ± 5$^a$ | 20 ± 1$^a$ | 67 ± 27$^a$ |
| Pt(II)-2C | >100 | >100 | 20 ± 5$^a$ | 22 ± 5$^a$ | 18 ± 4$^a$ | >100 | 30 ± 20 | 2.2 ± 0.2$^a$ | 5 ± 2$^a$ | 58 ± 15$^a$ |
| Pt(II)-3C | 48 ± 3$^a$ | 40 ± 20$^a$ | 6 ± 1$^a$ | 5 ± 1$^a$ | 3 ± 2$^a$ | 100 ± 0$^a$ | 4 ± 2$^a$ | 1.81 ± 0.03$^a$ | 2.4 ± 0.1$^a$ | 8.9 ± 0.4$^a$ |
| Pt(II)-4C | 17 ± 1$^a$ | 20 ± 1$^a$ | 12 ± 8$^a$ | 11 ± 2$^a$ | 12 ± 6$^a$ | 22 ± 2$^a$ | 4 ± 3$^a$ | 5 ± 4$^a$ | 12 ± 7$^a$ | 21 ± 2$^a$ |
| Pt(II)-5C | 18 ± 1$^a$ | 23 ± 5$^a$ | 8 ± 2$^a$ | 7 ± 1$^a$ | 13 ± 5$^a$ | 21 ± 5$^a$ | 4 ± 2$^a$ | 2.8 ± 0.8$^a$ | 9 ± 3$^a$ | 8 ± 3$^a$ |
| Pt(II)-6C | 66 ± 16$^a$ | >50 | 2.1 ± 0.1$^a$ | 2.24 ± 0.03$^a$ | 16 ± 5$^a$ | 80 ± 30$^a$ | 6 ± 3$^a$ | 1.84 ± 0.03$^a$ | 3.2 ± 0.8$^a$ | 7 ± 2$^a$ |
| Pt(II)-8C | ND | ND | ND | ND | ND | ND | ND | ND | ND | ND |

Data represent mean ± SD from at least two independent experiments done in quadruplicates.
$^a$P < 0.5 compared to CDDP.
$^b$ P < 0.05 compared to carboplatin.

TABLE 3

| | Lung cancer | | Prostate cancer | | Breast cancer | |
|---|---|---|---|---|---|---|
| 1 h treatment | A549 | H520 | DU145 | PC-3 | HCC38 | MCF-7 |
| CDDP | 900 ± 200 | 200 ± 17 | 400 ± 100 | 200 ± 20 | 300 ± 30 | 900 ± 100 |
| Carboplatin | >1000 | ND | >1000 | ND | ND | >1000 |
| Pt(IV)-1C | >100 | >100 | >100 | >100 | >100 | >100 |
| Pt(IV)-2C | >50 | >100 | >50 | >50 | 93 ± 10$^a$ | >100 |
| Pt(IV)-3C | >50 | 80 ± 20$^a$ | 24 ± 7$^a$ | 23.0 ± 0.3$^a$ | 26 ± 6$^a$ | >100 |
| Pt(IV)-4C | >25 | 13 ± 5$^a$ | 8 ± 7$^a$ | 5 ± 3$^a$ | 17 ± 3$^a$ | >25 |
| Pt(IV)-5C | 6.6 ± 0.3$^a$ | 3 ± 1$^a$ | 1 ± 1$^a$ | 1.7 ± 0.2$^a$ | 3 ± 1$^a$ | 2.9 ± 0.13$^a$ |
| Pt(IV)-6C | 2.5 ± 0.2$^a$ | 2.1 ± 0.2$^a$ | 1.3 ± 0.2$^a$ | 2.0 ± 0.3$^a$ | 2.3 ± 0.2$^a$ | 2.4 ± 0.1$^a$ |
| Pt(IV)-8C | 7.0 ± 0.4$^a$ | 7 ± 5$^a$ | 0.7 ± 0.3$^a$ | 1.2 ± 0.5$^a$ | 3.0 ± 0.6$^a$ | 4 ± 1$^a$ |

| | Breast cancer | | | |
|---|---|---|---|---|
| 1 h treatment | MDA-MB-231 | SK-BR-3 | T-47D | ZR-75-1 |
| CDDP | 50 ± 4 | 420 ± 80 | 900 ± 100 | 260 ± 10 |
| Carboplatin | ND | ND | ND | ND |
| Pt(IV)-1C | >100 | >100 | >100 | >100 |
| Pt(IV)-2C | >100 | 40 ± 10$^a$ | 46 ± 8$^a$ | >50 |
| Pt(IV)-3C | 34 ± 7$^a$ | 19 ± 2$^a$ | 24 ± 3$^a$ | 24 ± 3$^a$ |
| Pt(IV)-4C | 2.8 ± 0.1$^a$ | 4.0 ± 0.7$^a$ | 10 ± 1$^a$ | 2.9 ± 0.3$^a$ |

TABLE 3-continued

| | | | | |
|---|---|---|---|---|
| Pt(IV)-5C | 1.8 ± 0.1[a] | 1.3 ± 0.6[a] | 2.3 ± 0.3[a] | 1.6 ± 0.1[a] |
| Pt(IV)-6C | 1.1 ± 0.2[a] | 0.36 ± 0.02[a] | 2.1 ± 0.4[a] | 1.1 ± 0.4[a] |
| Pt(IV)-8C | 2.1 ± 0.2[a] | 0.33 ± 0.05[a] | 1.5 ± 0.5[a] | 3.0 ± 1[a] |

Data represent mean ± SD from at least two independent experiments done in quadruplicates.
[a]$P < 0.5$ compared to CDDP.
[b]$P < 0.05$ compared to carboplatin.

TABLE 4

| | Lung cancer | | Prostate cancer | | Breast cancer | |
|---|---|---|---|---|---|---|
| 48 h treatment | A549 | H520 | DU145 | PC-3 | HCC38 | MCF-7 |
| CDDP | 500 ± 100 | 24 ± 2 | 64 ± 8 | 30 ± 1 | 30 ± 8 | 35 ± 1 |
| Carboplatin | 300 ± 30 | ND | 400 ± 100[a] | ND | ND | 800 ± 100[a] |
| Pt(II)-1C | >100 | 30 ± 2 | 24 ± 2[a,b] | 40 ± 7 | 57 ± 2[a] | >100 |
| Pt(II)-2C | 66 ± 7[a,b] | 21 ± 1 | 11 ± 4[a,b] | 21 ± 7 | 20 ± 3 | >100 |
| Pt(II)-3C | 17 ± 1[a,b] | 13 ± 5[a] | 4 ± 2[a,b] | 5.1 ± 0.8[a] | 4.7 ± 0.5[a] | 19 ± 4[a,b] |
| Pt(II)-4C | 15.4 ± 0.5[a,b] | 14 ± 6 | 5 ± 2[a,b] | 7.4 ± 0.5[a] | 7.3 ± 3 | 13 ± 1[a,b] |
| Pt(II)-5C | 16.5 ± 0.5[a,b] | 17 ± 3 | 6.0 ± 0.7[a,b] | 7.3 ± 0.7[a] | 10 ± 2 | 15 ± 7[a,b] |
| Pt(II)-6C | 19.1 ± 0.8[a,b] | 18 ± 1 | 1.9 ± 0.1[a,b] | 2.7 ± 0.1[a] | 14 ± 4 | 12 ± 4[a,b] |
| Pt(II)-8C | ND | ND | ND | ND | ND | ND |

| | | Breast cancer | | | |
|---|---|---|---|---|---|
| 48 h treatment | | MDA-MB-231 | SK-BR-3 | T-47D | ZR-75-1 |
| CDDP | | 21 ± 3 | 23 ± 6 | 35 ± 6 | 30 ± 8 |
| Carboplatin | | ND | ND | ND | ND |
| Pt(II)-1C | | >100 | 23 ± 2 | 21 ± 1[a] | 26 ± 1 |
| Pt(II)-2C | | 20 ± 6 | 1.8 ± 0[a] | 2.2 ± 0.4[a] | 16.5 ± 0 |
| Pt(II)-3C | | 2.2 ± 0.1[a] | 1.73 ± 0.01[a] | 1.9 ± 0.1[a] | 5 ± 1[a] |
| Pt(II)-4C | | 2.4 ± 0.6[a] | 2.1 ± 0.2[a] | 2.3 ± 0.4[a] | 6.0 ± 0.9[a] |
| Pt(II)-5C | | 4.1 ± 0.2[a] | 2.4 ± 0.4[a] | 3 ± 1[a] | 6.6 ± 0.7[a] |
| Pt(II)-6C | | 4 ± 1[a] | 1.8 ± 0[a] | 2.1 ± 0.2[a] | 6.4 ± 0.4[a] |
| Pt(II)-8C | | ND | ND | ND | ND |

Data represent mean ± SD from at least two independent experiments done in quadruplicates.
[a]$P < 0.5$ compared to CDDP.
[b]$P < 0.05$ compared to carboplatin.

TABLE 5

| | Lung cancer | | Prostate cancer | | Breast cancer | |
|---|---|---|---|---|---|---|
| 48 h | A549 | H520 | DU145 | PC-3 | HCC38 | MCF-7 |
| CDDP | 500 ± 100 | 24 ± 2 | 64 ± 8 | 30 ± 1 | 30 ± 8 | 34 ± 1 |
| Carboplatin | 300 ± 30 | ND | 400 ± 100[a] | ND | ND | 800 ± 100[a] |
| Pt(IV)-1C | >100 | >100 | 80 ± 20[b] | >100 | >100 | >100 |
| Pt(IV)-2C | >50 | 61 ± 2[a] | 10 ± 4[a,b] | 20 ± 2[a] | 30 ± 9 | >100 |
| Pt(IV)-3C | 23 ± 1[a,b] | 8 ± 6[a] | 1 ± 1[a,b] | 1.1 ± 0.4[a] | 8 ± 1[a] | 29 ± 2[a,b] |
| Pt(IV)-4C | 14 ± 1[a,b] | 2.2 ± 0.1[a] | 0.9 ± 0.2[a,b] | 1.1 ± 0.4[a] | 2.1 ± 0.2[a] | 2.2 ± 0.1[a,b] |
| Pt(IV)-5C | 2.2 ± 0.1[a,b] | 1.0 ± 0.3[a] | 0.34 ± 0.02[a,b] | 0.5 ± 0.2[a] | 2.1 ± 0.3[a] | 2.0 ± 0.1[a,b] |
| Pt(IV)-6C | 2.2 ± 0.1[a,b] | 1.0 ± 0.4[a] | 0.5 ± 0.3[a,b] | 0.33 ± 0.04[a] | 1.8 ± 0.5[a] | 1.6 ± 0.2[a,b] |
| Pt(IV)-8C | 3.0 ± 0.5[a,b] | 1.2 ± 0.6[a] | 0.2 ± 0.1[a,b] | 0.11 ± 0.02[a] | 1.6 ± 0.3[a] | 1.3 ± 0.3[a,b] |

| | | Breast cancer | | | |
|---|---|---|---|---|---|
| 48 h | | MDA-MB-231 | SK-BR-3 | T-47D | ZR-75-1 |
| CDDP | | 21 ± 3 | 23 ± 8 | 35 ± 6 | 30 ± 8 |
| Carboplatin | | ND | ND | ND | ND |
| Pt(IV)-1C | | >100 | 80 ± 20[a] | 32.0 ± 0.5 | >100 |
| Pt(IV)-2C | | 28 ± 7 | 8.3 ± 0.7[a] | 0.95 ± 0.03[a] | 17 ± 7 |
| Pt(IV)-3C | | 6.1 ± 0.4[a] | 0.9 ± 0.1[a] | 0.59 ± 0.01[a] | 1.21 ± 0.04[a] |
| Pt(IV)-4C | | 1.0 ± 0.2[a] | 0.44 ± 0.02[a] | 0.33 ± 0.07[a] | 0.7 ± 0.2[a] |
| Pt(IV)-5C | | 0.26 ± 0.01[a] | 0.30 ± 0.03[a] | 0.248 ± 0.001[a] | 0.55 ± 0.07[a] |
| Pt(IV)-6C | | 0.31 ± 0.04[a] | 0.21 ± 0.03[a] | 0.24 ± 0.01[a] | 0.55 ± 0.04[a] |
| Pt(IV)-8C | | 0.9 ± 0.3[a] | 0.22 ± 0.03[a] | 0.25 ± 0[a] | 1.3 ± 0.1[a] |

Data represent the mean ± SD from at least two independent experiments done in quadruplicates.
[a]$P < 0.5$ compared to CDDP.
[b]$P < 0.05$ compared to carboplatin.

3. Detection of DNA Damage

Figure 9:
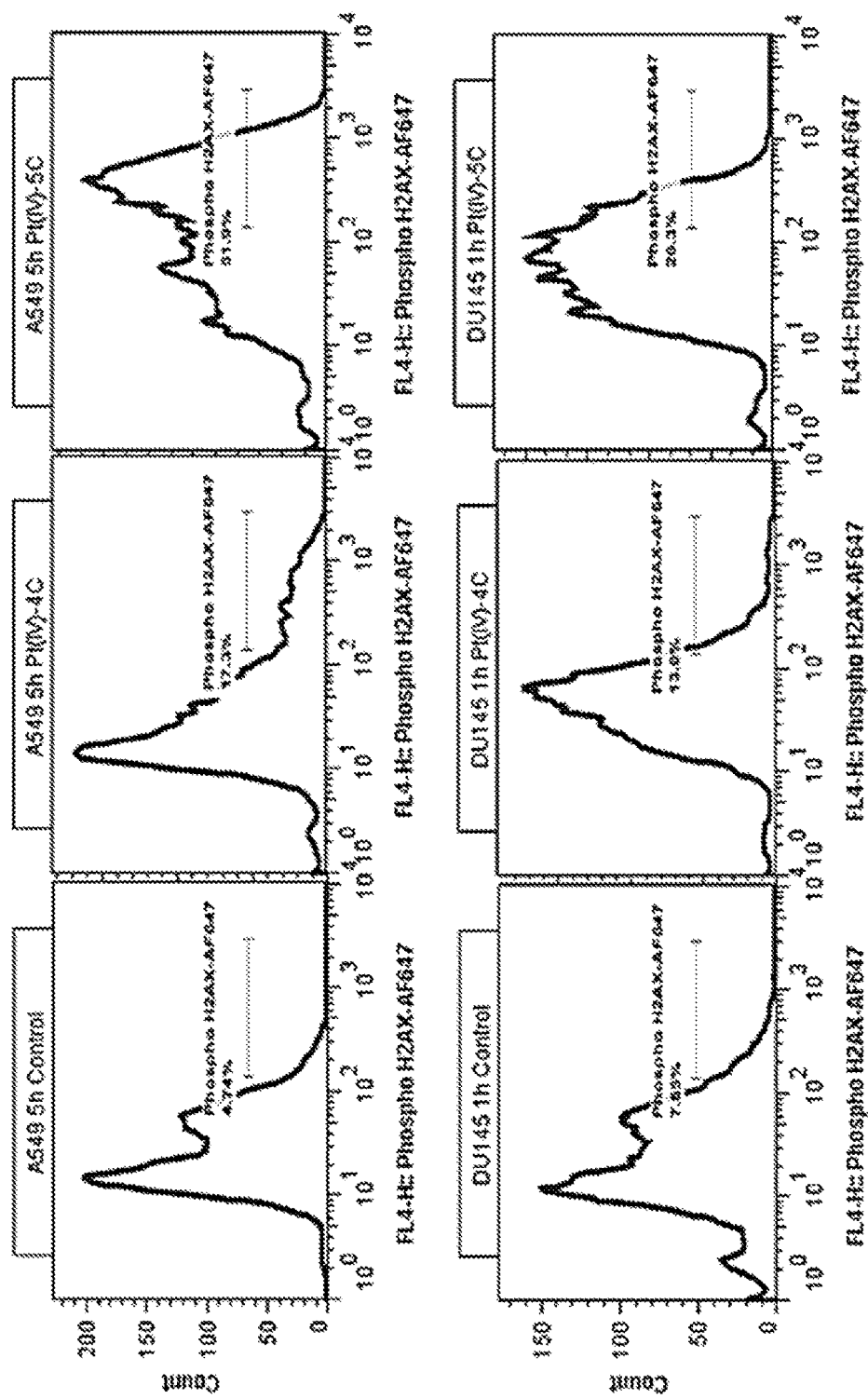
FIG. 9 is a series of graphs plotting Pt(IV) complex-induced phosphorylation of H2AX in A549 cells (top panels) and DU145 cells (bottom panels). A549 cells were treated with control (left), 25 µM Pt(IV)-4C (center), or 7.5 µM Pt(IV)-5C (right) for 6 hours, and analyzed 12 hours post treatment. DU145 cells were treated for 2 hours with control (left), 10 µM Pt(IV)-4C (center), or 2.5 µM Pt(IV)-5C (right), and analyzed 7 hours post treatment. Data are representative of three independent experiments.

Cisplatin binds DNA and forms adducts, which induces cell cycle arrest, DNA damage repair, various stress response pathways, and death pathways. DNA damage by cisplatin has been shown to induce phosphorylation of histone H2AX, which is believed to be involved in recognition and repair of damaged DNA, and regulation of the apoptotic pathway. Flow cytometry was used to analyze levels of phosphorylated H2AX (γH2AX) in A549 and DU145 cells treated with Pt(IV)-4C and Pt(IV)-5C. Representative histograms for each cell line are shown in FIG. 9. As shown, treatment with Pt(IV)-4C and Pt(IV)-5C resulted in an increase of γH2AX in both A549 and DU145 cells. The increase in γH2AX caused by Pt(IV)-4C treatment was not as high as the increase caused by Pt(IV)-5C. Nonetheless, these results indicate that treatment with Pt(IV)-4C and Pt(IV)-5C caused DNA damage in A549 and DU145 cells.

4. Evaluation of Apoptosis

Figure 10:
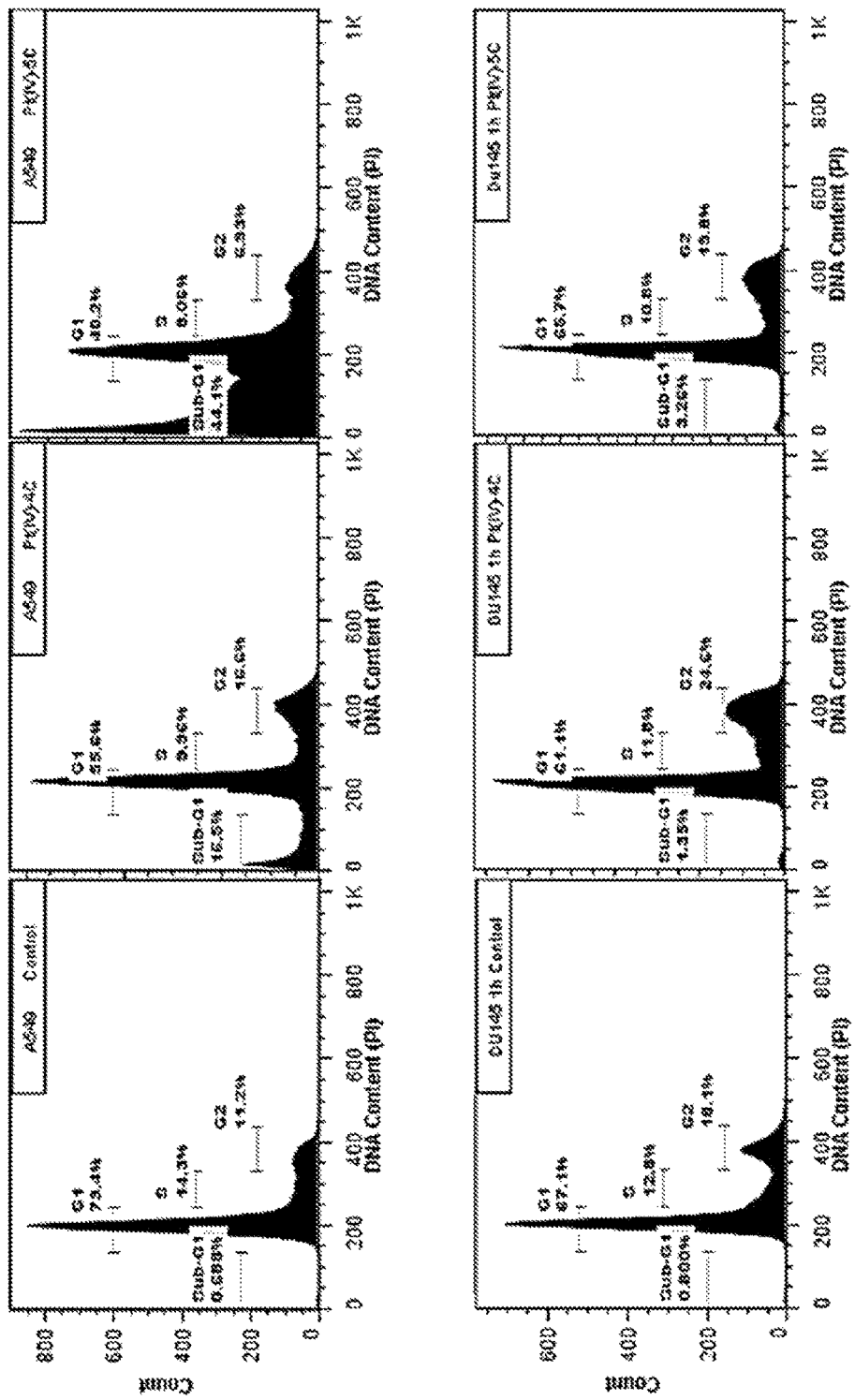
FIG. 10 is a series of plots from a cell cycle analysis of A549 cells (top) and DU145 cells (bottom) cells treated with Pt(IV)-4C and Pt(IV)-5C. A549 cells were treated for 5 hours with control (left), 25 µM Pt(IV)-4C (center), or 7.5 µM Pt(IV)-5C (right), and analyzed 12 hours post treatment. DU145 cells were treated for 1 hour with control (left), 10 µM Pt(IV)-4C (center), or 2.5 µM Pt(IV)-5C (right), and analyzed 12 hours post treatment. Data are representative of three independent experiments.

Cisplatin-induced DNA damage has been associated with cell cycle arrest and induction of apoptosis. Since treatment with Pt(IV)-4C and Pt(IV)-5C caused an increase in γH2AX in A549 and DU145 cells, their effects on the cell cycle was examined. Flow cytometric analysis with propidium iodide provides information on DNA content, which can be correlated with the stages in the cell cycle. Additionally, appearance of a sub-G1 peak is an indication of apoptosis. A549 cells treated with Pt(IV)-4C and Pt(IV)-5C had a decreased percentage of cells in the G1 phase and a corresponding increase in the sub-G1 peak, while the S and G2 phases remained relatively similar to the control (FIG. 10, top). Treatment of DU145 cells with Pt(IV)-4C and Pt(IV)-5C did not affect the cell cycle, and a sub-G1 peak was not detected (FIG. 10, bottom). A sub-G1 peak was not detected even when the treatment time was extended to two and four hours, suggesting that perhaps these treatment durations are not enough to cause fragmentation and leakage of the DNA content to produce a sub-G1 peak. Alternatively, the difference between the response of A549 and DU145 may be due to differences in p53 status, since A549 has wild type p53 and DU145 has mutant p53. It also is possible that lack of apoptotic features in DU145 cells is the result of not having functional p53 to signal the apoptotic pathway.

Figure 11:
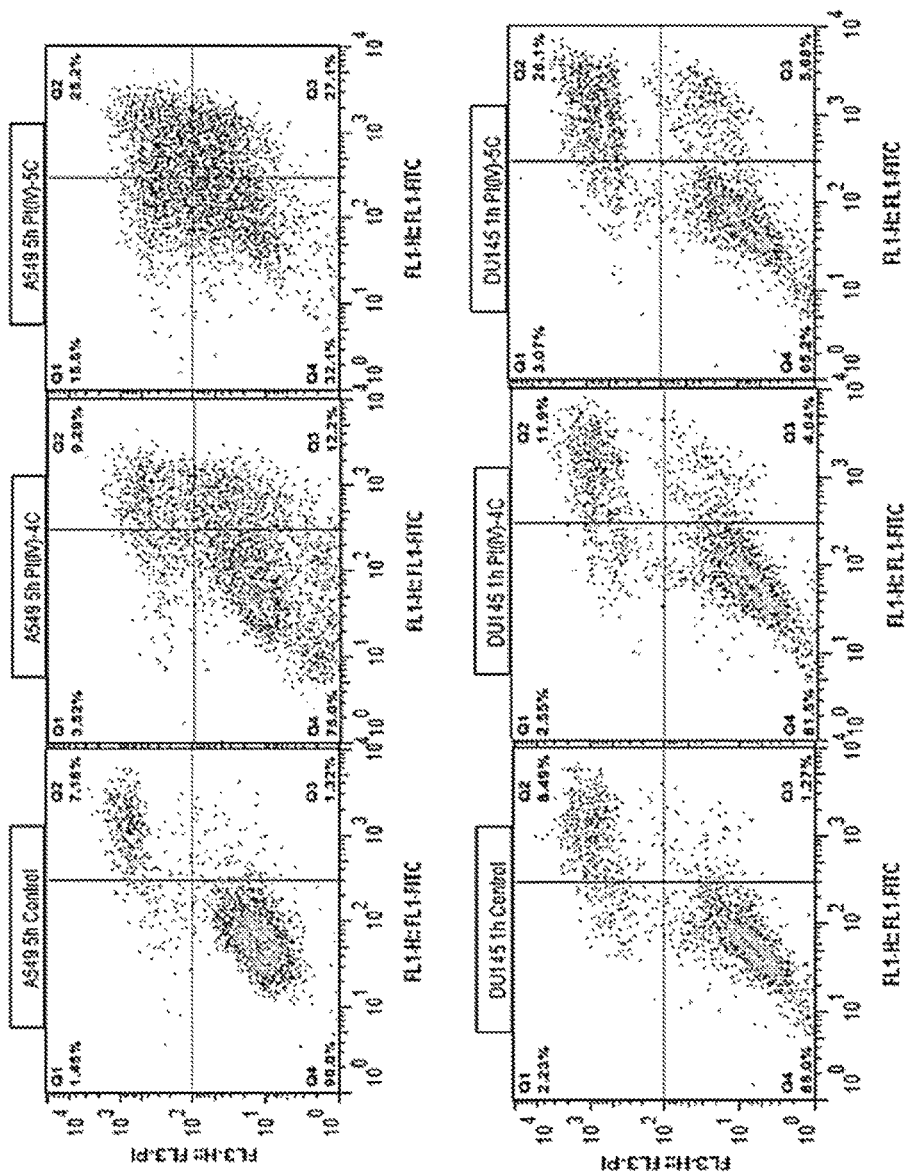
FIG. 11 is a series of graphs showing flow cytometry analysis of Annexin V/PI staining in A549 cells (top) and DU145 cells (bottom) treated with Pt(IV)-4C and Pt(IV)-5C. A549 cells were treated for 5 hours with control (left), 25 µM Pt(IV)-4C (center), or 10 µM Pt(IV)-5C (right), and analyzed 12 hours post treatment. DU145 cells were treated for 1 hour with control (left), 10 µM Pt(IV)-4C (center), or 2.5 µM Pt(IV)-5C (right) and analyzed 12 hours post treatment. Q1=PI+, represents necrotic cells; Q2=Annexin V/PI+, representing late apoptotic/necrotic cells; Q3=Annexin V+, representing early apoptotic cells; Q4=AnnexinV/PI−, representing live cells. Data are representative of three independent experiments.

The sub-G1 peak is a measurement of cells with less DNA than cells in the G1 phase, which is attributed to leakage of DNA content from cells undergoing late apoptosis or necrosis. Since the sub-G1 peak is not a clear indication of apoptosis, flow cytometric analysis of Annexin V and PI double staining was performed. Annexin V binds to exposed phosphatidylserine on the membrane surface, which is an event that occurs in early apoptosis. Co-staining with PI, a membrane impermeable dye, allows for differentiation between cells with intact membrane and cells with membrane damage, which occurs in late stage apoptosis or necrosis. As shown in FIG. 11, A549 and DU145 cells treated with Pt(IV)-4C and Pt(IV)-5C had decreased AnnexinV/PI negative cells (Q4, live cells) and a corresponding increase in Annexin V positive (Q3, early apoptotic cells) and Annexin V/PI positive cells (Q2, late apoptotic/necrotic cells). These changes were greater in Pt(IV)-5C treated cells than in Pt(IV)-4C treated cells. A549 cells treated with Pt(IV)-5C also had an increase in PI positive cells (Q1, necrotic cells) (FIG. 11, top). DU145 cells had greater increases in Annexin V/PI positive cells than Annexin V positive cells, suggesting that they may be in late stage apoptosis or necrosis (FIG. 11, bottom). Together, these results indicate that Pt(IV)-4C and Pt(IV)-5C induce apoptosis in A549 and DU145 cells, although some necrosis also was observed.

Analysis of Hoechst (Ho) and PI staining by confocal microscopy also was performed to detect cell death. PI stains cells with membrane damage, whereas Ho stains both live and apoptotic cells (although apoptotic cells have more intense Ho fluorescence). A549 cells treated with Pt(IV)-4C and Pt(IV)-5C had increased Ho fluorescence as compared to control. There was no difference between the PI fluorescence of Pt(IV)-5C treated cells as compared to the control, but Pt(IV)-4C treated cells had increased PI positive cells. Similar results were obtained for DU145 cells, except that Pt(IV)-5C treated cells had more PI positive staining than Ho staining as compared to the control. Additionally, unlike A549, the PI positive cells in Pt(IV)-4C treated cells were higher than Pt(IV)-5C treated cells. The increase in PI staining suggests that the cells have membrane damage, indicating that the cells were either at late stage apoptosis or were undergoing necrosis. These results correspond to the flow results indicating that Pt(IV)-4C and Pt(IV)-5C induce apoptosis and possibly some necrosis.

Figure 12:
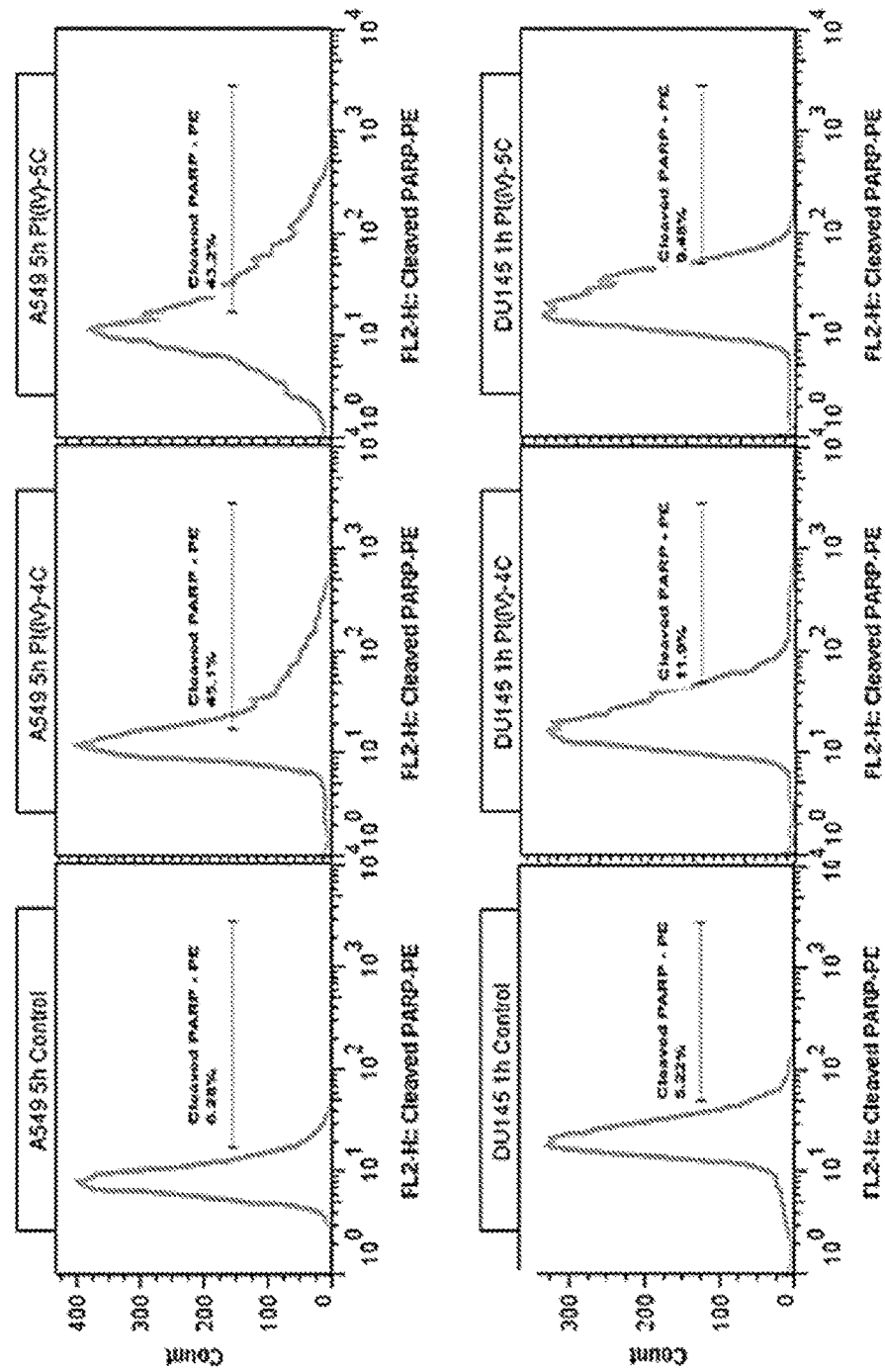
FIG. 12 is a series of histograms indicating Pt(IV)-4C and Pt(IV)-5C-induced cleavage of PARP in A549 cells (top panels) and in DU145 cells (bottom). A549 cells were treated for 5 hours with control (left), 25 µM Pt(IV)-4C (center), or 7.5 µM Pt(IV)-5C (right), and analyzed 12 hours post treatment. DU145 cells were treated for 2 hours with control (left), 10 µM Pt(IV)-4C (center), or 2.5 µM Pt(IV)-5C (right), and analyzed seven hours post treatment. Data are representative of three independent experiments.

In addition, detection of cleaved-PARP by flow cytometry was used as an indication of apoptosis. PARP is a nuclear poly (ADP-ribose) polymerase that has been associated with DNA repair. During apoptosis, PARP is cleaved by caspase-3 (Boulares et al., *J Biol Chem* 274:22932-22940, 1999). As shown in FIG. 12, both A549 and DU145 cells treated with Pt(IV)-4C and Pt(IV)-5C had increased levels of cleaved-PARP, suggesting that Pt(IV)-4C and Pt(IV)-5C induced caspase-3 mediated apoptosis in these two cell lines. The fold increase of cleaved-PARP in A549 (~7 fold for both compounds) was higher than in DU145 (~2 fold for both compounds). Similar to the flow data with PI staining, the differences between A549 and DU145 may be due to treatment time or p53 status.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating a subject having cancer, the method comprising administering to the subject an effective amount of a composition comprising a complex having a structure represented by a formula selected from:

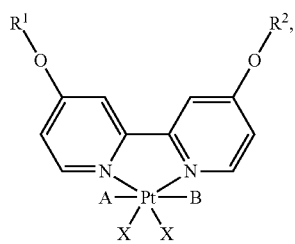

-continued

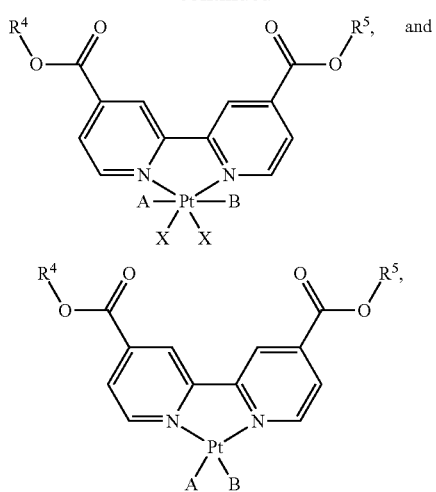

wherein each X, when present, is independently —Br, —Cl, or —I; and wherein each of A and B is independently selected from —Br, —Cl, —I, —OH, and —OC(O)R³;

wherein R³ is —(CH₂)ₚCH₃;

wherein p is selected from 0, 1, 2, 3, 4, 5, 6, 7, 8, 9, and 10;

wherein each of R¹ and R² is independently selected from —(CH₂)ₙCH₃, —(CH₂)ₙOCH₃, and —(CH₂)ₙ[O(CH₂)ₘ]ᵧO(CH₂)ᵤCH₃;

wherein n is selected from 1, 2, 3, 4, 5, 6, 7, 8, 9, and 10;

wherein each of m, y, and z is independently selected from 0, 1, 2, 3, 4, 5, 6, 7, 8, 9, and 10;

wherein each of R⁴ and R⁵ is independently selected from —(CH₂)ₜCH₃, —C(CH₃)₃, —CH₂CH(CH₂CH₃)CH₂CH₂CH₂CH₃, —(CH₂CH₂O)₂CH₂CH₃, —(CH₂CH₂O)₃CH₂CH₃, —(CH₂CH₂O)₃(CH₂)₃CH₃, and —(CH₂CH₂O)₄CH₃; and wherein t is selected from 0, 1, 2, 3, 4, 5, 6, and 7, or a pharmaceutically acceptable derivative thereof.

2. The method of claim 1, wherein the subject is a human.

3. The method of claim 1, wherein cancer is breast cancer, prostate cancer, lung cancer, or melanoma.

4. The method of claim 1, wherein the complex has a structure represented by a formula selected from:

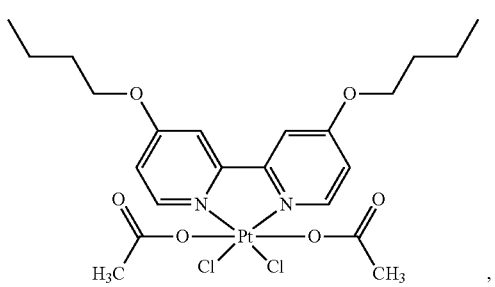

-continued

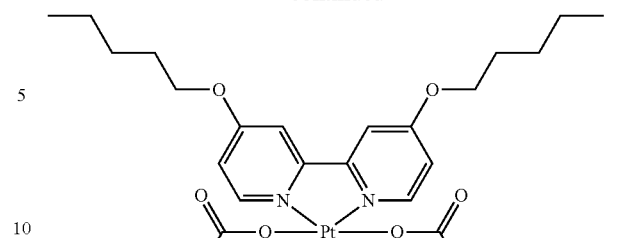

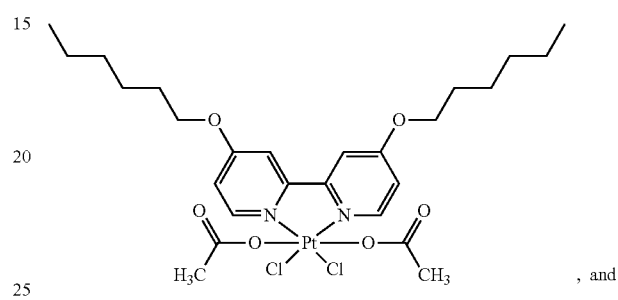

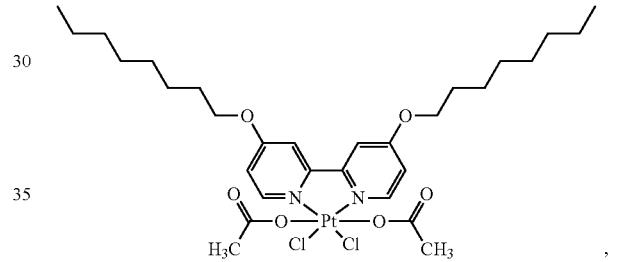

or a pharmaceutically acceptable derivative thereof.

5. The method of claim 1, wherein the complex has a structure represented by a formula:

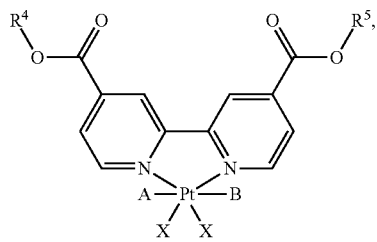

or a pharmaceutically acceptable derivative thereof.

6. The method of claim 5, wherein each of A and B is independently selected from —OH, and —OC(O)(CH₂)ₚCH₃.

7. The method of claim 5, wherein each of A and B is —OC(O)CH₃.

8. The method of claim 1, wherein the complex has a structure represented by a formula:

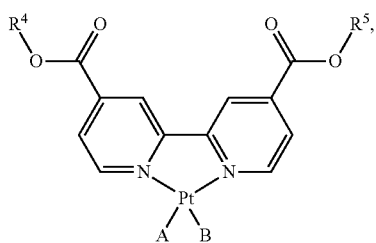

or a pharmaceutically acceptable derivative thereof.

9. The method of claim 8, wherein each of A and B is independently selected from —OH, and —OC(O)(CH$_2$)$_p$CH$_3$.

10. The method of claim 8, wherein each of A and B is —OC(O)CH$_3$.

11. The method of claim 1, wherein the complex has a structure represented by a formula:

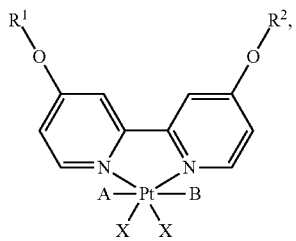

or a pharmaceutically acceptable derivative thereof.

12. The method of claim 11, wherein each X is —Cl.

13. The method of claim 11, wherein each of A and B is independently selected from —OH, and —OC(O)(CH$_2$)$_p$CH$_3$.

14. The method of claim 11, wherein each of A and B is —OC(O)(CH$_2$)$_p$CH$_3$.

15. The method of claim 11, wherein each of A and B is —OC(O)CH$_3$.

16. The method of claim 11, wherein p is 0.

17. The method of claim 11, wherein each of R$^1$ and R$^2$ is —(CH$_2$)$_n$CH$_3$.

18. The method of claim 11, each of R$^1$ and R$^2$ is independently selected from —(CH$_2$)$_n$OCH$_3$, and —(CH$_2$)$_n$[O(CH$_2$)$_m$]$_y$O(CH$_2$)$_z$CH$_3$.

19. The method of claim 11, wherein n is selected from 1, 2, 3, 4, 5, 6, and 7.

20. The method of claim 1, wherein cancer is breast cancer, prostate cancer, lung cancer, or melanoma and wherein the complex has a structure represented by a formula selected from:

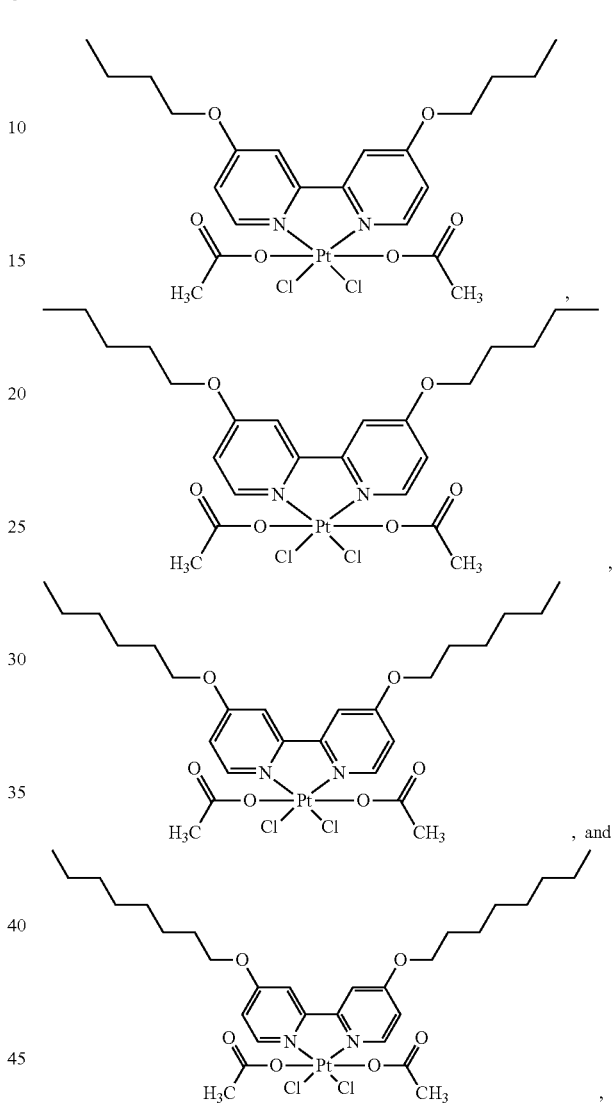

or a pharmaceutically acceptable derivative thereof.

* * * * *